(12) United States Patent
Gardner et al.

(10) Patent No.: US 8,306,752 B1
(45) Date of Patent: Nov. 6, 2012

(54) METHOD TO DETERMINE TRANSCRIPTIONAL REGULATION PATHWAYS IN ORGANISMS

(75) Inventors: Timothy S. Gardner, Needham, MA (US); James J. Collins, Newton, MA (US); Boris Hayete, Arlington, MA (US); Jeremiah Faith, Boston, MA (US)

(73) Assignee: Trustees of Boston University, Boston, MA (US)

( * ) Notice: Subject to any disclaimer, the term of this patent is extended or adjusted under 35 U.S.C. 154(b) by 757 days.

(21) Appl. No.: 12/271,944

(22) Filed: Nov. 17, 2008

Related U.S. Application Data

(63) Continuation of application No. PCT/US2007/011966, filed on May 17, 2007.

(60) Provisional application No. 60/800,978, filed on May 17, 2006.

(51) Int. Cl.
*G06F 7/00* (2006.01)

(52) U.S. Cl. ............. 702/19; 702/20; 703/11; 707/700; 435/6.1

(58) Field of Classification Search ........................ None
See application file for complete search history.

(56) References Cited

U.S. PATENT DOCUMENTS 6,468,476 B1 * 10/2002 Friend et al. ...................... 506/9
7,869,957 B2 * 1/2011 Palsson et al. .................. 702/19

OTHER PUBLICATIONS

Butte, A.J. et al., Proceedings of the Pacific Symposium on Biocomputing, pp. 415-426 (2000). "Mutual information relevance networks: functional genomic clustering using pairwise entropy measurements."
Daub, C.O. et al., BMC Bioinformatics, 5(1):118 (2004). "Estimating mutual information using B-spline functions—an improved similarity measure for analysing gene expression data."
Faith, J. et al., PLOS Biology, 5(1):54-66 (2007). "Large-scale mapping and validation of *Escherichia coli* transcriptional regulation from a compendium of expression profiles."
Margolin, A. et al., BMC Bioinformatics, 7(suppl 1):S7, 1-S7, 15 (2006). "ARACNE: An algorithm for the reconstruction of gene regulatory networks in a mammalian cellular context."

\* cited by examiner

*Primary Examiner* — Mary Zeman
(74) *Attorney, Agent, or Firm* — Nixon Peabody LLP; Ronald I. Eisenstein; Mark J. FitzGerald

(57) ABSTRACT

The invention relates to computer-implemented methods and systems for identifying regulatory relationships between expressed regulating polypeptides and targets of the regulatory activities of such regulating polypeptides. More specifically, the invention provides a new method for identifying regulatory dependencies between biochemical species in a cell. In particular embodiments, provided are computer-implemented methods for identifying a regulatory interaction between a transcription factor and a gene target of the transcription factor, or between a transcription factor and a set of gene targets of the transcription factor. Further provided are genome-scale methods for predicting regulatory interactions between a set of transcription factors and a corresponding set of transcriptional target substrates thereof.

36 Claims, 37 Drawing Sheets

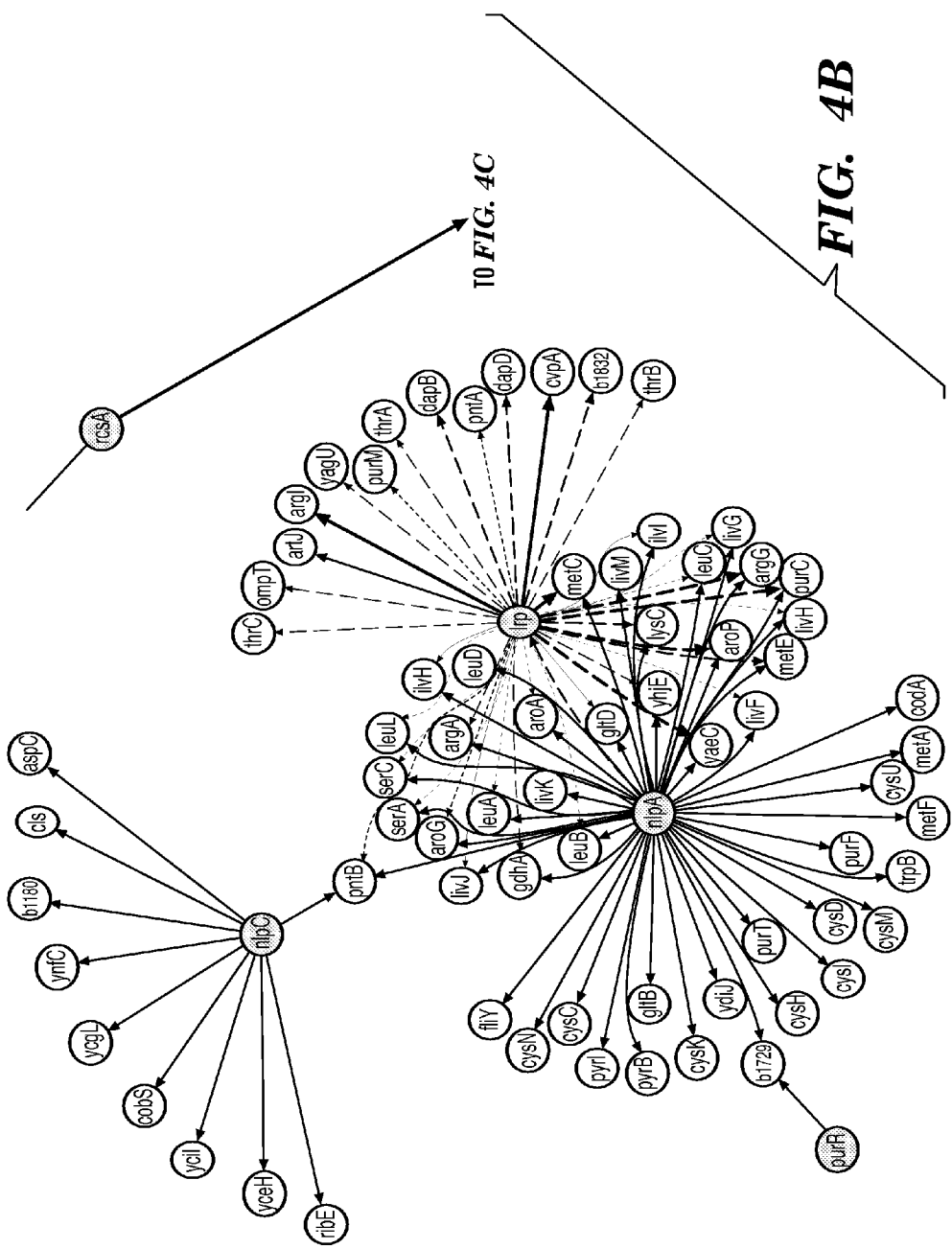

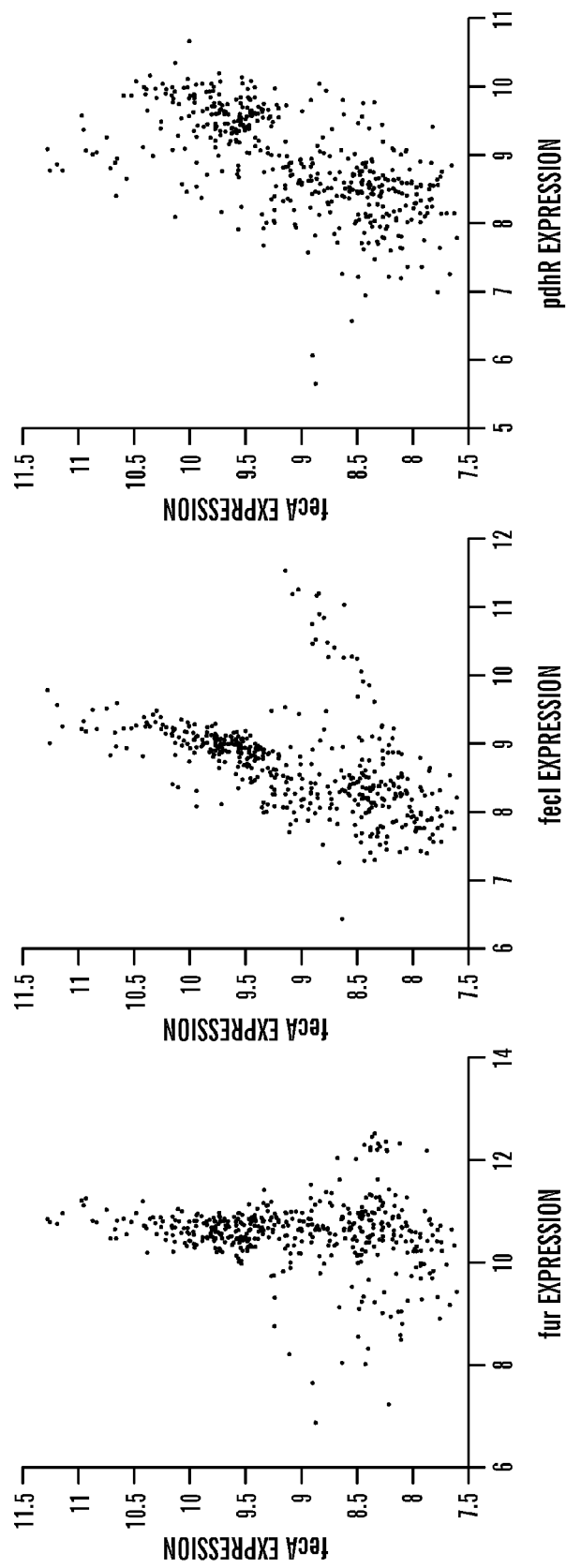

```
                        SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      consensus motif for E. coli LexA binding

<400> SEQUENCE: 1
tttactgtat atacaaacag                                              20

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      consensus motif for E. coli Lrp binding

<400> SEQUENCE: 2
atatacaatt gaattaacat tc                                           22

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      consensus motif for E. coli YnaE binding
<220> FEATURE:
<221> NAME/KEY: modified_base
<222> LOCATION: (14)..(14)
<223> OTHER INFORMATION: a, c, t or g
<220> FEATURE:
<221> NAME/KEY: modified_base
<222> LOCATION: (18)..(18)
<223> OTHER INFORMATION: a, c, t or g

<400> SEQUENCE: 3
acgaagtagt ttanttangg a                                            21

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      consensus binding motif
```

```
<400> SEQUENCE: 4
mvctgdwbrh vhwhmcakbd                                            20

<210> SEQ ID NO 5
<211> LENGTH: 17
<212> TYPE: DNA
<213> ORGANISM: Escherichia coli

<400> SEQUENCE: 5
agttgttaaa atgtgca                                               17

<210> SEQ ID NO 6
<211> LENGTH: 17
<212> TYPE: DNA
<213> ORGANISM: Escherichia coli

<400> SEQUENCE: 6
aattggtaag accaatt                                               17

<210> SEQ ID NO 7
<211> LENGTH: 52
<212> TYPE: DNA
<213> ORGANISM: Escherichia coli

<400> SEQUENCE: 7
ggaaaataat tcttatttcg attgtcctt ttacccttct cgttcgactc at          52

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      consensus binding motif

<400> SEQUENCE: 8
ddhvctgtay rhhhwhhcag                                            20

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      consensus binding motif

<400> SEQUENCE: 9
dhddmwhhhs vawwwwhryd h                                          21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      consensus binding motif
<220> FEATURE:
<221> NAME/KEY: modified_base
<222> LOCATION: (14)..(14)
<223> OTHER INFORMATION: a, c, t or g
<220> FEATURE:
```

-continued

```
<221> NAME/KEY: modified_base
<222> LOCATION: (18)..(18)
<223> OTHER INFORMATION: a, c, t or g

<400> SEQUENCE: 10
rcvmakbmkw tdmnkhwnkv m                                          21
```

METHOD TO DETERMINE TRANSCRIPTIONAL REGULATION PATHWAYS IN ORGANISMS

CROSS REFERENCE TO RELATED APPLICATIONS

This application claims benefit of priority as applicable under 35 U.S.C. §120 as a continuation of PCT/US2007/011966, filed May 17, 2007, which claims the priority of U.S. Provisional Application No. 60/800,978, filed May 17, 2006, the contents of which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Aug. 23, 2012, is named 71586597.txt and is 2,879 bytes in size.

GOVERNMENT SUPPORT

This invention was made with Government Support under Contract No. DE-FG02-04ER63803 awarded by the Department of Energy, Grant No. EF-0425719 awarded by the National Science Foundation and Grant No. HV28178 awarded by the National Institutes of Health. The Government has certain rights in this invention.

BACKGROUND OF THE INVENTION

High-throughput genome sequencing and bioinformatics technologies have dramatically eased the task of genomic annotation, producing parts lists of living organisms as simple as Mycoplasmas and as complex as mammals. What took decades of work in the past can now be completed in a few months[1]. Further progress in understanding of an organism's biology requires development and refinement of techniques to determine the dynamic interactions among an organism's molecular parts[2]. A major difficulty of this task is the context-specific nature of gene regulation. The total space of possible transcriptional regulatory interactions for an organism is the number of transcription factors multiplied by the number of genes multiplied by the number of environmental contexts in which the cell might find itself. Methods to identify regulatory interactions must efficiently determine the thousands of true regulatory interactions out of the billions of possible ones.

Pioneering efforts to identify regulatory interactions on a genome-scale have used machine-learning algorithms to identify cis-regulatory motifs or transcription factor target genes using a large set of expression arrays[3-18], genome-wide location analysis (ChIP-Chip)[19,20], or a combination of these and other high-throughput methods[21-26]. In general, the accuracy of these methods has been evaluated by testing for functional enrichment of co-regulated genes, experimental confirmation of selected regulatory relationships, or cross-validation within the training data set. However, rigorous validation of the accuracy of these methods at the genome scale has remained elusive due to the lack of a model organism with both a known regulatory structure and compatible experimental data. Therefore the relative merits and broader utility of these approaches remain difficult to judge.

SUMMARY OF THE INVENTION

The invention relates to computer-implemented methods and systems for identifying regulatory relationships between expressed regulating polypeptides and targets of the regulatory activities of such regulating polypeptides. More specifically, the invention provides a new method for identifying regulatory dependencies between biochemical species in a cell. In particular embodiments, provided are computer-implemented methods for identifying a regulatory interaction between a transcription factor and a gene target of the transcription factor, or between a transcription factor and a set of gene targets of the transcription factor. Further provided are genome-scale methods for predicting regulatory interactions between a set of transcription factors and a corresponding set of transcriptional target substrates thereof.

The invention also provides computer-readable media comprising instructions for permitting, when executed by a processor, each of the methods as described herein for identifying regulatory interactions, relationships or dependencies between biochemical species in a cell, identifying a candidate gene target of a transcription factor, and for predicting a plurality of regulatory interactions between a set of transcription factors and a corresponding set of transcriptional target substrates thereof. The invention also provides systems for performing each of the methods as described herein.

In one aspect, then, provided herein is a computer-implemented method for identifying a regulatory interaction between a transcription factor and a gene target of the transcription factor, the method comprising: a) providing a compendium of biochemical expression measurements reflecting gene expression for a set of biochemical species in an organism wherein at least a subset of the species are transcription factors and a second subset of the species are gene targets of transcription factors; b) in a computer, computing mutual information between members of the set of biochemical species; c) in a computer, applying a background correction to each such mutual information value so as to identify a set of those mutual information values that are significantly higher than background mutual information values, wherein the set of mutual information values identified in step (c) identifies a regulatory interaction between a transcription factor and a gene target of the transcription factor.

In one embodiment of this and other aspects of the invention as described herein, the computer in step (b) can be the same computer or a different computer from that in step (c).

In one embodiment of this and other aspects of the invention as described herein, the mutual information is pairwise mutual information. Alternatively, the mutual information can be higher order mutual information. The mutual information can be computed using one or more of a B-spline approximation, a kernel density estimator, and a discrete approximation.

In one embodiment of this and other aspects of the invention as described herein, the compendium of biochemical expression measurements comprises microarray data. The biochemical expression measurements can comprise one or more of mRNA concentration data, protein concentration data, protein activity data, and metabolite concentration or activity data.

In one embodiment of this and other aspects of the invention as described herein, the organism is a microorganism. The microorganism can be a eukaryotic or prokaryotic microorganism.

In one embodiment of this and other aspects of the invention as described herein, the compendium of biochemical expression measurements comprises measurements taken when the organism is subject to at least two different environmental conditions or stimuli. It is preferred that the compendium includes data obtained when the organism is subject to a number of different perturbations, environmental conditions or stimuli, e.g., at least three or more, at least four or more, at least five or more, at least ten or more, at least fifteen or more or at least twenty or more. In one embodiment, the compendium of biochemical expression measurements comprises a measurement taken when the organism is contacted with an antibiotic.

In one embodiment of this and other aspects of the invention as described herein, the methods further comprise the step, after step (c), of confirming a physical interaction of a transcription factor with an identified candidate gene target.

In one embodiment of this and other aspects of the invention as described herein, the background correction is determined by a process comprising the step of computing a background distribution for each mutual information score computed in step (b).

In one embodiment of this and other aspects of the invention as described herein, the step of computing mutual information generates an adjacency matrix or a computationally equivalent representation of mutual information values describing pairwise expression relationships between species represented in said compendium, the matrix having rows and columns of mutual information values, wherein the value in each cell in the matrix is the mutual information between two genes' expression profiles.

In one embodiment of this and other aspects of the invention as described herein, the step of applying a background correction comprises the steps of estimating a likelihood of the mutual information score, MI, for a given pair of genes, genes i and j, representing row or column i and row or column j of said adjacency matrix, by comparing the mutual information score, $MI_{ij}$, for that pair to a background distribution of mutual information values.

In one embodiment of this and other aspects of the invention as described herein, the background distribution is determined through a process comprising: i) providing two sets of MI values: $\{MI_i\}$, the set of all mutual information values for gene i, in row or column i of the matrix; and $\{MI_j\}$, the set of mutual information values for gene j, in row or column j of the matrix; and ii) calculating marginal empirical distribution $P_i$ and $P_j$ for each set of MI values using an empirical distribution estimation method, then combining into a joint empirical distribution.

In one embodiment of this and other aspects of the invention as described herein, the combining step comprises the product of marginal empirical distributions as $P_i * P_j$.

In one embodiment of this and other aspects of the invention as described herein, the empirical distribution estimation method comprises use of a kernel density estimator or a histogram.

In one embodiment of this and other aspects of the invention as described herein, the kernel density estimator is a Gaussian kernel density estimator.

In one embodiment of this and other aspects of the invention as described herein, the background distribution is determined through a process comprising: i) providing two sets of MI values: $\{MI_i\}$, the set of all mutual information values for gene i, in row or column i of the matrix; and $\{MI_j\}$, the set of all mutual information values for gene j, in row or column j of the matrix; and ii) approximating a marginal probability density function $g_i(MI_i)$ and $g_j(MI_j)$ for $MI_i$ and $MI_j$ using an analytical function, and combining the probability density functions using a composite analytical function.

In one embodiment of this and other aspects of the invention as described herein, the analytical function is a Gaussian analytical distribution fitted to the set of values of mutual information, $\{MI_i\}$.

In one embodiment of this and other aspects of the invention as described herein, the analytical function is a Rayleigh analytical distribution fitted to the set of values of mutual information, $\{MI_i\}$.

In one embodiment of this and other aspects of the invention as described herein, the composite analytical function is a function of $g_i(MI_i)$ and $g_j(MI_j)$, $f(g(\{MI_i\}), g(MI_i)))$, that represents the probability of the joint function given the two marginal probability density function fits $g_i(MI_i)$ and $g_j(MI_j)$.

In one embodiment of this and other aspects of the invention as described herein, the composite analytical function comprises a Stouffer method averaging composite function or a $(Z_i+Z_j)/\sqrt{2}$ averaging composite function where $Z_i$ and $Z_j$ are z-scores computed from the two marginal probability density functions.

In one embodiment of this and other aspects of the invention as described herein, the composite analytical function comprises the product of marginal probability density functions $g_i(MI_i)$ and $g_j(MI_j)$.

In one embodiment of this and other aspects of the invention as described herein, the step of comparing the mutual information score comprises calculating a score by determining the MI pair score in its relative position within probability density functions $g_i(MI_i)$ and $g_j(MI_j)$ calculated for $MI_i$ and $MI_j$ using an analytical function.

In one embodiment of this and other aspects of the invention as described herein, the relative position is computed as a z-score for normal distributions or the relative position is computed as a p-value.

In one embodiment of this and other aspects of the invention as described herein, the method further comprises the step, after step (c), of confirming a physical interaction of a transcription factor with a predicted gene target.

In one embodiment of this and other aspects of the invention as described herein, the computer in steps (b) and (c) is the same computer device.

In one embodiment of this and other aspects of the invention as described herein, the computer in step (b) is not the same computer device as that used for step (c).

In another aspect, provided herein is a computer-implemented method for identifying a candidate gene target of a transcription factor, the method comprising: a) providing a compendium of biochemical expression measurements reflecting gene expression for a set of biochemical species in an organism wherein at least a subset of the species comprises transcription factors and a second subset of the species comprises gene targets of transcription factors; b) in a computer, computing mutual information between members of the set of biochemical species; c) in a computer, applying a background correction to each mutual information value so as to identify a set of those mutual information values that are significantly higher than background mutual information values, wherein the set of mutual information values identified in step (c) identifies a candidate gene target of a subject transcription factor. This aspect and others described herein can encompass specific embodiments as set out for the previously described aspect. For example, embodiments of this method can include, without limitation, those relating to specified approaches for the background correction step and for computing mutual information.

In another aspect, provided herein is a computer-implemented, genome-scale method for predicting a plurality of regulatory interactions between a set of transcription factors and a corresponding set of transcriptional target substrates thereof, comprising: a) providing a compendium of biochemical expression measurements reflecting gene expression for a set of biochemical species in an organism wherein at least a subset of the species comprises transcription factors and a second subset of the species comprises transcriptional target substrates of transcription factors; b) in a computer, computing mutual information between members of the set of biochemical species; c) in a computer, applying a background correction to each mutual information value so as to identify a set of those mutual information values that are significantly higher than background mutual information values, wherein the set of mutual information values identified in step (c) identifies a plurality of regulatory interactions between a set of transcription factors and a corresponding set of transcriptional target substrates thereof. This aspect and others described herein can encompass specific embodiments as set out for the previously described aspect. This aspect and others described herein can encompass specific embodiments as set out for the previously described aspects. For example, embodiments of this method can include, without limitation, those relating to specified approaches for the background correction step and for computing mutual information.

In another aspect, provided herein is a computer-implemented method for identifying regulatory dependencies between biochemical species in a cell, the method comprising: a) providing a compendium of biochemical expression measurements reflecting gene expression for a set of biochemical species in an organism; b) in a computer, computing mutual information between members of the set of biochemical species; c) in a computer, applying a background correction to each mutual information value so as to identify a set of those mutual information values that are significantly higher than background mutual information values, wherein the set of mutual information values identified in step (c) identifies a regulatory dependency between two members of the set of biochemical species. This aspect and others described herein can encompass specific embodiments as set out for the previously described aspects. For example, embodiments of this method can include, without limitation, those relating to specified approaches for the background correction step and for computing mutual information.

In another aspect, provided herein is a computer-readable medium comprising instructions for permitting a method, when executed by a processor, for identifying a regulatory interaction between a transcription factor and a gene target of the transcription factor, the method comprising: a) providing a compendium of biochemical expression measurements reflecting gene expression for a set of biochemical species in an organism wherein at least a subset of the species are transcription factors and a second subset of the species are gene targets of transcription factors; b) in a computer, computing mutual information between members of the set of biochemical species; c) in a computer, applying a background correction to each mutual information value so as to identify a set of those mutual information values that are significantly higher than background mutual information values, wherein the set of mutual information values identified in step (c) identifies a regulatory interaction between a transcription factor and a gene target of the transcription factor. This aspect and others described herein can encompass specific embodiments as set out for the previously described aspects. For example, embodiments of the method permitted by the instructions on the computer-readable medium can include, without limitation, those relating to specified approaches for the background correction step and for computing mutual information.

In one embodiment of this and other computer-readable media described herein, the computer-readable medium further comprises a compendium of biochemical expression measurements reflecting gene expression for a set of biochemical species in an organism wherein at least a subset of the species are transcription factors and a second subset of the species are gene targets of transcription factors.

In another aspect, provided herein is a computer-readable medium comprising instructions for permitting a method, when executed by a processor, for identifying a gene target of a transcription factor, the method comprising: a) providing a compendium of biochemical expression measurements reflecting gene expression for a set of biochemical species in an organism wherein at least a subset of the species comprises transcription factors and a second subset of the species comprises gene targets of transcription factors; b) in a computer, computing mutual information between members of the set of biochemical species; c) in a computer, applying a background correction to each mutual information value so as to identify a set of those mutual information values that are significantly higher than background mutual information values, wherein the set of mutual information values identified in step (c) identifies a candidate gene target of a subject transcription factor. This aspect and others described herein can encompass specific embodiments as set out for the previously described aspects. For example, embodiments of embodiments of the method permitted by the instructions on the computer-readable medium can include, without limitation, those relating to specified approaches for the background correction step and for computing mutual information.

In another aspect, provided herein is a computer-readable medium comprising instructions for permitting a method, when executed by a processor, for predicting a plurality of regulatory interactions between a set of transcription factors and a corresponding set of transcriptional target substrates thereof, the method comprising: a) providing a compendium of biochemical expression measurements reflecting gene expression for a set of biochemical species in an organism wherein at least a subset of the species comprises transcription factors and a second subset of the species comprises transcriptional target substrates of transcription factors; b) in a computer, computing mutual information between members of the set of biochemical species; c) in a computer, applying a background correction to each mutual information value so as to identify a set of those mutual information values that are significantly higher than background mutual information values, wherein the set of mutual information values identified in step (c) identifies a plurality of regulatory interactions between a set of transcription factors and a corresponding set of transcriptional target substrates thereof. This aspect and others described herein can encompass specific embodiments as set out for the previously described aspects. For example, embodiments of the method permitted by the instructions on the computer-readable medium can include, without limitation, those relating to specified approaches for the background correction step and for computing mutual information.

In another aspect, provided herein is a system for identifying a regulatory interaction between a transcription factor and a gene target of said transcription factor, the system comprising: a) a database comprising a compendium of biochemical expression measurements reflecting gene expression for a set of biochemical species in an organism wherein at least a subset of the species are transcription factors and a second subset of the species are gene targets of transcription factors; and b) a computer system comprising a processor and a computer-readable medium comprising instructions for permitting a method, when executed by the processor, for identifying a gene target of a transcription factor, the method, using the processor and the instructions, comprising: i) computing mutual information between members of the set of biochemical species; and ii) applying a background correction to each mutual information value so as to identify a set of those mutual information values that are significantly higher than background mutual information values, wherein the set of mutual information values identified in step (ii) identifies a regulatory interaction between a transcription factor and a gene target of the transcription factor. This aspect and others described herein can encompass specific embodiments as set out for the previously described aspects. For example, embodiments of the method permitted by the instructions on the computer-readable medium comprised by the system can include, without limitation, those relating to specified approaches for the background correction step and for computing mutual information.

In another aspect, provided herein is a system for identifying a candidate gene target of a transcription factor, the system comprising: a) a database comprising a compendium of biochemical expression measurements reflecting gene expression for a set of biochemical species in an organism wherein at least a subset of the species comprises transcription factors and a second subset of the species comprises gene targets of transcription factors; and b) a computer system comprising a processor and a computer-readable medium comprising instructions for permitting a method, when executed by the processor, for identifying a candidate gene target of a transcription factor, the method, using the processor and the instructions, comprising: i) computing mutual information between members of the set of biochemical species; and ii) applying a background correction to each mutual information value so as to identify a set of those mutual information values that are significantly higher than background mutual information values, wherein the set of mutual information values identified in step (ii) identifies a candidate gene target of a subject transcription factor. This aspect and others described herein can encompass specific embodiments as set out for the previously described aspects. For example, embodiments of the method permitted by the instructions on the computer-readable medium comprised by the system can include, without limitation, those relating to specified approaches for the background correction step and for computing mutual information.

In another aspect, provided herein is a system for genome-scale method prediction of a plurality of regulatory interactions between a set of transcription factors and a corresponding set of transcriptional target substrates thereof, the system comprising: a) a database comprising a compendium of biochemical expression measurements reflecting gene expression for a set of biochemical species in an organism wherein at least a subset of the species comprises transcription factors and a second subset of the species comprises transcriptional target substrates of transcription factors; b) a computer system comprising a processor and a computer-readable medium comprising instructions for permitting a method, when executed by the processor, for prediction of a plurality of regulatory interactions between a set of transcription factors and a corresponding set of transcriptional target substrates thereof, the method, using the processor and the instructions, comprising: i) computing mutual information between members of the set of biochemical species; and ii) applying a background correction to each mutual information value so as to identify a set of those mutual information values that are significantly higher than background mutual information values, wherein the set of mutual information values identified in step (ii) predicts a plurality of regulatory interactions between a set of transcription factors and a corresponding set of transcriptional target substrates thereof. This aspect and others described herein can encompass specific embodiments as set out for the previously described aspects. For example, embodiments of the method permitted by the instructions on the computer-readable medium comprised by the system can include, without limitation, those relating to specified approaches for the background correction step and for computing mutual information.

In another aspect, provided herein is a system for identifying regulatory dependencies between biochemical species in a cell, the system comprising: a) a database comprising a compendium of biochemical expression measurements reflecting gene expression for a set of biochemical species in an organism; and b) a computer system comprising a processor and a computer-readable medium comprising instructions for permitting a method, when executed by the processor, for identifying regulatory dependencies between biochemical species in a cell, the method, using the processor and the instructions, comprising: i) computing mutual information between members of the set of biochemical species; ii) applying a background correction to each mutual information value so as to identify a set of those mutual information values that are significantly higher than background mutual information values, wherein the set of mutual information values identified in step (ii) identifies a regulatory dependency between two members of the set of biochemical species. This aspect and others described herein can encompass specific embodiments as set out for the previously described aspects. For example, embodiments of the method permitted by the instructions on the computer-readable medium comprised by the system can include, without limitation, those relating to specified approaches for the background correction step and for computing mutual information.

As used herein, the term "regulatory interaction" refers to the participation of one gene product in the regulation of a second gene product. Most often the term will be applied to the regulation, by one gene product, of the transcription of the gene for a second gene product. However, the term in its broader sense refers to a relationship between two biochemical species, such that an activity of the first species regulates an activity of the second species. By "an activity" is meant expression, including transcription and/or translation of a gene product, as well as enzymatic, binding, or other specific activity of the translated gene product relevant to its function in vivo.

As used herein, the term "gene product" encompasses not only a polypeptide product encoded by a gene, but also a transcript of a gene. Thus, a "gene product" can encompass both an RNA, e.g., an mRNA, and a polypeptide encoded by a nucleic acid or gene.

As used herein, the term "biochemical expression measurements" refers to data including the presence or absence, and preferably the absolute or relative amount, of a given biochemical species in a sample or set of samples taken under various sets of conditions. The term also refers to measurements of an activity, e.g., enzymatic activity, binding activity, gene expression activity, hybridization activity, absorbance, etc. of a biochemical species, that provides a readout or acts as an indirect reporter of the presence, absence or absolute or relative amount or activity of another biochemical species. Biochemical expression measurements expressly include, but are not limited mRNA concentration data, including, for example, microarray data, as well as protein concentration data, protein activity data, and metabolite concentration or activity data.

As used herein, the term "subset" means at least one member of a set comprising a plurality of members. A "subset" will be at least one member fewer than all of the members of a given set.

As used herein, the term "gene targets of transcription factors" refers to a gene, the expression of which is modulated by a given transcription factor. The term preferably refers to genes which are transcriptionally modulated by a given transcription factor, i.e., in which a given transcription factor binds to the gene's regulatory sequences and influences the transcription of the gene. In other words, a "gene target" of a transcription factor is a gene that responds to the regulatory activity of a transcription factor via physical interaction between the transcription factor and the regulatory sequences associated with the gene. An influence on the transcription of a gene can be positive or negative, and can affect not only the rate of transcription (measured, for example, as the number of transcripts generated per unit time), but also, for example, the processivity of transcription.

As used herein, the term "mutual information" refers to a statistical metric of similarity or dependence between two variables, e.g., between two gene expression profiles.

As used herein, the term "significantly higher" when used, for example, in the context of mutual information values that are significantly higher than background mutual information values, refers to values that are statistically significant/higher than the subject values. Statistical significance is reflected by one or more of the following: 1) The p-value (equal to the probability of a MI score occurring by chance, where chance is determined from the MI background distribution) of a particular interaction's score should be equal to or lower than a user-defined acceptability threshold, e.g. <0.2, or <0.1, or <0.05; 2) p-values may be converted to a False Discovery Rate, and the FDR score for an interaction should be equal to or lower than a user-defined acceptability threshold, e.g. <20%, <10%, or <5%; or 3) The z-score computed by comparing a MI interaction score to its background should exceed a user-defined acceptability threshold, e.g. >5, >6 or >7.

BRIEF DESCRIPTION OF THE FIGURES

FIG. 1 shows a "Sequence Analysis" consensus sequence as SEQ ID NO: 4.

DETAILED DESCRIPTION

Figure 1:
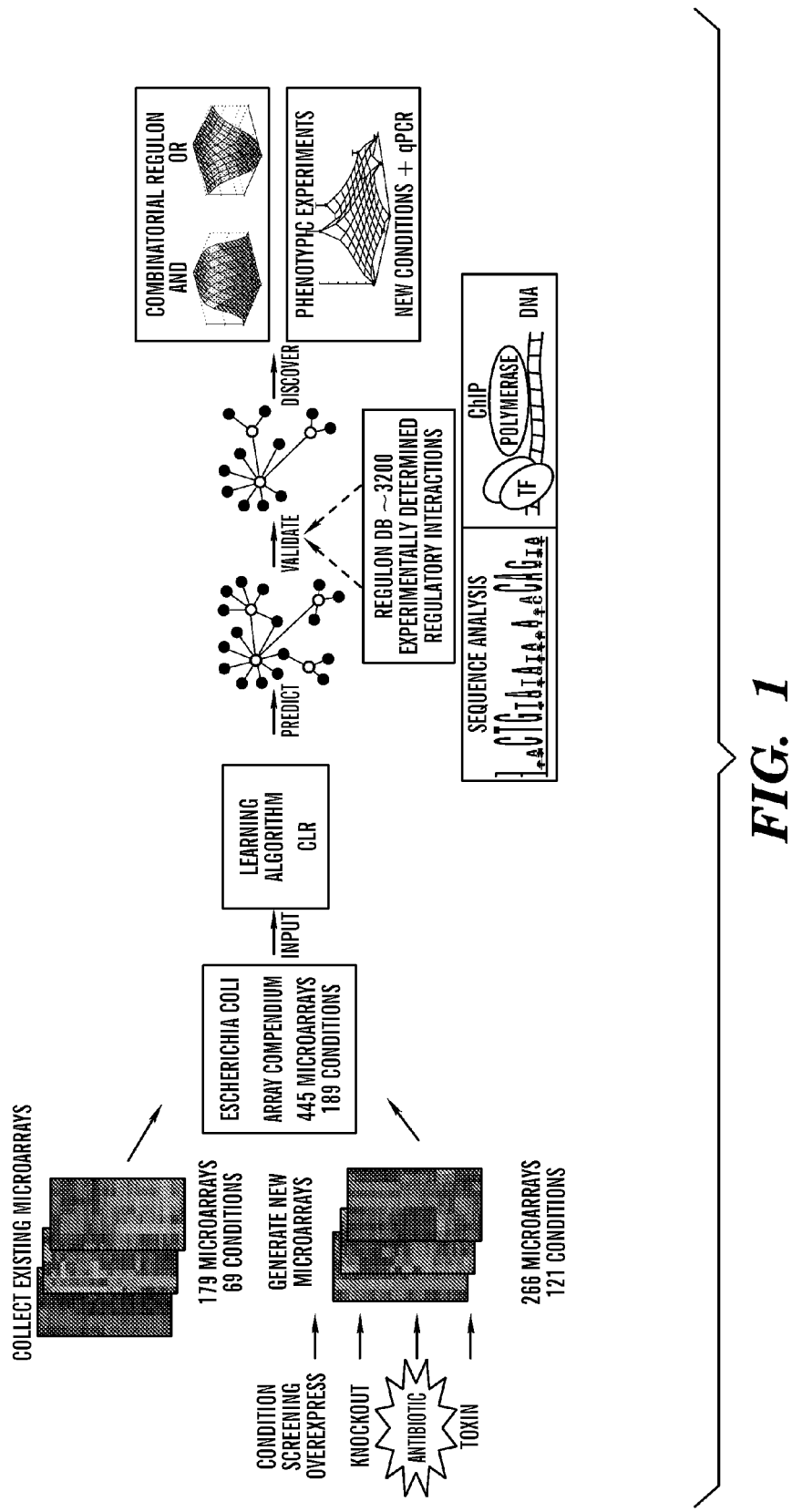
FIG. 1 shows an overview of the approach for mapping the *E. coli* transcriptional regulatory network. Microarray expression profiles were obtained from several investigators. Additional conditions were profiled, focusing on DNA damage, stress responses, and persistence. These two data sources were combined into one uniformly normalized *Escherichia coli* microarray compendium that was analyzed with the CLR network inference algorithm described herein. The predicted regulatory network was validated using RegulonDB, sequence analysis, and ChIP. The validated network was then examined for cases of combinatorial regulation, one of which was explored with follow-up quantitative RT-PCR experiments.

Disclosed herein are methods based upon or using a network inference algorithm, termed "Context Likelihood of Relatedness" (CLR), that uses expression profiles of an organism across a diverse set of conditions to systematically map transcriptional regulatory interactions, e.g., to identify binding relationships between DNA-binding proteins, e.g., transcription factors, and their cognate DNA sequences. This provides a genome-scale approach for mapping transcriptional regulatory networks in, for example, microbes.

The algorithm analyzes a compendium of biochemical expression measurements (for example microarray profiles of mRNA expression, or other quantitative measures of mRNA concentrations or activities, protein concentrations or activities, metabolite concentrations or activities) to identify the binding relationships. Embodiments of the invention may also be applied to identify dependencies between the concentrations and activities between biochemical species in the cell (e.g., increases in the expression of gene A are dependent on increases in expression of genes B and C.)

The algorithm works by first computing mutual information between biochemical species based on their biochemical expression measurements. Mutual information may be computed in a number of ways; in the embodiments described herein it was tested successfully with B-spline approximations, Kernel density estimators, and discrete approximations. The B-spline method is a preferable approach. While pairwise mutual information is exemplified in the Examples herein, the approach need not be limited to pairwise mutual information. Higher-order mutual information, correlation, or other metrics of similarity may be used in place of mutual information.

In a step central to the methods described herein, after computing mutual information, the algorithm computes and applies a background correction to the mutual information values to identify only those values that are significantly higher than background mutual information values. These values are selected as indicative of or predictive of true binding relationships or dependencies between biochemical species. The values that are not significant indicate that a binding relationship or dependency cannot be conclusively identified using the given data set. The background correction is applied separately to each mutual information value.

The methods disclosed herein have been applied in *Escherichia coli* to correctly identify binding relationships between DNA-binding proteins and DNA. The global performance of the approach was assessed using 3293 known regulatory interactions in *E. coli*, demonstrating a true positive rate greater than 80%. At this confidence level more than 200 novel regulatory interactions were identified, a number of which were tested and confirmed via chromatin immunoprecipitation and quantitative PCR. These novel regulatory pathways include a physical regulatory link providing central metabolic control of iron transport, the first such link identified in a microbe. This work indicates that it is possible to infer the regulatory map of an organism using relatively few expression profiles, allowing for rapid progression from a lab isolate to a blueprint of the organism's transcriptional regulatory network.

CLR Algorithm

The Context Likelihood of Relatedness (CLR) algorithm uses mutual information to detect dependencies between transcription factors and the genes they regulate. Like correlation, mutual information is a metric that detects statistical dependence between two variables. But unlike correlation, it does not assume linearity, continuity or other specific properties of the dependence. As such, mutual information possesses the flexibility to detect regulatory interactions that might be missed by linear measures such as the correlation coefficient. Mutual information has been previously applied to map gene regulatory interactions. In one approach termed the "Relevance Networks" algorithm, dependencies between a gene and a transcription factor are hypothesized to be biological interactions if the mutual information between the expression levels of the gene and its potential regulator across the set of expression-profiled biological conditions is above some set threshold. There are tradeoffs between accuracy and sensitivity in choosing a threshold. A high threshold results in a smaller, more accurate network, but it also eliminates potential novel interactions. Conversely, a low threshold will often capture false interactions due to a number of factors, including background correlation and misinterpretation of co-expression as direct dependence.

Rather than selecting an arbitrary threshold, the CLR approach adds a background correction step in a Relevance Networks algorithm to substantially improve both accuracy and sensitivity. After computing the mutual information between regulators and their potential target genes, CLR calculates the statistical likelihood of each mutual information value. In this step, the algorithm compares the mutual information between a transcription factor/gene pair to the "background" distribution of mutual information scores for all possible transcription factor/gene pairs that include either the transcription factor or its target. The most probable interactions are those whose mutual information scores stand significantly above the background of mutual information scores for all possible gene pairs that include the transcription factor or target gene. The CLR algorithm removes many of the false correlations in the network by eliminating "promiscuous" cases in which one transcription factor is weakly covarying with huge numbers of genes or one gene is weakly covarying with many transcription factors. Such promiscuity arises when the assayed conditions are inadequately or unevenly sampled, or when normalization fails to remove false background correlations due to inter-lab variations in methodology. CLR outputs a set of transcription factors and their inferred gene targets. Identified interactions are available on the $M^{3D}$ website as a graphical map, which can be accessed at m3d.bu.edu, and in the Tables herein below.

The new method for inferring regulatory networks described herein, the CLR, aims to assess the likelihood of a particular interaction in its network context. In particular examples described herein, the method first calculates mutual information[50] between all pairs of genes on Affymetrix microarrays across all experimental conditions. The output of this step is a square mutual information matrix for all genes in the genome. Then the probability of the mutual information score for each pair of genes is computed using the pair-specific background distribution of mutual information scores. The background distribution for each pair is approximated with a two-dimensional normal distribution (the distribution under the null hypothesis) that accounts for the background variance of both genes in the pair (see, e.g., FIG. 3a). This significance estimate is used as the measure of reliability of a given edge. To provide information relevant to transcriptional regulation, only the columns of the square matrix that correspond to known transcription factors are retained.

Gene expression profiles tend to exhibit a significant degree of weak, non-random similarities due to distal network effects: regulatory signals can propagate through cascades of connected genes resulting in weak similarities between indirectly connected genes. These similarities complicate the task of network inference, since indirect (functional) and direct (physical binding) relationships may not be easily told apart. This is especially true for a threshold-based algorithm that uses a similarity metric alone, such as the Relevance Networks algorithm. The new algorithm, CLR, increases the contrast between the desired physical and indirect relationships by taking the network context of each relationship into account. The CLR algorithm provides a form of background correction to the Relevance Networks algorithm. More generally, CLR constitutes a background correction, applicable to any statistical metric of similarity between gene expression profiles. For example, the method has been successfully tested with Pearson linear correlation as well as with mutual information.

Figure 3A:
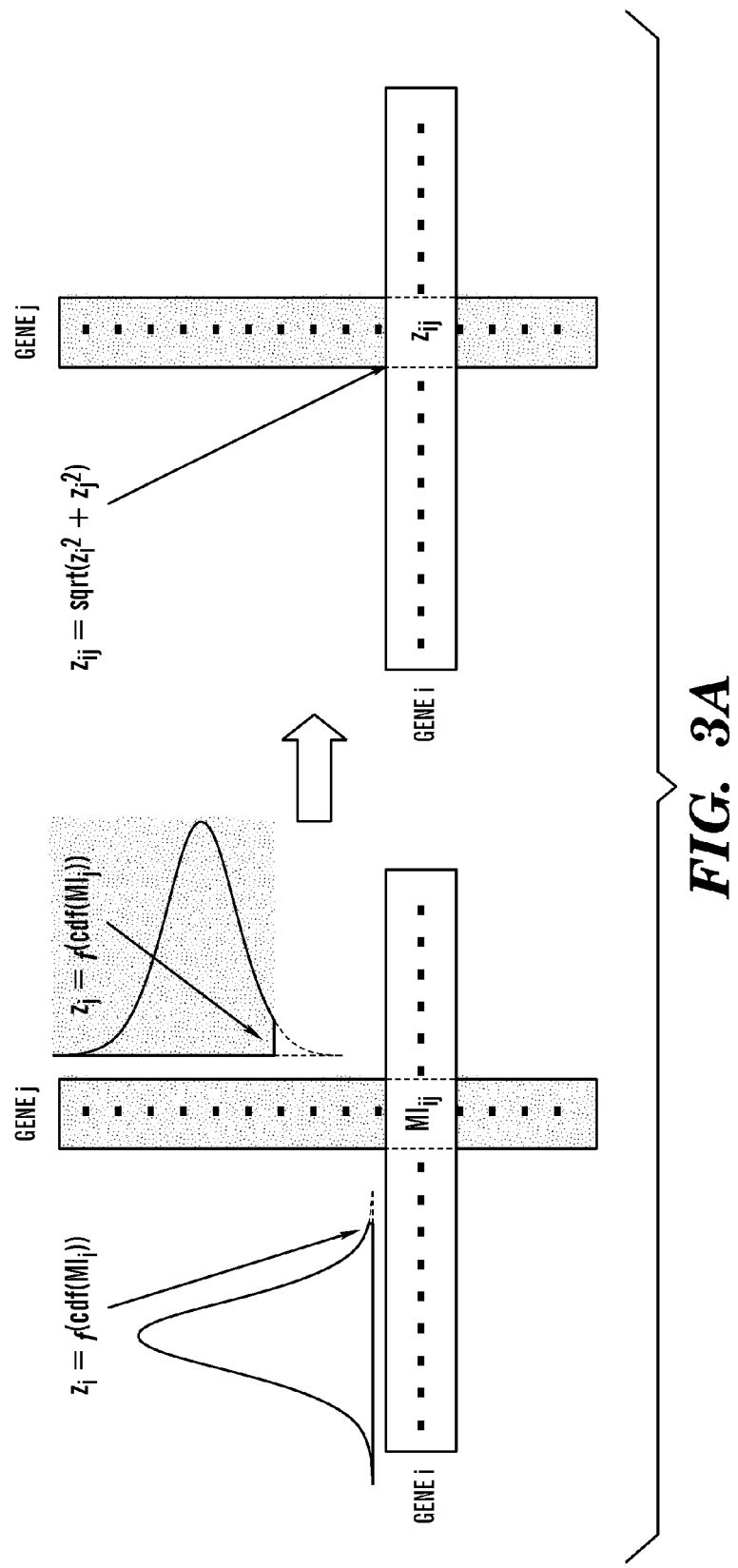
FIG. 3 shows the Context Likelihood of Relatedness (CLR) algorithm: methods and validation. (A) A schema of the CLR algorithm. The z-score of each regulatory interaction depends on the distribution of mutual information scores (MI) for all possible regulators of the target gene ($z_i$) and on the MI score distribution of all possible targets of the regulator gene ($z_j$). (B) Accuracy and sensitivity of CLR applied to all 4345 genes in the *E. coli* compendium of 445 microarrays was estimated using the 3293 known *E. coli* regulatory interactions in RegulonDB. The sensitivity scores are hindered by the RpoD sigma factor (solid line points). This sigma factor accounts for 24% of the known *E. coli* regulatory interactions. Removing it from the scoring set adjusts the sensitivity scores upwards (dashed line points). (C) Using 60 well-chosen arrays, we can infer a network, nearly equivalent in sensitivity and accuracy to the network inferred using all 445 microarrays in the compendium (dotted horizontal line), reflecting the redundancy of the compendium and the potential for improvement in choosing subsequent perturbations to profile. RpoD was included in the RegulonDB control set for calculating sensitivities in this analysis.

In a preferred aspect, the CLR algorithm is concerned with the genome-sized adjacency matrix of mutual information values describing pairwise expression relationships between all probe sets on, for example, the Affymetrix array. In this matrix, each row and column corresponds to a probe set (usually a gene or an intergenic region), and the value of each cell is the mutual information between the two probe sets' normalized expression profiles. In its most general form, the CLR algorithm estimates a likelihood of the mutual information (MI) score for a particular pair of genes, i and j, comparing the MI value for that pair to a background distribution of mutual information values (the null model). The background distribution is constructed empirically from two sets of MI values: $\{MI_i\}$, the set of all the mutual information values for gene i (in row or column i), and $\{MI_j\}$, the set of all the mutual information values for gene j (in row or column j) (FIG. 3a). Assuming that most MI scores in each row of the adjacency matrix are by chance (due to the random distribution of distal, indirect network relationships), the distributions of $\{MI_i\}$ and $\{MI_j\}$ are assumed to be independent. Thus, a joint p-value $P_{ij}$ may be computed as the product of the p-values for each independent distribution:

$$P_{ij} = P_i * P_j = (1 - ecdf(MI_{ij}|\{MI_i\})) * (1 - ecdf(MI_{ij}|\{MI_j\}))$$

where ecdf is the empirical cumulative density function of $\{MI_i\}$ or $\{MI_j\}$, evaluated up to the value $MI_{ij}$. This p-value, $P_{ij}$, can be used as an estimate of significance of mutual information, and represents a context-derived likelihood of the joint mutual information function.

In practice, ecdf does not give a smooth estimate of probability density of mutual information at the margins of a distribution, and especially at the significant right-tail margin where mutual information values are high and the sampling is sparse. In addition, probability values scale poorly for practical use. Therefore, in practice, two simplifications are applied, which give faster performance and better results.

First, the background MI scores are approximated as a joint normal distribution with $MI_i$ and $MI_j$, as independent variables. Although a normal distribution does not accurately describe the underlying probability density of mutual information, it seems to de-emphasize the significance of mutual information scores coming from distant network neighborhood: the normal is centered around its mean, whereas the true density function, heavily right-tailed, has a mean to the right of its peak. The distant network effects, or the indirect relationships, which account for the statistically significant weak correlations in the network, tend to occupy the space between the extreme right of the true distribution and its center, and thus lose much of their significance due to the bias created by the normal approximation. Owing to this factor, as well as to the smoother interpolation of extreme outliers' p-values, the probability estimates from this normal approximation outperform the ecdf ones.

For the second simplification, p-values are abandoned in favor of z-scores, drawn from the normal model. The scale of z-scores more clearly reflects the magnitude of extreme outliers and allows a more intuitive interpretation of accuracy thresholds in our map. Furthermore, the p-values calculated using the normal distribution are not meaningful given the heuristic use of the normal distribution for smoothing. Thus, the final form of the likelihood estimate becomes $Z_{ij}=\sqrt{Z_i^2+Z_j^2}$, where $Z_i$ and $Z_j$ are the z-scores of $MI_{ij}$ from the marginal distributions, and $f(Z_{ij})$ is the joint likelihood measure.

Scores that are significantly higher than background mutual information values are indicated where one or more of the following is true: 1) The p-value of a particular interaction's score is equal to or lower than a user-defined acceptability threshold, e.g. <0.2, or <0.1, or <0.05; 2) p-values are converted to a False Discovery Rate, FDR, and the score for an interaction is equal to or lower than a user-defined acceptability threshold of the FDR, e.g. <20%, <10%, or <5%; or 3) The z-score computed by comparing a MI interaction score to its background exceeds a user-defined acceptability threshold, e.g. >5, >6 or >7. The p-value of a particular interaction's MI score is equal to the probability of a MI score occurring by chance, where chance is determined from the MI background distribution.

Figure 12:
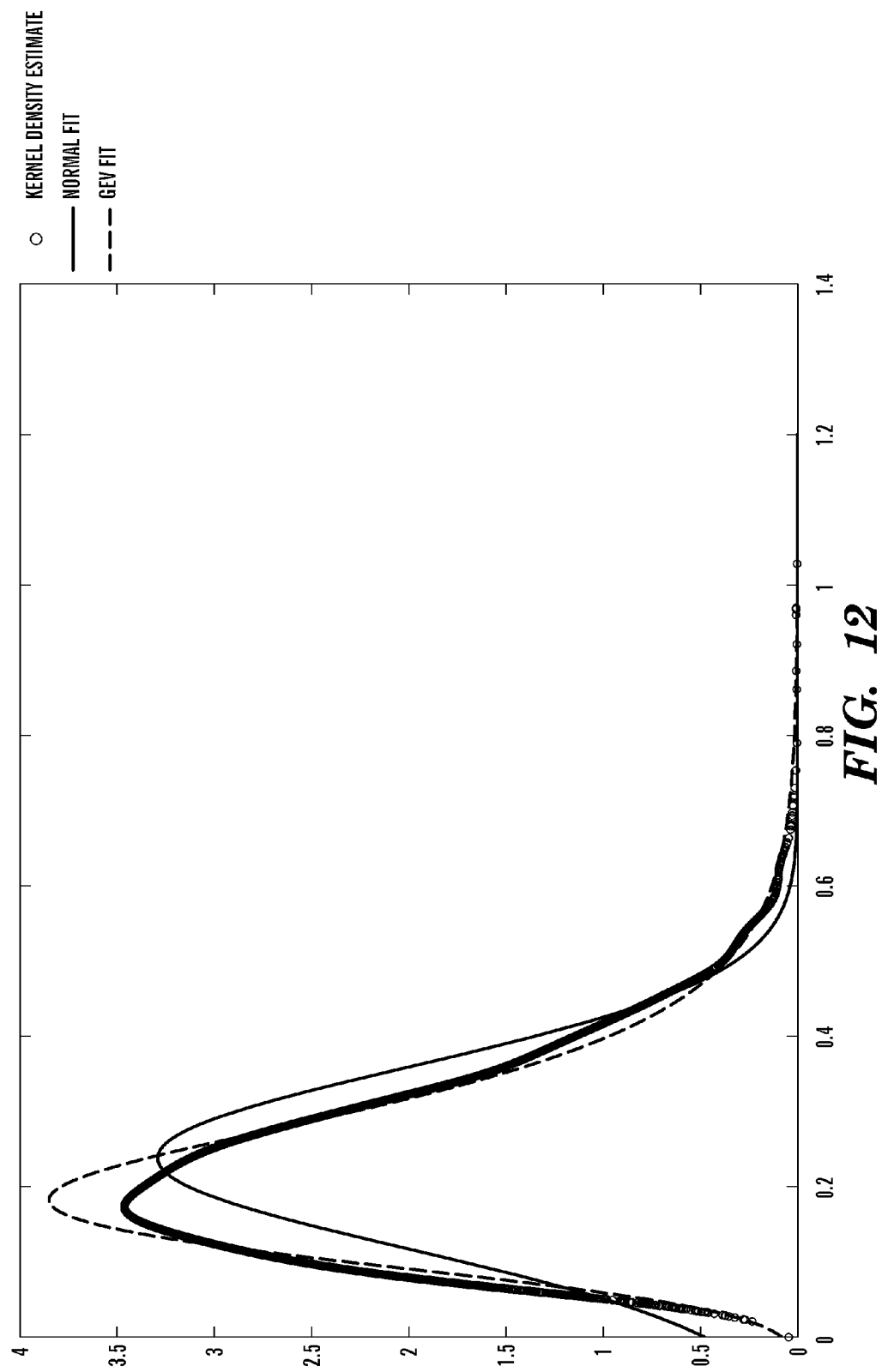
FIG. 12 shows estimates of the distribution of mutual information. The distribution of mutual information for both genes of a potential regulatory interaction is used to estimate the significance of mutual information. The distribution of mutual information for one gene lexA illustrates different types of fit. Normal fit, while not the best approximation to the empirical distribution, penalizes the distal network neighborhood.

Other approximations of the background MI distribution have been evaluated, including the tail-heavy distributions such as the generalized extreme-value (GEV) distribution and the Rayleigh distribution, always achieving similar results and sacrificing speed of execution for the more expensive distribution fits. The smoothed empirical (Kernel Density estimate), extreme-value, and normal distributions of the mutual information values for one gene are shown in FIG. 12.

The method of estimating the likelihood of mutual information differs from the conventional ways of estimation, for example by shuffling[84] or by Roulston metric of significance[85]. Both of these prior methods calculate the statistical significance given a random model of the interaction in question. In contrast, the inventive method calculates the likelihood of mutual information given the observed network context.

CLR provides a robust level of performance with sparse, noisy data. In part, its performance is boosted by the implicit assumption that regulatory networks are sparsely connected, an assumption that is supported by many studies of regulatory network connectivity[83]. In practice this means that the algorithm will have difficulty identifying the targets of transcription factors that regulate more than ~100 genes. Since few transcription factors regulate more than 100 genes, this assumption will have little impact on the discovery of most regulator targets. However, CLR does relatively little to elucidate the targets of super-regulators, such as the sigma factor RpoD, which regulate many hundreds to thousands of genes. Moreover, the weak signal-to-noise ratio offered by these super-regulators is difficult to overcome with any algorithm. This limitation does not affect hub transcription factors that regulate many genes, like fliA for which CLR finds over 50 targets.

CLR also cannot distinguish biological regulation from false correlation when the biological regulation is masked by the weak signal of the correct regulator. For example, the majority of the FecI transcription factor's predicted targets are known targets of the Fur transcription factor, which shows little correlation to its known targets in the compendium. FecI, however, is strongly correlated with its own targets and many other iron genes. The chromatin immunoprecipitation (ChIP; see below) results suggest that these predicted interactions of FecI to the other iron genes, besides its known target of fecA, are false correlations and not expression changes caused by FecI binding to the promoters of these additional iron genes. The problem in this situation is the lack of mRNA expression changes for Fur in the compendium. Thus, the algorithm cannot identify the targets of Fur based on mRNA expression alone. The reason Fur mRNA expression does not vary with its target may be that Fur is regulated primarily through post-translational allosteric changes induced by iron binding which do not eventually manifest themselves in the changes in Fur mRNA or that the expression levels for Fur are below the sensitivity of the microarray[70]. Alternatively, the errors in identifying Fur targets may simply be due to inadequate sampling of iron-related conditions in our compendium. This is not surprising given that the compendium used in this instance contains only 60 phenotypically distinct profiles (see Examples, below). Such errors will be corrected as the size and diversity of the compendium increases.

Although most microbial transcription factors, like Fur, exhibit some modulation of transcription, there may be some regulators that are essentially expressed constitutively. Modulation of such factors may occur only post-transcriptionally. The targets of such regulators cannot be detected by any algorithm that relies on microarray expression profiles alone[62]. The analysis of existing regulatory pathways suggests that such cases of constitutive expression in microbes are rare; there is nearly always some transcriptional regulation, often through direct or indirect feedback loops or at the level of sigma factor modulation. Nevertheless, detecting the targets of such constitutively transcribed regulators will require an alternative approach based on mass spectrometry, chromatin immunoprecipitation, or synthetic modulation of the regulators.

Finally, CLR relies on accurate annotation of transcription factors to determine what genes to define as regulators in the network. Transcription factor identification by sequence analysis is a mature problem in bioinformatics. Existing algorithms generate these lists with high sensitivity; any further improvements in the accuracy of the list would be expected to improve the inferred transcriptional regulatory map as well.

Compendia of Biochemical Expression Measurements

Assemblies or compendia of biochemical expression measurements of use in the methods described herein can take a number of forms. In a preferred embodiment, the compendium includes data derived from probing a microarray with nucleic acids representing different states or conditions for the microbe of interest. In general, the more varied the conditions represented in the compendium the more useful the compendium is for generating a detailed regulatory interaction map. The biochemical expression measurements are preferably from a microorganism, including, e.g., prokaryotic and eukaryotic microorganisms.

While microarray data are preferred for compendia as described herein, biochemical expression data can be derived in other ways. For example, expression profiling can be achieved by Northern blotting, or, for example, by the methods described in U.S. patent application publication No. 20070059715, titled "Quantitative gene expression profiling, "U.S. patent application publication No. 20070037189, titled "Methods for amplification monitoring and gene expression profiling, involving real time amplification reaction sampling", and U.S. patent application publication No. 20060105380, titled "Methods and systems for dynamic gene expression profiling," each of which is incorporated herein by reference.

Other methods are available to examine gene expression on a wide scale and thus, to generate data for a compendium of biochemical expression data of use in the methods described herein. These approaches are variously referred to as RNA profiling, differential display, etc. For example, SAGE (see, e.g. U.S. Pat. Nos. 5,695,937 and 5,866,330) provides a method that allows for quantitative monitoring of global gene expression. Gel-based methods (described, e.g., in U.S. Pat. Nos. 5,871,697, 5,459,037, 5,712,126 and PCT publication WO 98/51789) can also be used to generate the compendium of expression data. U.S. Pat. No. 5,459,037 describes a method based on capturing the 3'-end fragments of cDNAs. PCT publication WO 98/51789 describes another method that utilizes a PCR based profiling approach.

Regulatory network inference with microarrays requires a dataset where genes and transcription factors are perturbed strongly and frequently enough to enable detection of true regulatory relationships above the background of microarray noise and biological variability. In the Examples described herein below, raw Affymetrix CEL files were collected for 179 microarrays from nine different publications (FIG. 1 and Table 1). These microarrays assayed 68 conditions including pH changes, growth phases, antibiotics, heat shock, different media, varying oxygen concentrations, numerous genetic perturbations, several carbon sources, and nitrate. They provide a diverse collection of perturbations in many important pathways in E. coli.

To explore pathways of particular importance to antibiotic resistance, the Example described herein below assayed an additional 121 conditions using 266 microarrays, including more than 50 genetic perturbations (overexpression or knockout) during norfloxacin-induced DNA damage response, overexpression of the ccdB toxin, and growth to stationary phase on low and high glucose. The microarrays were combined into a compendium of 445 microarrays covering 189 conditions (FIG. 1). The compendium was uniformly normalized using MASS, DChip perfect-match, RMA, and GCRMA normalization algorithms. All raw and normalized data are stored in M3D, a publicly accessible microarray database and visualization tool, which can be accessed at m3d.bu.edu. This compendium served as the input for our CLR algorithm (FIG. 1) as well as three additional network inference algorithms that were tested on the data set. Similar normalization procedures can be applied to data generated and collected in other ways by one of skill in the art.

Measurement and Validation of Algorithm Performance

The performance of the CLR algorithm can be validated in any given application in several ways. One approach is to compare the predicted regulatory interaction results with known interactions from that organism. The extent to which the CLR approach predicts interactions that are known to be real interactions provides a measure of the reliability of the approach in any given application. Thus, the accuracy and sensitivity of inferred networks is computed by comparing the inferred network to a reference network. Accuracy is the fraction of predicted interactions that are correct $$\left(\frac{TP}{TP+FP}\right),$$

and sensitivity is the fraction of all known interactions that are discovered by the algorithm $$\left(\frac{TP}{TP+FN}\right),$$

where TP is the number of true positives, FP is the number of false positives, and FN is the number of false negatives. Accuracy and sensitivity are computed over a range of pruning thresholds; interactions with scores below the pruning threshold are removed from the inferred network. Both accuracy and sensitivity are reported as percentages.

Another approach is to physically test the predicted interactions using, e.g., chromatin immunoprecipitation with quantitative PCR. Chromatin immunoprecipitation is performed, for example, according to the methods described by Lin and Grossman, 1998, Cell 92: 675-685, or as described in the Examples herein below. The chromatin immunoprecipitation approach permits the verification of a set of interactions identified by the algorithm that thereby add new experimentally validated edges to a known set of regulatory interactions.

A third approach uses the mature tools of sequence analysis, and permits the discovery of new regulatory motifs in the promoters of the regulated genes. An example of this approach is set out in detail in the Examples herein below.

EXAMPLES

To test the CLR algorithm for use in methods of discovering regulatory interactions, the extensive knowledge of transcriptional regulation in *Escherichia coli* has been exploited to rigorously assess the performance of the CLR algorithm on a genome scale. In *E. coli*, a set of over 3200 reliable regulatory interactions among 1211 genes have been curated in the RegulonDB database[27] which can be used for performance assessment.

A compendium has been collected and assembled comprising 445 new and previously published *E. coli* Affymetrix Antisense2 microarray expression profiles, collected under various conditions including pH changes, growth phases, antibiotics, heat shock, different media, varying oxygen concentrations, and numerous genetic perturbations (FIG. 1 and Table 1). CLR was applied to the compendium to compute a preliminary map of *E. coli* transcriptional regulation across the entire genome.

The CLR algorithm inferred over 200 existing interactions with 80% accuracy, predicted more than 200 new interactions, many of which were experimentally confirmed, and discovered an unexpected regulatory link between central metabolism and the regulation of iron import into the cell. These results demonstrate that this approach permits the systematic mapping of transcriptional regulation in microbes using phenotypically diverse gene expression profiles that are collected in a "shotgun" approach akin to genome sequencing.

Experimental Procedures

Experimental procedures of use in the methods disclosed herein and described in the following Examples include the following.

Bacterial Strains, Growth Conditions, and Microarray Profiling

Fifty-three E. coli genes of interest were overexpressed in E. coli strain MG1655 using a modified pBAD30 vector, pBADx53[46]. pBADx53 has a low copy SC101 origin of replication, does not contain araC, and yields low and consistent levels of expression, generally increasing gene expression 2 to 10 fold above native expression levels. The 53 genes were PCR amplified from MG1655 genomic DNA. A ribosomal binding site was included at the start of the forward primer. The cloned genes were transformed into strain MG1655. Gene deletions were constructed from E. coli strain MG1655 by replacing the coding sequence from start codon to stop codon[47]. Gene deletion strains and overexpression plasmids were confirmed by DNA sequencing.

Steady-State Experiments

Gene deletion strains and pBADx53 overexpression strains were grown in 96 square-well plates containing 1.6 ml LB (Miller). LB media for the overexpression strains contained 0.125% arabinose to induce cloned gene expression and appropriate antibiotics to maintain the plasmid. Plates were incubated at 37° C. with shaking at 300 rpm. DNA damage responses were induced by growing perturbation strains for 3 hours in Norfloxacin (25 to 100 ng/ml). Cells were harvested when the O.D. 600 for the cultures was between 0.25 and 0.4.

Time-Course Experiments

For an antibiotic time-course experiment, cultures were grown in 250 ml flasks at 37° C. with shaking at 250 rpm. Each culture was grown in 75 ml of LB to 0.4 OD600. DNA damage was induced with 10 μg/ml of Norfloxacin. Samples were taken before and 12, 24, 36, and 60 min after addition of Norfloxacin. For the glucose time series, E. coli EMG2 were diluted 1:1000 into 150 ml LB (Miller) in 1 L baffled flasks supplemented with 0.2% or 0.4% glucose. Samples were taken 2.5, 3, 3.5, 4, 4.5, 5, 5.5, 6, and 8 hours post-incubation. To examine the effect of overexpression of the F-plasmid encoded toxin CcdB, we employed a plasmid-borne riboregulation system that enables precise control of gene expression through highly specific RNA-RNA interactions[48]. A riboregulation system overexpressing LacZ was included as a control. Cells were diluted 1:1000 in 50 ml LB (Miller) with appropriate antibiotics to maintain the plasmid. Samples were taken immediately before induction and then 30, 60, and 90 min after induction of CcdB or LacZ expression.

Preparation of RNA and Hybridization

RNA was prepared using Qiagen RNeasy kits. For time-course experiments, cultures were immediately added to 2 volumes of Qiagen RNAprotect reagent. For steady-state experiments, 1.5 ml cultures in multiwell plates were centrifuged at 3000 g for 5 min at 4° C. Media was poured off and 500 μl of RNA protect was then immediately added to each cell pellet. cDNA was prepared and hybridized to the Affymetrix Antisense2 microarrays according to the standard Affymetrix prokaryotic sample and array processing protocol.

External Data

A literature search was performed to locate microarray datasets to expand the phenotypic diversity of the compendium. Preference was given to larger datasets (>10 chips). Data were collected from nine publications containing a variety of media, environmental changes (pH, DNA damaging drugs), and growth stages. The data sets in the compendium are summarized in Table 1.

Microarray Normalization

Raw probe intensities were normalized to gene expression levels using MASS (Affymetrix), RMA (Irizarry, Bolstad et al. 2003), GCRMA[49], and Dchip PM (Li and Wong 2001). All methods were run using the default parameters. For GCRMA, the ad hoc algorithm was used instead of the full empirical Bayes method due to memory constraints from the large dataset. In the inventors' experience, RMA was the single best normalization method of the four that were tried, and the results presented herein for CLR use this normalization.

The performance of two of the algorithms used for comparison with CLR, the ARACNe and the Bayes Nets variant algorithms, improved if the algorithms were applied four times, each time using the compendium data normalized with a different one of the four normalization methods, and then averaged the resulting four networks. This averaging approach did not improve results for Relevance Networks or CLR, but may prove useful in other data analysis contexts.

Construction of the Reference Set of Interactions

All known regulatory interactions catalogued in RegulonDB version 4[27], which can be accessed at regulondb.ccg.unam.mx/html/Data_Sets.jsp, were obtained for use with the CLA approach described herein. Two-percent of the interactions could not be matched to probe sets on the expression array leaving 3293 interactions among 1211 genes as the reference network. We also obtained a list of regulatory genes from RegulonDB, providing 332 putative and known transcription factors.

Data Availability

The 212 Affymetrix CEL files generated from our own experiments have been submitted to GEO, the NCBI microarray database. Raw and normalized data for all 445 microarrays are available at the Many Microbe Microarrays database ($M^{3D}$ http://m3d.bu.edu). $M^{3D}$ provides a web interface for visualizing heat plots, histograms, and scatterplots for any subset of the genes and experiments in the compendium using any of the four normalization methods mentioned above.

Network Inference Algorithms

Several existing methods suitable for whole-genome network mapping from expression data were adapted. These methods were Relevance Networks[63], ARACNe[64], and Bayes Nets[65]. In addition, the novel, Context Likelihood of Relatedness method was developed, which constitutes a background-corrected approach to Relevance Networks. For Relevance Networks, ARACNe and CLR, a B-spline smoothing and discretization method was used to compute mutual information method[84]. We provide our own Matlab interface to the Daub et al. B-spline mutual information estimation code library is provided and can be assessed at gardnerlab.b-u.edu. All mutual information values were computed using 10 bins and $3^{rd}$ order B-splines. The Relevance Networks, ARACNe and Bayesian Networks are described below.

Relevance Networks

A Relevance Network algorithm identifies a potential biological association as any regulator-target gene pair with a mutual information score above a particular threshold selected by the user. Although originally intended as a form of clustering, the algorithm was applied in the approaches described herein to network inference by removing all associations not involving at least one transcription factor. The original Relevance Networks algorithm generated one network at one threshold. For the algorithm comparison, a range of thresholds was applied to measure the algorithm's performance across a range of sensitivities. The Relevance Network algorithm, unlike CLR and ARACNe, was not robust to the quality of the mutual information estimator and required the use of the B-spline estimator to produce reliable results.

ARACNe

For the comparisons described herein, a modified implementation of the ARACNe algorithm[84] was created. This implementation used the B-spline method to estimate mutual information and incorporated a probabilistic threshold into the algorithm. In the original ARACNe algorithm, an edge is pruned when it falls outside of the tolerance threshold of every interaction triangle. This approach failed around certain hub regulators, decreasing its performance on the microbial compendium. In addition, the original ARACNe algorithm did not produce confidence estimates for every interaction, making it difficult to adjust the accuracy and coverage of the network. Instead of the original pruning method, the frequencies of keeping each edge based on all of the comparisons in which it participated were computed. Knowledge of transcription factor identity was also used to constrain ARACNe in the same way as for the CLR algorithm; namely, the full network was computed first and then all interactions that did not involve at least one transcription factor were eliminated. Applying the transcription factor constraint prior to applying the ARACNe algorithm produced less accurate and sensitive network maps. Finally, the full mutual information matrix was computed using every probe set (as also done for CLR), including the intergenic regions, in order to make probabilistic scores using as large a distribution as possible. Intergenic regions were pruned from the network map once the mutual information matrix was computed.

Bayesian Networks

Unlike the algorithms described herein that prune away edges from a completely connected graph, Bayesian networks exhaustively or heuristically search through the space of possible graphs (i.e., regulatory networks) scoring each and keeping either the best scoring network or a network constructed by averaging over all the searched graphs and weighting them by their score. The inventors initially tested the implementation of the module networks algorithm previously applied to yeast[86], but had more success on the compendium of bacterial expression profiles using traditional Bayesian networks.

For computational tractability, every gene was restricted to having at most two regulators and interactions were only allowed between transcription factors and genes. Several scoring functions were tested for the algorithm: discrete (two-state, genes are OFF or ON), linear, logistic, polynomial approximation, and hill function. Scores for the linear function were estimated with linear least-squares. Scores for non-linear functions were estimated with nonlinear least-squares using the Levenberg-Marquardt algorithm. All scores were adjusted for the number of parameters using Bayesian Information Criterion (BIC). Of the tested scoring methods, the linear function offered the best balance between speed and quality of reconstruction.

A model averaging procedure was used to score the likelihood of each edge in the regulatory network, allowing the user to choose a threshold for the desired accuracy and sensitivity, as was done for the mutual information based algorithms. Transcription factor/gene interactions were scored as follows. For a particular gene $A_i$ in a regulatory network allowing only one regulator per gene, the likelihood of being regulated by a given transcription factor $B_j$ would be calculated as $$\frac{score(A_i \mid B_j)}{\sum_k score(A_i \mid B_k)}$$

where k is indexed over all identified transcription factors. This function was generalized to the case of two transcription factors. Transcription factor/transcription factor interactions were initially scored using a different approach. Directed acyclic graphs (DAG) of the transcription factor only network were sampled using Markov Chain Monte Carlo. The formula above was then applied for the sampled networks. However, it was found that in practice both the speed and accuracy of the algorithm improved if the transcription factors were scored in the same way as for transcription factor/gene interactions. This resulted in networks that were no longer DAGs, and thus the algorithm was no longer a true Bayesian network.

Measurement of Algorithm Performance

Performance of all network inference algorithms was measured as described herein. For the Bayes network variant, transcription factor annotation was applied a priori. For all other methods the annotations were used for pruning following network inference.

Functional Enrichment

Gene functional annotations and ontology hierarchies were obtained from EcoCyc (annotations were from Gene Ontology Consortium, Enzyme Commission (EC), and other ontologies). All ancestors of each term associated with a particular gene were included. Enrichment was determined with a hypergeometric distribution by calculating the p-value of the given number of hits for each term based on the query size, the number of genes in the genome, the number of genes in the query with the given association and the number of genes in the genome sharing that association. To ensure that single gene hits would not provide enrichment to rare categories, at least two genes were required in a query set to map to the same term.

Motif Detection

For motif discovery, the network was first pruned at the 60% confidence threshold. The target genes of each transcription factor were grouped into operons using the known and putative operons in RegulonDB[20]. To attain the statistical significance necessary for sequence alignment, only transcription factors regulating at least five operons were included. Multiple alignments of the promoter regions using the MEME multiple alignment system version 3.5.0[7] constrained to find one motif with any number of repetitions on the same strand. The operon, predicted operon, and transcription start site annotation were obtained from the RegulonDB website. Having obtained the transcription start site, 150 by upstream of this site was taken to be the promoter. When another gene was found less than 150 by upstream of the transcription start site, the promoter length was truncated to the end of the preceding gene. A background model was built using tri-nucleotide frequencies from all promoter regions. This model was supplied to MEME as the background model for estimating the likelihood of motif occurrence. MEME was constrained to find any number of repetitions of one motif, occurring on the same strand within each promoter. Motif width and other settings were left to default values.

To further assess the significance of each motif, the nucleotides of every promoter were shuffled 100 times and MEME was run on each shuffled dataset, measuring the e-value of the top motif. These e-values follow a near-normal distribution, skewed by the difference between the common true motif nucleotide distribution and the background distribution. The quality of the "true" motif was approximated as the z-score of that motifs e-value from the normal fit of the shuffle model.

Example 1

Constructing an *E. coli* Compendium

Regulatory network inference with microarrays or other expression profiles known to hose of skill in the art requires a dataset where genes and transcription factors are perturbed strongly and frequently enough to enable detection of true regulatory relationships above the background of microarray noise and biological variability. Raw Affymetrix CEL files were collected for 179 microarrays from nine different publications (FIG. 1 and Table 1). These microarrays assayed 68 conditions including pH changes, growth phases, antibiotics, heat shock, different media, varying oxygen concentrations, numerous genetic perturbations, several carbon sources, and nitrate. They provide a diverse collection of perturbations in many important pathways in E. coli.

To explore pathways of particular importance to antibiotic resistance, an additional 121 conditions were assayed using 266 microarrays, including more than 50 genetic perturbations (overexpression or knockout) during norfloxacin-induced DNA damage response, overexpression of the ccdB toxin, and growth to stationary phase on low and high glucose. The microarrays were combined into a compendium of 445 microarrays covering 189 conditions (FIG. 1). The compendium was uniformly normalized using MASS, DChip perfect-match, RMA, and GCRMA normalization algorithms. All raw and normalized data are stored in $M^{3D}$, a publicly accessible microarray database and visualization tool, which can be assessed at m3d.bu.edu. This compendium served as the input for the CLR algorithm (FIG. 1) as well as three additional network inference algorithms that were tested on the data set.

Example 2

Verification of Array Data Normalization and Consistency

Figure 2A:
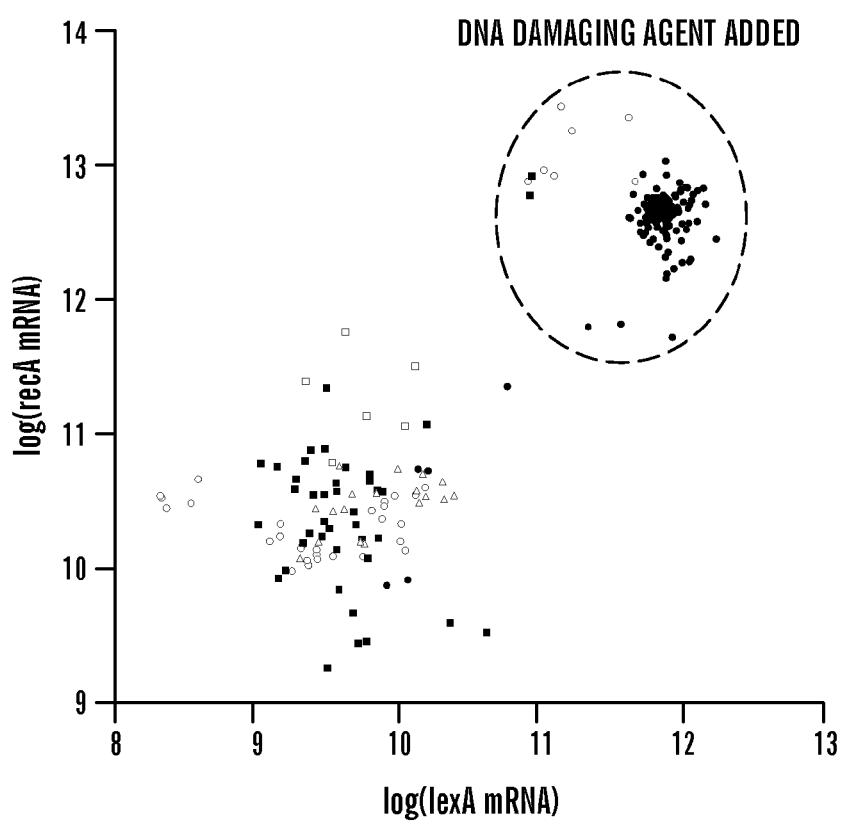
FIG. 2 shows examples of typical covariation in expression between a transcription factor and its target gene. (A) Two key players in the SOS response, RecA and its regulatory protein LexA, are both highly expressed in the presence of a DNA damaging agent regardless of the laboratory or experimenter running the microarray. The shapes for each point in (A) and (B) correspond to the experimenter. For data from other laboratories, the first author of the associated publication was used. For data from our laboratories, the experimenter name is italicized. (B) Two genes involved in arabinose metabolism, araA and its regulator AraC, behave as a switch that is ON when arabinose is present in the media and OFF otherwise. (C) Confounding experiments and uneven sampling can lead to false correlations (inset) that network inference algorithms aim to eliminate. Addition of the correct condition (in this case, expression profiles on minimal media) clears the relationship. (D) The relationship between the Lrp transcription factor and its known target serA becomes more pronounced upon addition of the minimal media expression profiles in which both genes are highly active.
Figure 2B:
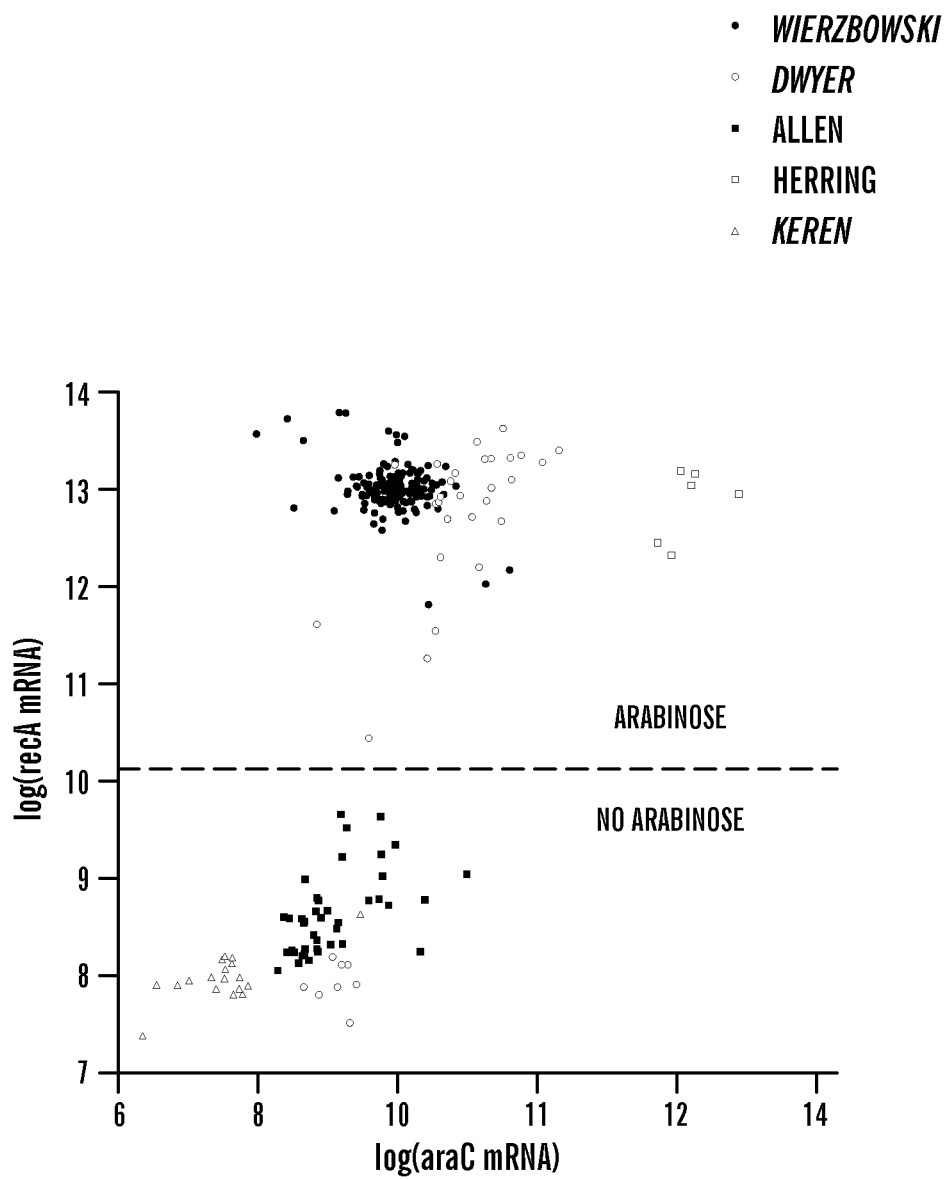
Figure 2C:
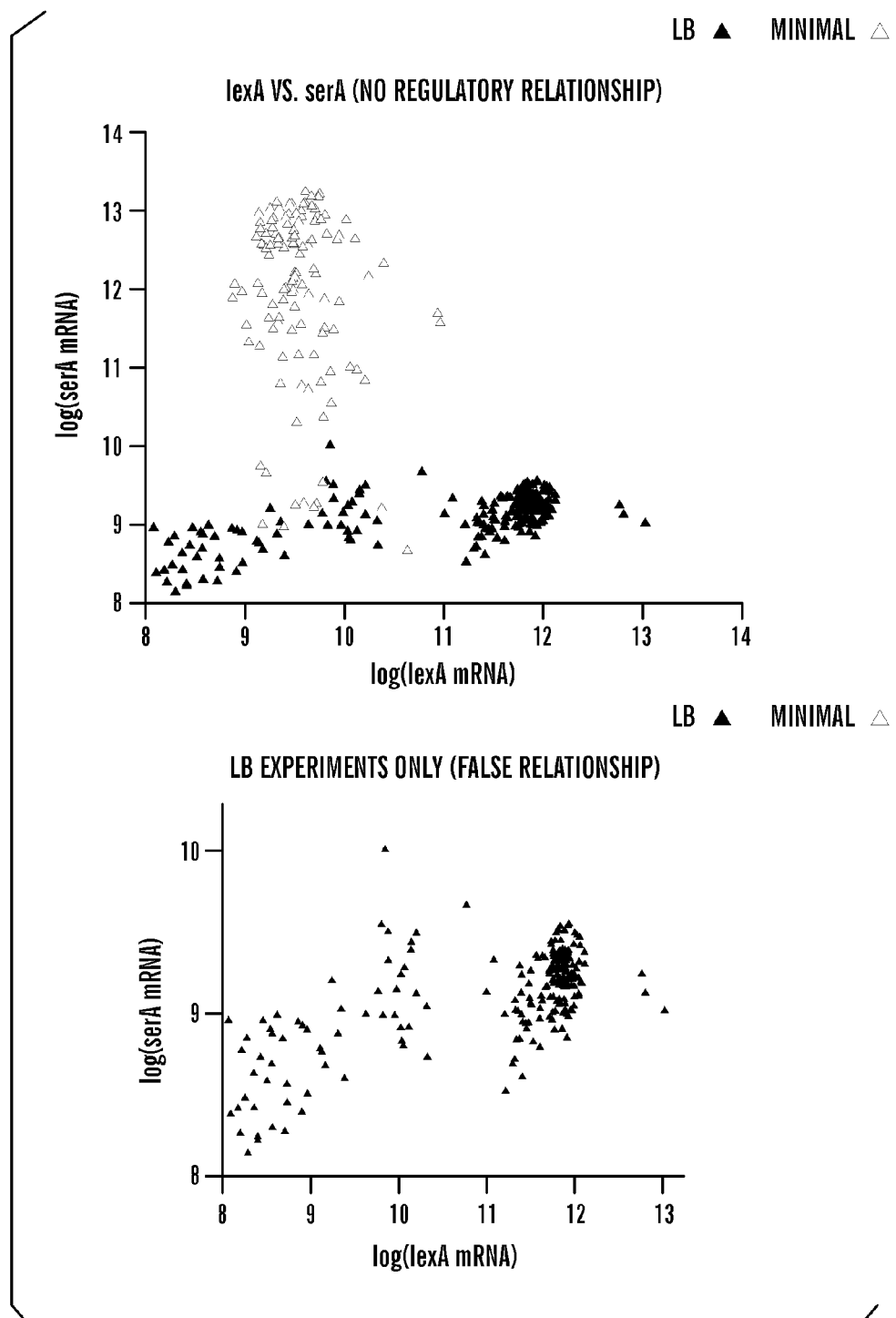
Figure 2D:
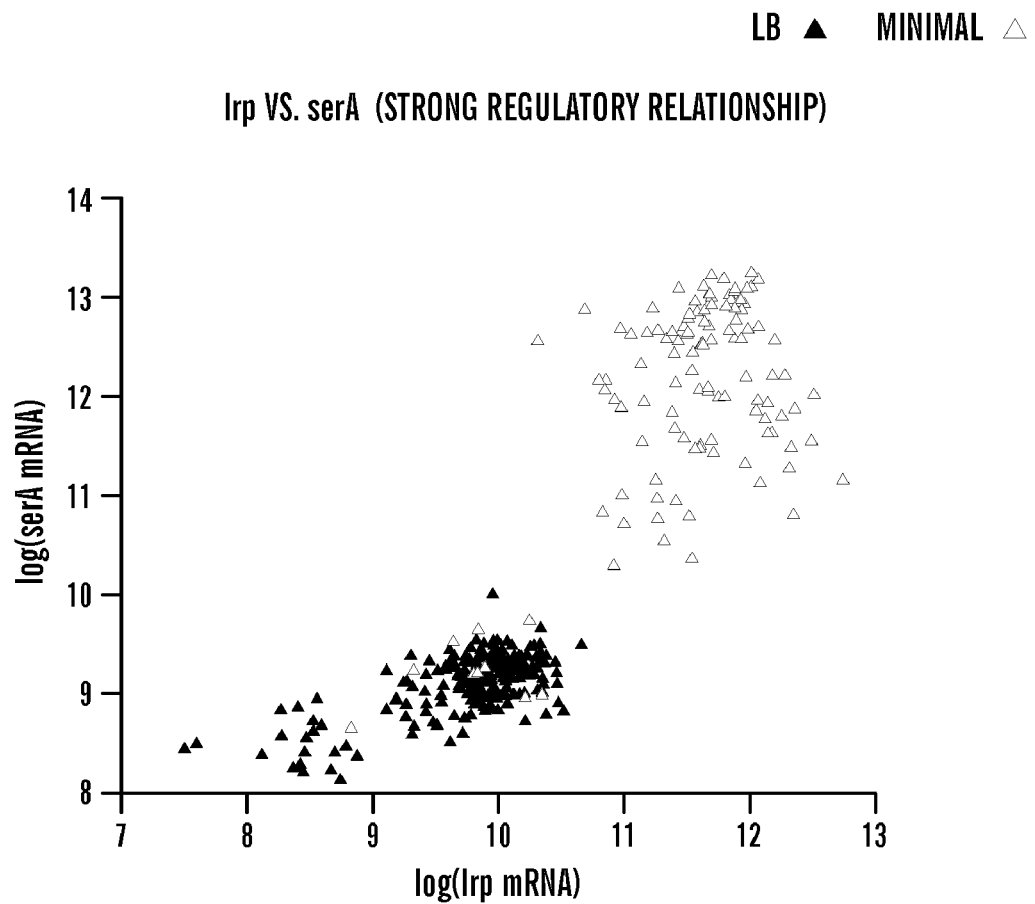

Regulatory network inference algorithms identify regulatory interactions by detecting causal influences between genes. FIGS. 2a, 2b, and 2d show relationships between different transcription factors and their known targets that are characteristic of the data in the E. coli microarray compendium described herein. The wide range of expression levels for the genes presented in FIG. 2 result from the cell's response to the different environmental and genetic perturbations assayed in the compendium. In each plot, the expression level of the regulated gene increases with the expression level of its regulator. For example, FIG. 2a shows the expression levels of recA, an important gene involved in the SOS-response to DNA damage, and of lexA, the primary transcription factor of the SOS-response[61]; each gene is highly expressed only when a DNA-damaging agent is present in the growth media. A similar situation occurs for the switch-like arabinose-induced response shown in FIG. 2b. These coordinated expression responses in the compendium are observed regardless of the laboratory or individual running the experiment—verifying the consistency of the array platform and normalization procedure.

Example 3

Validation of CLR Algorithm Performance

Before exploring the regulatory networks inferred by the CLR algorithm, the algorithm's performance was validated using a multilevel validation approach (FIG. 1). First, the performance of CLR was tested on the genome scale using the RegulonDB set of transcriptional regulatory interactions. Second, ChIP experiments were performed to verify an additional set of interactions identified by the algorithm and thereby add new experimentally validated edges to the known set of E. coli regulatory interactions. The mature tools of sequence analysis provided a third level of validation, and allowed the discovery of new regulatory motifs in the promoters of the regulated genes.

RegulonDB Testing

Figure 3B:
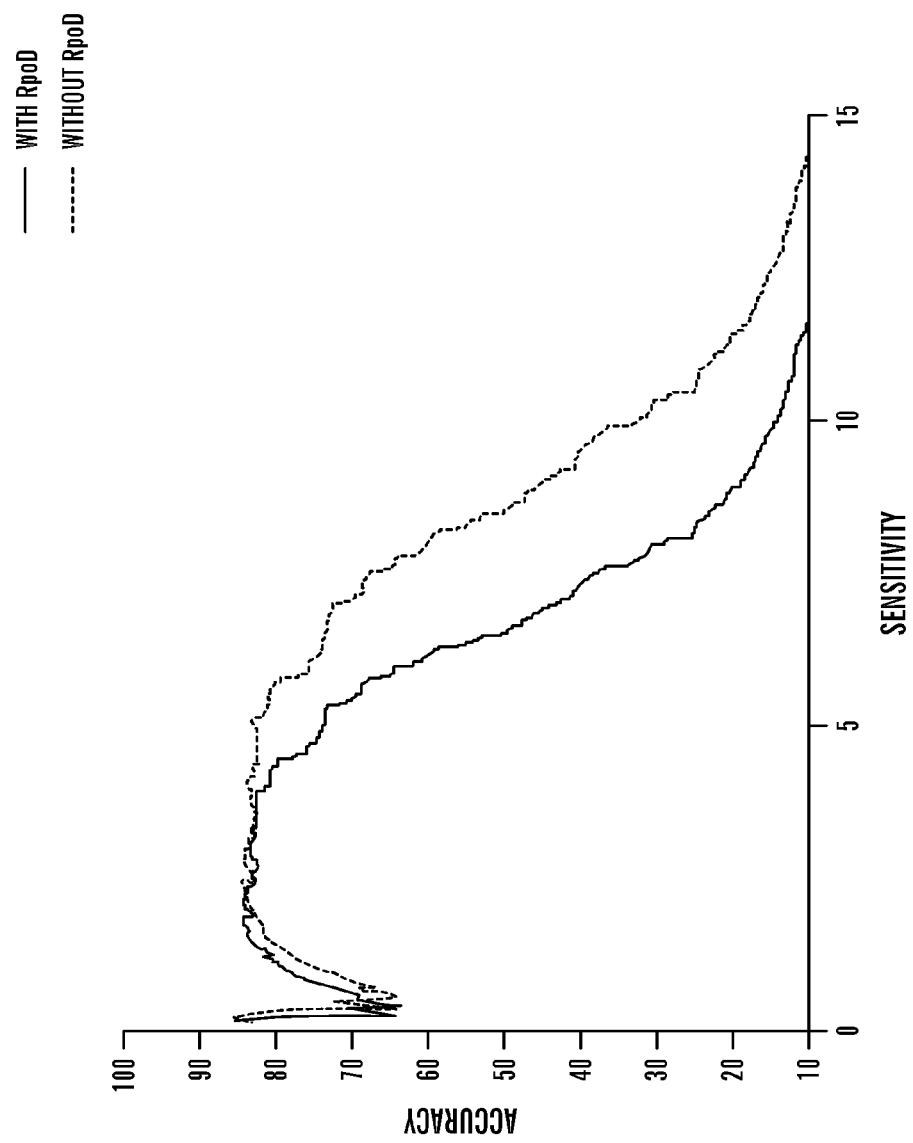

The CLR algorithm was applied to all 4345 genes on the E. coli Antisense 2 microarray using the 445 profiles in the compendium taken from the $M^{3D}$ database. Interactions were only allowed from 332 known or predicted transcription factors to any of the 4345 genes, permitting clear biological interpretation and validation of the predictions. To score our results, predicted interactions were compared with the set of 3293 interactions in the RegulonDB database[27]. Two measures were computed: sensitivity, which is the fraction of the 3293 known E. coli interactions that CLR successfully identified; and accuracy, which is the fraction of identified interactions that are true positives (FIG. 3b). RegulonDB contains regulatory information for only about one-fourth of the genes in the E. coli genome and about one-half of the transcription factors, but the number of interactions is large enough to make sound estimates of algorithm performance in genome-scale applications.

With 80% accuracy, CLR recovers 201 regulatory interactions among genes included in RegulonDB (FIG. 7, solid bold line edges and solid thin line edges). When interactions identified among genes outside the annotated subset in RegulonDB are included, an additional 228 novel interactions are found, for a total of 429 inferred interactions in the regulatory map (FIG. 7, all edges) at the 80% accuracy threshold. These accuracy scores are likely underestimates of the true values due to the incompleteness of RegulonDB. For example, the ChIP results indicate that the 60% accuracy score estimated for the CLR algorithm based on RegulonDB is, in reality, more likely a 70% accuracy score, as many of the novel interactions that CLR captures are incorrectly labeled false positives when using RegulonDB alone (see next section for details). In addition, the targets of many transcription factors in this network are significantly enriched for one or more biological functions (FIG. 5), and the enriched biological functions reflect the conditions screened in the microarray compendium.

Figure 3C:
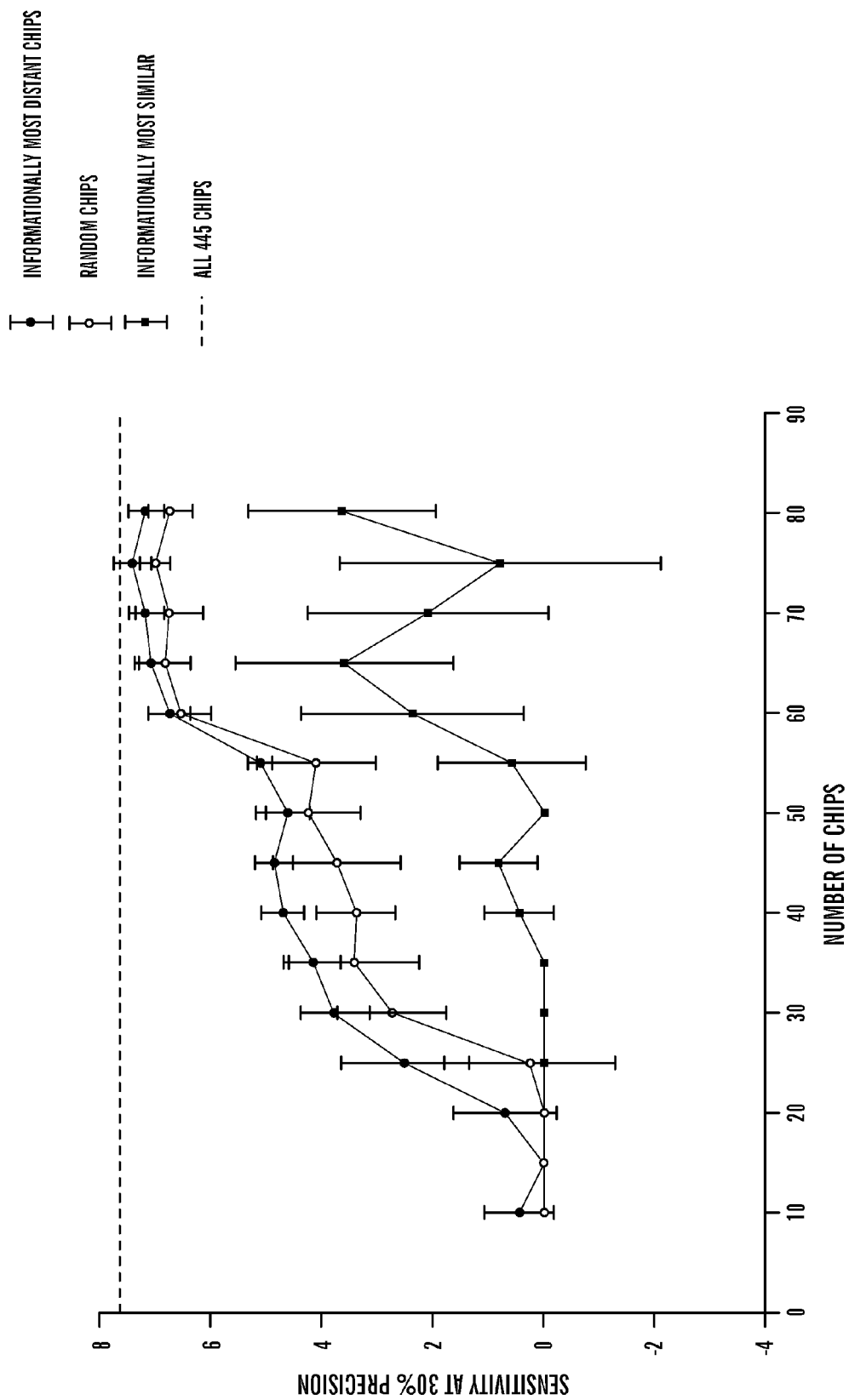

Although hundreds of known regulatory interactions were identified correctly at high accuracy, this represents only a fraction of known interactions in E. coli. The absolute sensitivity of the algorithm depends on several factors including the number and diversity of expression profiles. As discussed herein below, the CLR algorithm can achieve maximum sensitivity and accuracy using a subset of only 60 expression profiles selected for maximum diversity (FIG. 3c). Most of the profiles in the compendium contribute redundant information about gene expression responses and regulatory interactions. Thus, the sensitivity achieved by the CLR algorithm appears to be limited largely by the low phenotypic diversity of the data set. In addition, the sensitivity estimates reported in FIG. 3b are adversely biased by the heavy representation of several ubiquitously connected regulators in RegulonDB. In fact, the principal adverse impact to the reported sensitivity comes from a single sigma factor, RpoD ($\sigma^{70}$), the primary RNA polymerase sigma subunit in E. coli. This single sigma factor accounts for 780 (24%) of the interactions involving 64% of the genes in RegulonDB. Removing rpoD from the reference set of interactions increases CLR's reported sensitivity to around 10% while retaining the same high accuracy (FIG. 3b).

The CLR algorithm does not detect much of RpoD' subiquitous connectivity because RpoD shows only weak mutual information with its targets. This is likely due in part to inadequate stimulation of RpoD activity in the conditions sampled in the compendium. In addition, the CLR algorithm assumes moderate sparsity in the biological connectivity of most genes. Such an assumption is appropriate for the great majority of transcription factors and other regulators in biological networks[31]. Use of this assumption improves the global performance of the CLR algorithm, but it also means the algorithm will have difficulty finding all the targets for rare cases of highly connected regulators, such as RpoD. Attempting to capture all of the targets of such a promiscuous regulator results in unacceptably low accuracy for the rest of the transcription factors in the network.

Chromatin Immunoprecipitation

Transcription factors assayed by ChIP-PCR were cloned into TOPO (Invitrogen) IPTG inducible vectors containing an Xpress™ epitope. The plasmid was transformed into E. coli strain MG1655 and verified by DNA sequencing.

Transcription factor:DNA complexes were immunoprecipitated using a modification of the protocols of Lin and Grossman[51] and Upstate (http://www.upstate.com/). Six replicates were performed for each transcription factor. Cells were diluted 1:100 from overnight cultures into 50 ml of LB with 0.5% glucose in a 250 ml flask and grown to an OD600 of around 0.5. A 15 ml sample was taken from each flask and 400 µl of 37% formaldehyde was added (final concentration 1%). Protein:DNA constructs were cross-linked for 10 minutes at room temperature followed by two washes in ice-cold PBS.

Cells were lysed by incubating samples at 37° C. for 30 minutes in 500 µl of lysis buffer (10 mM Tris, 50 mM NaCl, 10 mM EDTA, 20% sucrose, and 4800 units of freshly added Epicenter Ready-lyse lysozyme), followed by addition of 500 µl of 2×IP buffer (200 mM Tris, 600 mM NaCl, 4% Triton X-100, 1 mM fresh PMSF, and 4 µg/ml RNase Cocktail [Ambion]) and incubation for 10 minutes at 37° C. with shaking. Lysates were sonicated 4×30 seconds with a Branson sonicator on 20% percent power to shear DNA to an average size of 500 bp.

A 100 µl sample of the sheared lysate was removed, crosslinks were reversed, and the sheared DNA was purified by phenol:chloroform extraction and ethanol precipitation to determine starting DNA concentration and to verify the shearing size. This purified sheared DNA also served as a positive control for the qPCR step downstream. Three samples, each containing 25 µg of sheared DNA, were taken from the remaining 900 µl of sheared lysate, and they were diluted 1:10 in dilution buffer (1% Triton X-100, 2 mM EDTA, 150 mM NaCl, 20 mM Tris [pH 8], 1 mM PMSF). Two micrograms of antibody specific to the transcription factor epitope tag (Anti-Xpress™) were added to the first sample. Two micrograms of an unrelated antibody (Anti-Myc) were added to the second sample to serve as a negative control. The third sample contained no antibody and served as an additional negative control. All three samples were rotated at 4° C. overnight. The following morning, protein A/G agarose beads were added to the samples containing the transcription factor-antibody complexes. The beads were then washed in increasingly stringent conditions (by increasing and changing salts) to remove factors binding non-specifically to the beads or antibody. Protein:DNA complexes were removed from the beads by addition of 500 µl of fresh elution buffer (1% SDS, 100 mM NaHCO$_3$) and rotation at room temperature for 15 minutes. Cross-links were reversed by addition of 10 µl of 5M NaCl and incubation at 65° C. overnite. The precipitated DNA was purified by phenol:chloroform extraction and ethanol precipitation.

Enrichment of DNA sequences bound to a particular transcription factor was determined by comparing the cycle (Ct) when each qPCR reaction crosses a threshold in the middle of the exponential amplification phase of the reaction. Reactions were performed using an ABI Prism 7900HT with ABI Sybr Green PCR master mix, 150 nM of each primer, and immunoprecipitated DNA template. The log fold-change in enrichment was calculated as $\log((1+E_i)^{C_i-U_i})$, where $E_i$ is the median efficiency of the PCR primers for gene i, $C_i$ is the Ct value for the DNA enriched using correct antibody for the transcription factor regulating gene i, and $U_i$ is the Ct value for the DNA enriched using unrelated antibody for the transcription factor regulating gene i. To make the $C_i-U_i$ enrichment values comparable across each set of replicates, the values for each set of replicates were scaled by the median enrichment value of that set. Outlier enrichment values for each promoter were removed by Grubbs test. Interactions were declared significant when the log fold-change in enrichment for a given gene was significantly greater, by a t-test ($P<=0.01$) and a non-parametric rank sum test ($P<=0.01$), than a set of 66 samples taken from the promoter regions of 11 random genes not regulated or inferred to be regulated by the transcription factor being tested. The interactions for Lrp were also tested in Davis minimal media. Lrp interactions enriched in either media were declared significant.

More than 750 novel regulatory interactions were identified by the CLR algorithm at the 60% confidence level. Chromatin immunoprecipitation with quantitative PCR (ChIP-qPCR) was performed to obtain physical confirmation for many of these interactions. In particular, three transcription factors (Lrp, PdhR, and FecI) with substantial connectivity in the network mapped by CLR were studied. For each transcription factor, 26-35 operons with at least one inferred interaction were tested by ChIP-qPCR for a total of 93 tested operons (244 genes). (qPCR analysis of fecA combinatorial regulation is described below.) Many interactions with confidence levels as low as 2% were included in our ChIP-qPCR experiments to verify that the confidence estimates are reliable across their entire range and to determine if the estimates extrapolate to genes not included in RegulonDB. Presented herein are the ChIP tested operons with CLR scores above a 60% accuracy threshold (31 of 244 tested regulatory interactions).

Figures 8A, 8B:
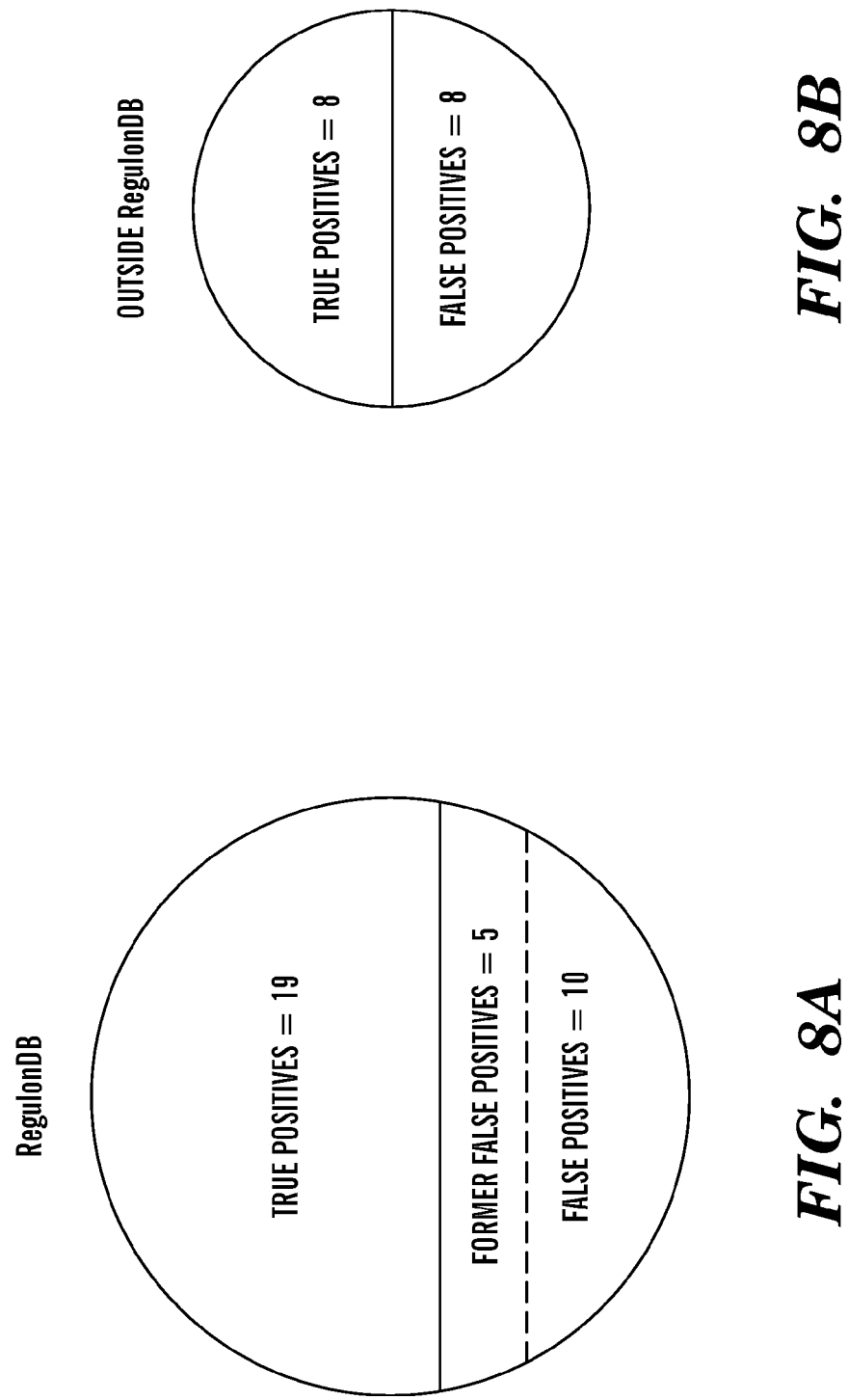
FIG. 8 shows a Venn diagram summarizing the results of the ChIP validations performed on interactions above 60% accuracy. (A) The incomplete knowledge of *E. coli* regulatory networks causes estimates of precision based on RegulonDB to be underestimates. For the interactions tested by ChIP, the RegulonDB precision estimates were underestimated by 15%. (B) 50% of the tested interactions for genes without a previously known regulator were enriched by ChIP.

The interactions among genes included in RegulonDB were first examined. For FecI, PdhR, and Lrp, it was verified that over 33% of interactions labeled false positives by our RegulonDB control data set were actually novel interactions (FIG. 8). The CLR network at a 60% accuracy threshold yielded a network with 19 interactions labeled true positives and 15 labeled false positives (56% accuracy). ChIP-qPCR showed 5 of the 15 false positives to be true positives, yielding a true accuracy of 71%. This improved accuracy reflects the extent to which the accuracy estimates in FIG. 3b are underestimated due to the incompleteness of RegulonDB. Since all of these genes already have at least one regulator, these results indicate that even the well-studied genes may have more complex combinatorial regulation than previously supposed. Also tested were interactions predicted for genes with no known regulator in RegulonDB. Half of these interactions were verified by ChIP-qPCR as physical transcription factor-promoter binding regulators (FIG. 8).

qPCR Analysis of fecA Combinatorial Regulation

Strain MG1655 cells were grown in M9 minimal media supplemented with 0.1% casamino acids. Sixteen combinations of sodium citrate (0 mM, 0.25 mM, 0.5 mM, or 0.75 mM) and sodium pyruvate (0%, 0.1%, 0.2%, 0.4%) were added, representing all possible combinations of the three concentrations tested for each chemical. Three to six replicate cultures were grown for each pyruvate/citrate combination. Cells were grown at 37° C. to a density of $10^8$ cells/ml as measured by absorbance at 600 nm. Two ml samples of each replicate culture were stabilized in 4 ml of Qiagen RNAprotect reagent. RNA was prepared using Qiagen RNeasy kits. Reverse transcription of 1.5 µg total RNA was performed with 10 units/µL Superscript III Reverse Transcriptase (Invitrogen) using 2.5 mM random hexamers in a total volume of 20 µL, according to the manufacturer's instructions.

Quantitative PCR primers for the experimental fecA transcript, positive control aceE transcript, and the normalization transcripts rrlG and rrnA were designed using Primer Express Software v2.0 (Applied Biosystems). Primer specificity was confirmed with gel electrophoresis. PCR reactions were prepared using 2 µL cDNA in a total volume of 14 containing 300 nM of each primer and 7 µL ABI Sybr Green Master Mix. Triplicate PCR reactions were performed and averaged for each of the biological replicates. Reactions were run in an ABI 7900HT.

Crossing-point threshold (Ct) and real-time fluorescence data were obtained using the ABI Prism Sequence Detection Software v2.0. Default software parameters were used except for adjustments made to the pre-exponential phase baseline used to calculate Ct for the higher abundance RNAs. Expression levels were obtained from Ct values as previously described[46].

Validation of CLR by Sequence Analysis of Regulatory Motifs

Using the set of gene targets predicted for each transcription factor, sequence analysis algorithms were applied to infer the sequence motif bound by each regulator. Not all transcription factors have enough targets to allow reliable motif detection, but for those that do, the motif provides a specific location for the regulatory interaction. A significant sequence motif for a group of genes predicted to have the same regulator also provides an additional level of validation, as it is unlikely that a group of genes not regulated by the same transcription factor would have a common motif. To detect sequence motifs, all transcription factors (64 total) predicted to regulate five or more operons with greater than 60% confidence were selected. For each group of operons regulated by the same transcription factor, approximately 150 bp upstream of the transcription start site were analyzed with the MEME multiple alignment system[67]. Overall, a significant (one-tailed p-value <0.05) binding motif was detected for 31 out of the 64 transcription factors (Table 2).

Figure 10A:
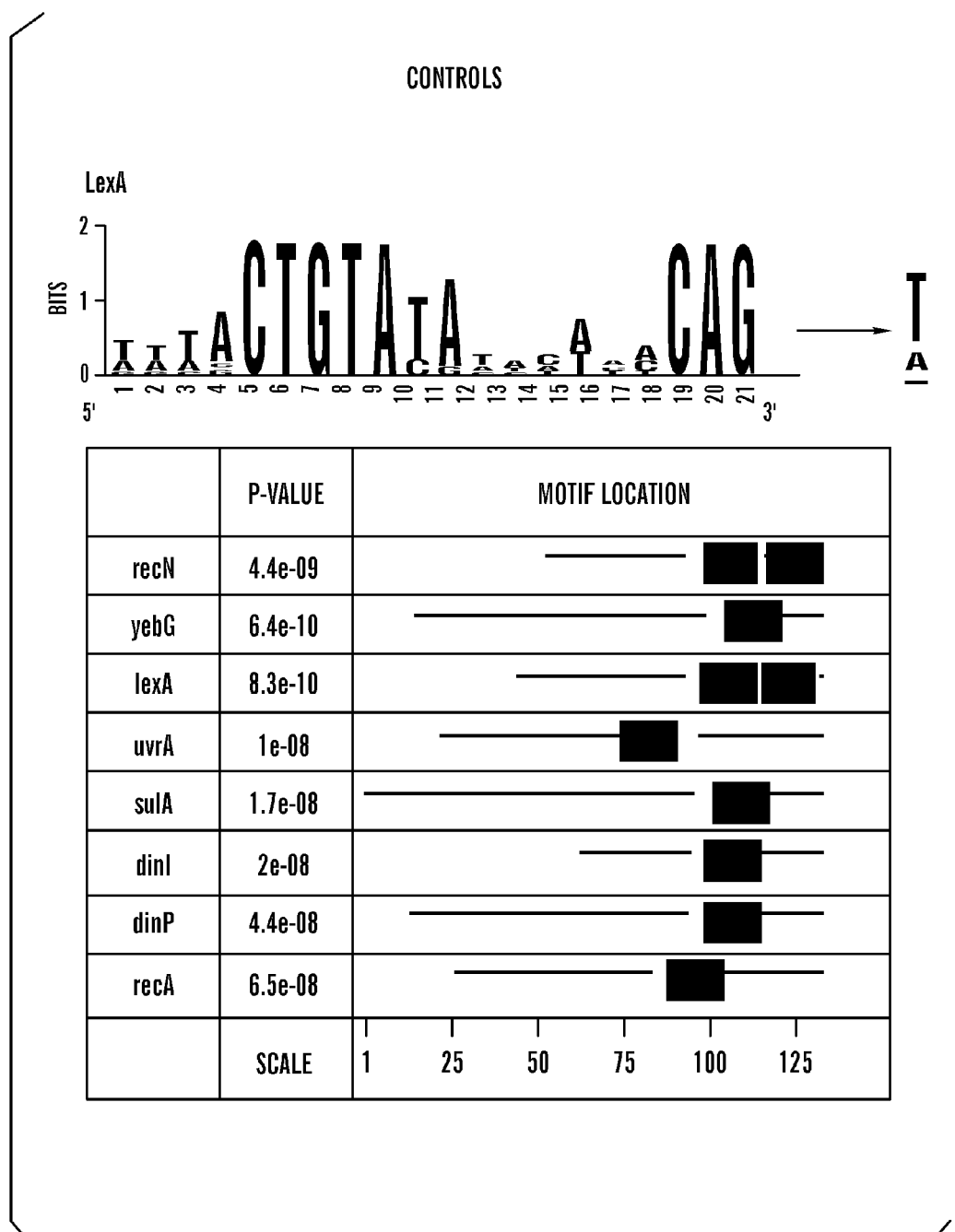
FIG. 10 shows that motifs were detected for many of the transcription factors with five or more target operons. (A) The canonical LexA regulatory motif (SEQ ID NO:1) was detected in the promoters of 8 out of the 13 genes inferred to be LexA targets. The LexA consensus sequence in FIG. 10A is shown as SEQ ID NO: 8. (B) The canonical Lrp regulatory motif (SEQ ID NO:2) was also detected with high significance. The Lrp consensus sequence in FIG. 10B is shown as SEQ ID NO: 9. (C) A novel motif (SEQ ID NO:3) was found for YnaE, a transcription factor that may play a role in the regulation of a prophage or DNA repair. The YnaE consensus sequence in FIG. 10C is shown as SEQ ID NO: 10. (D) YmfN, another prophage-related transcription factor with no known regulatory targets, had a strong motif conserved in all of its predicted targets.

LexA, a major regulator of DNA repair, is one of the best-perturbed regulators in the microarray compendium due to the compendium's emphasis on DNA-damaging conditions. Consequently, the LexA protein has a large set of correctly predicted targets and exhibits a highly significant motif almost identical to the known canonical LexA motif (FIG. 10a). Five out of eight promoters containing the LexA motif in FIG. 10a are known LexA targets according to RegulonDB. The other three promoters for dinI, dinP and yebG are confirmed LexA targets[68] but are not catalogued in RegulonDB.

Figure 10B:
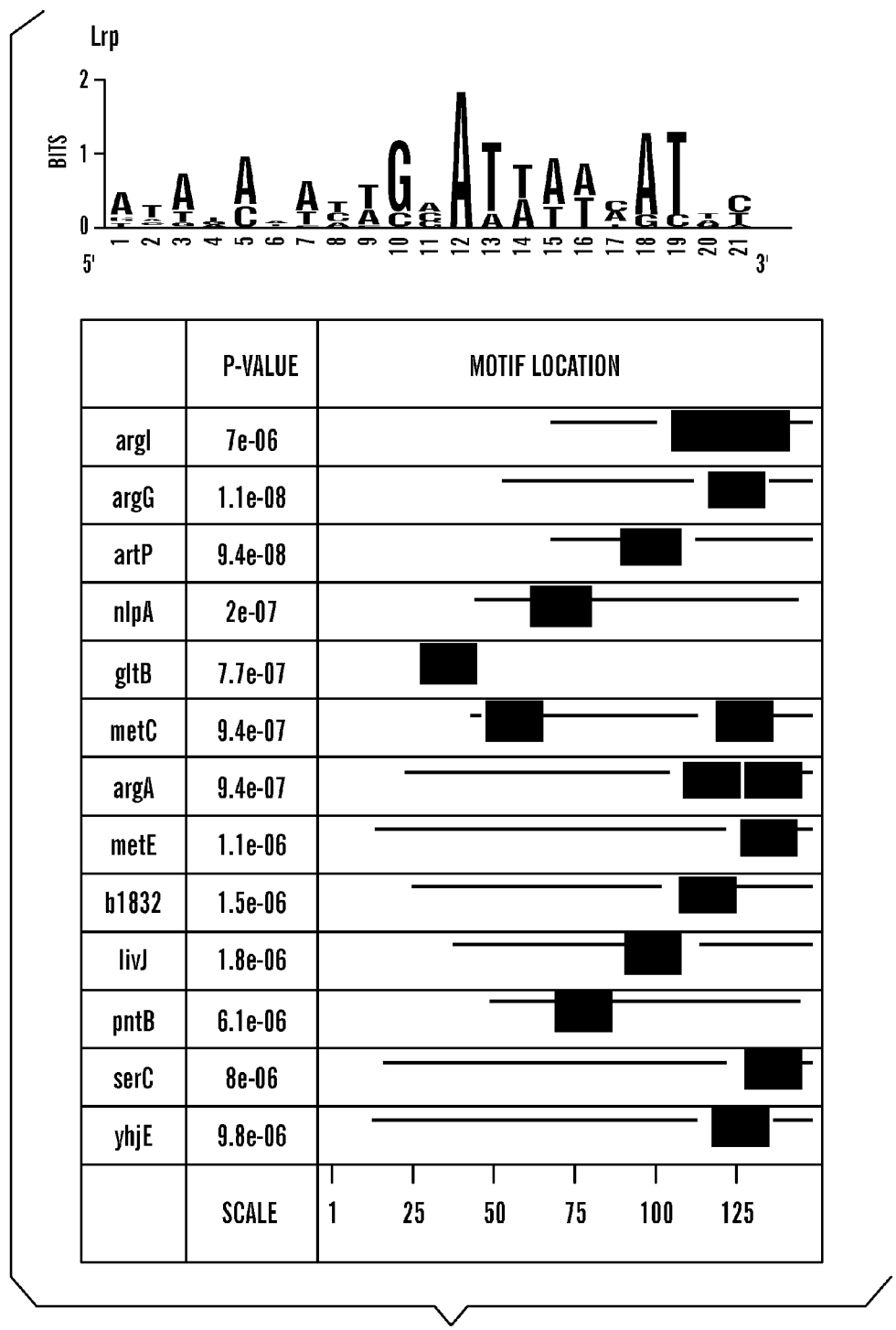

Motif analysis also works well for other perturbed hubs. For example, the majority of the operons predicted to be in the Lrp regulon carry the Lrp motif (FIG. 10b). It is possible that some of the other promoters also carry a secondary Lrp motif, since Lrp changes its binding site affinity when bound to leucine.

Figure 10C:
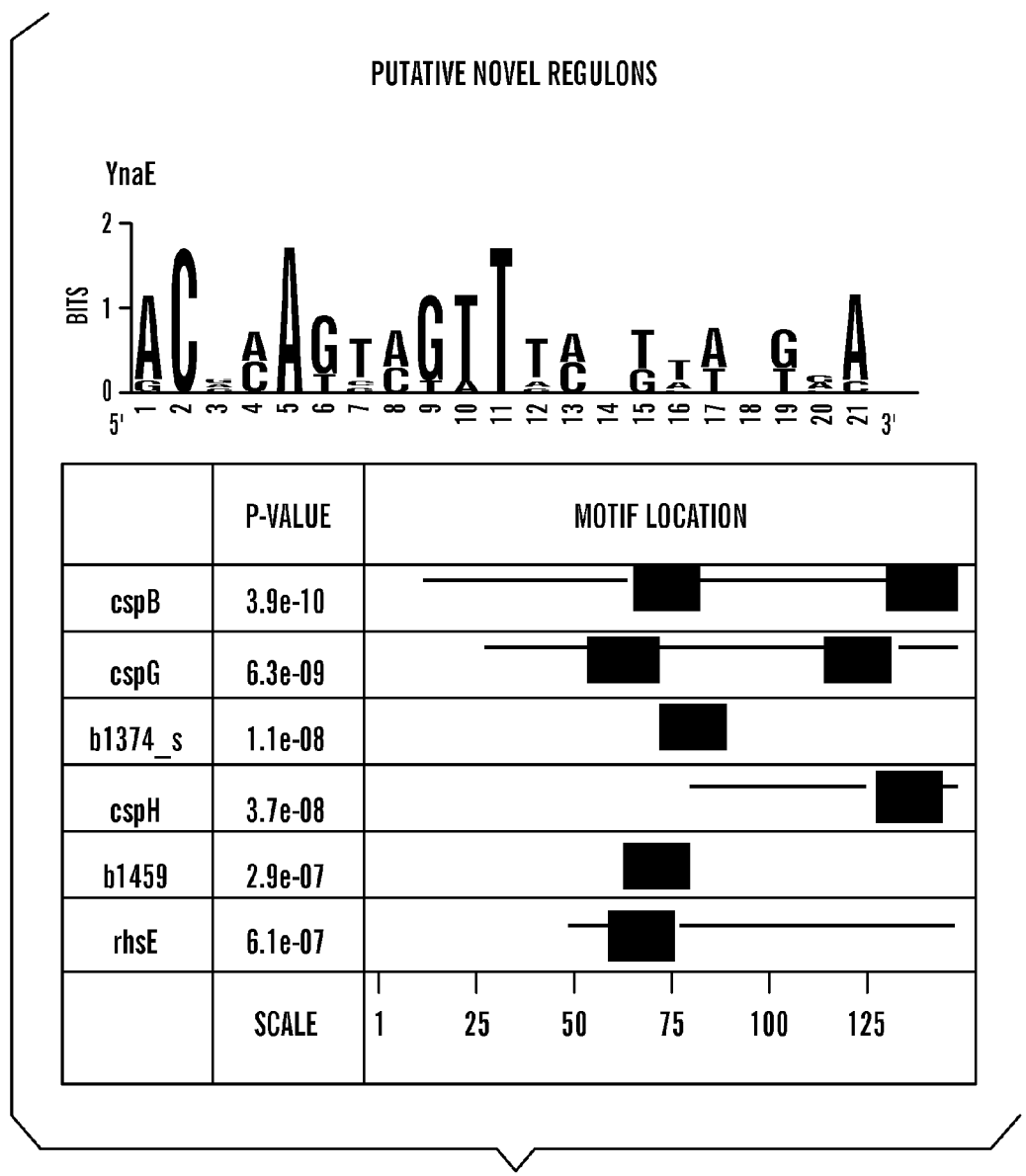
Figure 10D:
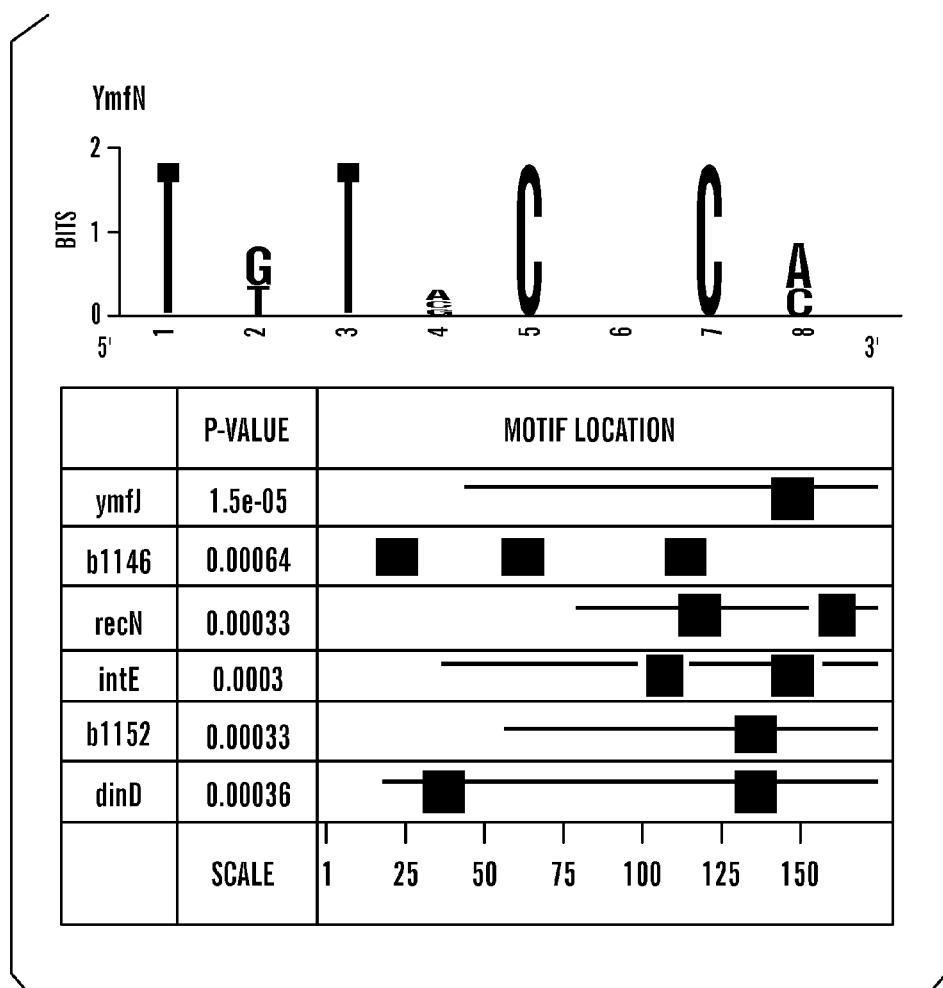

FIGS. 10c and 10d illustrate this approach applied to two putative regulators, YmfN and YnaE. YmfN is a putative DNA-binding protein homologous to a phage terminase. A strong motif (p-value≈0.0061) was found in all six of the operons inferred for this transcription factor by CLR (FIG. 10d). ymfN attains its highest levels of expression in the compendium upon exposure to norfloxacin, a DNA-damaging bactericidal agent, and its inferred targets show enrichment in prophage and DNA repair categories (Table 3).

YnaE (Rac prophage) is another putative DNA-binding protein. The latest computational annotation for YnaE available in Ecocyc suggests its function is also phage-related[69]. There is enrichment for cold-shock response proteins in the predicted YnaE regulon (Table 4). Also present are rhsE, a stationary phase survival-related protein, and b1374, a putative transposon resolvase. In the compendium, ynaE was highly expressed when Lon protease or YoeB toxin was genetically upregulated and when either norfloxacin antibiotic or mussel defensin protein was present. Based on the present analysis, YnaE may control a small, specialized stress response network in E. coli.

Example 4

Comparison of Network Inference Algorithms

Given the number of algorithms in the expanding field of network inference[62], the inventors have compared the performance of three algorithms in addition to CLR—Relevance Networks[63], ARACNe[64] and a variant of Bayes Nets[65]. All four algorithms were tested with each of four microarray normalization procedures (MAS5, RMA, GCRMA, DChip PM). For each algorithm, microarray data processed by the normalization procedure that produced optimal results based on the RegulonDB control set was used; for CLR and Relevance Networks the optimal procedure was RMA, and for ARACNe and Bayes it was a "consensus" network obtained by applying the algorithm four times, each time using data normalized with a different one of the four methods, and then averaging the resulting networks. The output of each algorithm consists of a set of regulators and the inferred gene targets of those regulators.

Figure 9:
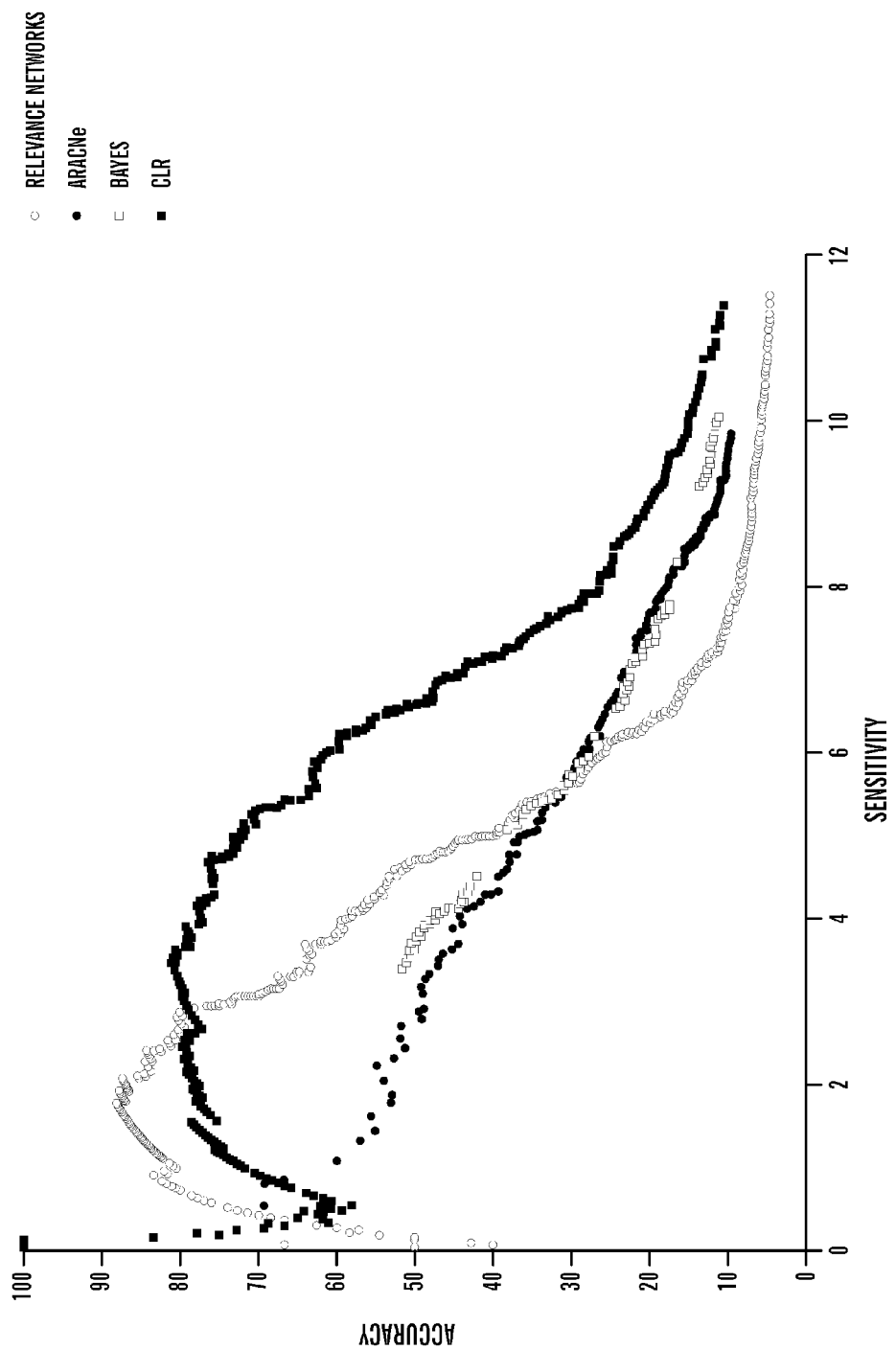
FIG. 9 shows accuracy and sensitivity of four different network inference algorithms applied to all 4345 genes in the *E. coli* microarray compendium of 445 microarrays as calculated using RegulonDB.

The Relevance Networks algorithm achieves accuracy levels near 90%, but with roughly half the sensitivity that CLR reaches at similar accuracy levels (FIG. 9). Bayesian networks and ARACNe are two other algorithms frequently referenced in the recent network inference literature that have been successfully applied to yeast and human B cells respectively[64,66]. Variants of these algorithms were developed to enhance their performance with microbial microarray data (based on the RegulonDB scoring scheme). Both algorithms achieved similar, biologically useful levels of performance, but neither performed as well as CLR (FIG. 9). The purpose of the algorithm comparison was not an exhaustive survey of algorithm performance. Rather, it was aimed to determine which algorithm's results to use for subsequent analysis and experimental validation of E. coli regulatory pathways.

Example 5

Experimental Design for Network Inference

The compendium used in the Examples described herein was not purpose-built for network inference. It contains conditions reflective of the interests of the contributing laboratories. However, by determining the conditions and factors that are most informative to network inference, one can gain insight into the design of future microarray compendiums constructed with the intent of inferring the largest accurate regulatory network with the fewest microarrays.

Diversity of the Compendium Influences Network Inference Sensitivity

The number and phenotypic diversity of expression profiles in the compendium was expected to significantly impact the sensitivity of the CLR algorithm. To test the influence of these factors on the inferred network, the smallest set of microarrays sufficient to reconstruct a network equal in sensitivity and accuracy to a network constructed with all 445 arrays was identified. Clustering was used to select the most dissimilar subset of expression profiles from the compendium. Performance of the CLR algorithm was measured on this subset. Subsets of randomly chosen expression profiles and sets of the most similar profiles were also analyzed.

As expected, the most dissimilar set provided the best performance using the fewest profiles. Using this set, only 60 profiles were required to infer the network with performance equal to that obtained with the entire 445 profiles in the data set (FIG. 3c). Thus, the 60 most diverse conditions are a sufficient representation of the entire dataset, while the remaining arrays provide mostly redundant information. Each of the 60 conditions is selected from a different cluster where each cluster represents groups of experiments from related environmental conditions (Table 5). These results suggest that in-depth sampling of related conditions or perturbations is not necessary to infer an accurate map of the transcriptional regulation network; rather, it is more important to select conditions to maximize physiological diversity.

Shotgun Mapping of Transcriptional Regulation in Microbes

The CLR algorithm identifies approximately 8% of the known *E. coli* transcriptional regulatory map from only 60 microarrays. By extrapolation, this result suggests that the identification of a complete transcriptional regulatory map of a prokaryote can be assembled with only 700-1000 phenotypically diverse expression profiles. Of course, this number must be regarded with caution as it is obtained by extrapolation from the existing data. It also assumes that the algorithm performs with equal sensitivity and accuracy in unmapped portions of the network—a reasonable assumption. Some interactions may remain undetected in any experiments however, due to current limitations of microarray profiling technology[70]. A similar extrapolation given the number of interactions and sensitivity of the 60% accuracy network, suggests *E. coli* has 6000-10,000 transcriptional regulatory interactions.

In practice, this estimate of 700-1000 profiles likely represents a lower bound on the number of expression profiles needed to infer a complete transcriptional regulatory network because it presumes that experiments are selected optimally for maximum phenotypic diversity. Such an optimal selection is not necessarily possible in a prospectively designed set of experiments. However, analysis of the existing data set suggests a strategy for experimental design that may help approach this optimal number. For example, examination of the minimal subset of 60 microarrays suggests that large perturbations, like media changes and addition of drugs, are far more informative to the regulatory pathway inference algorithm than genetic perturbations, such as gene overexpressions and knockouts. It is thought that this is the case because environmental variation will, in most instances, cause multiple regulatory changes, while genetic perturbations may cause few or none.

Additional insight into experimental design is provided by the examples in FIGS. 2a and 2b, which show that regulatory relationships become detectable as soon as samples of the relevant condition are added to the compendium. The figures show that LexA targets are only detectable when SOS response conditions are sampled and AraC targets are detectable only when arabinose metabolizing conditions are sampled. This characteristic suggests that much of the transcriptional regulatory network may be incrementally constructed by profiling the expression of an organism in as yet unsampled physiological states.

The Lrp regulon (FIG. 2d) provides an additional example. When using only those profiles sampled from cells grown in rich (LB) media, Lrp (a transcription factor that is highly expressed in minimal media) had no inferred targets. Most of the known Lrp targets had a weak, incorrect correlation to LexA (FIG. 2c inset), but these correlations were correctly eliminated by CLR. Only when the arrays from minimal media were combined into the same dataset did the CLR algorithm successfully identify the targets of Lrp (FIGS. 2c, 2d, 4, and 5b).

Taken together, these results indicate that an informed "shotgun" approach can be applied to systematically map transcriptional regulatory networks in microbes. A compendium of expression profiles can be constructed by sampling a broad set of environmental conditions relevant to the life cycle of a particular microbe. An algorithm such as CLR can then be applied to map the transcriptional networks underlying the organism's responses to these conditions. For example, the natural environment of *E. coli*, the gut, provides a vast set of potential perturbations in the form of food sources, bile, immune factors, antimicrobial peptides, and secreted factors from other microbes that have only recently begun to be studied in the literature[71-74]. Another source of potential perturbations to expand the *E. coli* compendium is the list of GO function categories with the greatest number of unperturbed transcription factors (Table 6) or genes (Table 7) in the current compendium.

Such a shotgun approach to sampling the physiology of a microbe presents an experimental challenge because an unmanageable number of conditions are conceivable. Which ones should be sampled, and in which combinations, to obtain the most informative data set? A practical solution to this problem can be found in the statistical design of experiments pioneered 60 years ago by Ronald Fisher. Fisher's approach addressed the question of how to obtain reliably the most information with the fewest experiments[75,76]. Studies employing factorial designs, fractional factorial designs, or more recent Bayesian designs, are already commonplace in industrial research and optimization. These or similar methods have had proponents in the field of microarrays[77,78], but have received little attention in larger microarrays studies. These designs should make the generation of a compendium covering the phenotypic space of an organism a more manageable task.

Example 6

Combinatorial Regulation in the CLR Regulatory Map

As compendiums grow with the reduced cost of microarrays, network inference algorithms will uncover more of the intricate combinatorial regulatory schemes of cells. Currently, there are 824 cases, among the known *E. coli* regulatory network, where a gene is regulated by 2-10 transcription factors[79,80]. By adding new interactions whose accuracy is 80% or greater, the data described herein increases the number of combinatorially regulated genes increases by approximately 50.

Figures 11A, 11B:
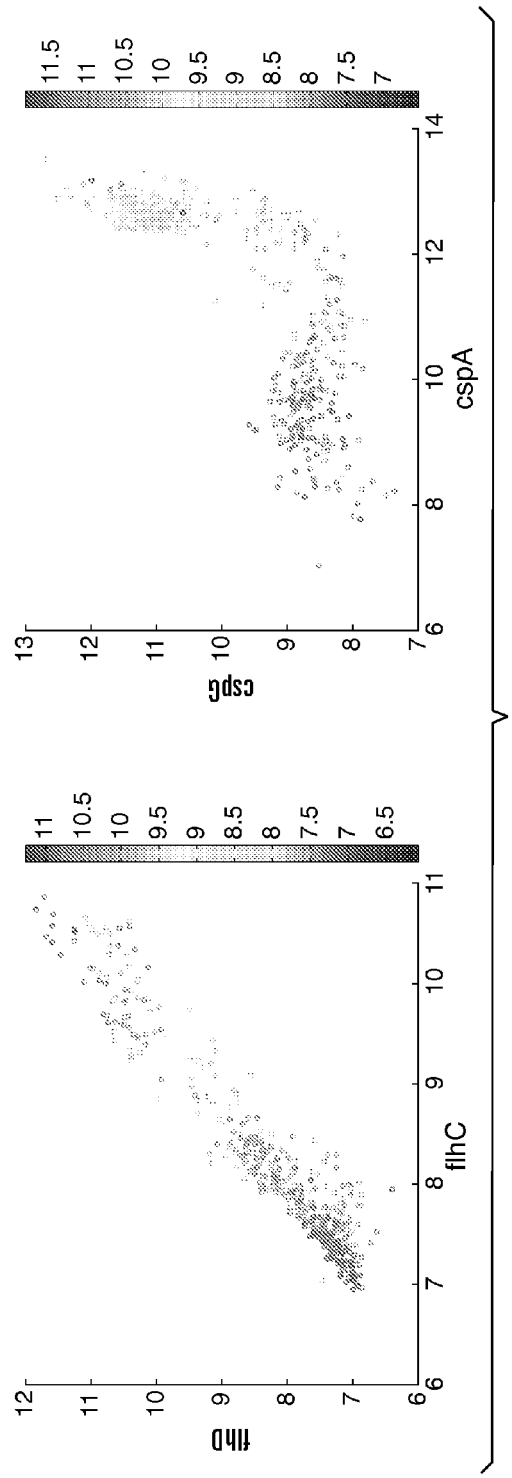
FIG. 11 shows combinatorial regulation observed in the *E. coli* compendium. (A) Combinatorial regulations can be classified by discretizing the expression levels of the relevant transcription factors and genes into on (T) and off (F) states. In this example, two transcription factors, (TF1) and (TF2), regulate their target gene with AND-like logic. (B) Many of the cases where one gene is regulated by multiple transcription factors involve two transcription factors in the same operon, which eliminates the ability to see either transcription factor expressed independently of the other. This case is difficult to classify as combinatorial regulation. (C) Novel interactions were predicted between CspA and CspG, two transcription factors involved in cold shock, and the target gene ddg, whose expression values are represented as grayscale color changes. (D) The expression profiles for the three cold shock genes strongly suggest an AND-like regulation, but there are no data for the case of high cspG expression with low cspA expression, thus preventing the conclusive determination of this promoter's combinatorial logic program.

A simple way to classify combinatorial interactions is to discretize the expression values of each gene and transcription factor into two states (FIG. 11a). The set of all states (the "combinatorial state space") of the transcription factors and their target under study form a truth table that determines the combinatorial logic function of the transcription factors. For example, in the case of two transcription factors targeting one gene, if the target gene is highly expressed only when both transcription factors are highly expressed, the regulation would be classified as AND-like; whereas if the target gene is highly expressed when either or both of the regulators are highly expressed, the regulation would be classified as OR-like.

Most of the 67 cases of combinatorial regulation, involving 2-3 transcription factors in which at least one of the regulatory interactions was also predicted by the CLR algorithm (the remaining edges were known edges in RegulonDB), have insufficient data points in the compendium to allow the determination of the logic gate. The combinatorial regulators perturbed in the compendium are usually expressed in the same operon, and thus show high expression covariance leading to undersampling of the combinatorial state space (FIG. 11b). Complex combinatorial regulation at such promoters may not occur under normal physiological conditions.

Figure 11C:
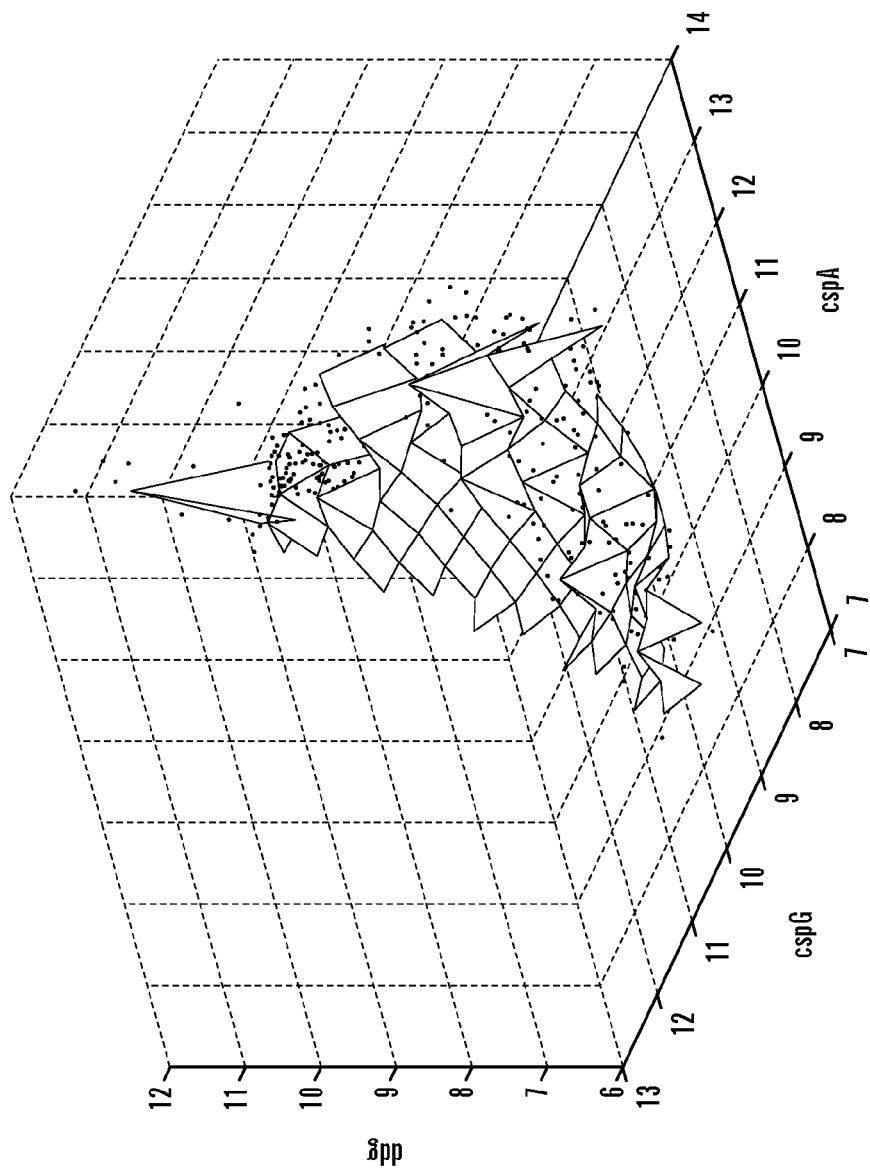

There are, nevertheless, some cases where evidence of combinatorial logic can be observed in the expression data. Two cold-shock proteins, CspA and CspG, are identified by CLR to regulate ddg, a gene which encodes an enzyme that incorporates palmitoleate instead of laurate into lipid A when E. coli undergo cold-shock or growth at below 12° C.[81]. The compendium data indicates that the two regulators operate by AND-like logic (FIGS. 11c and 11d). CspA and CspG are two of the four cold-shock proteins in a quadruple deletion that results in a cold-temperature dependent growth defect[82]. These results are in concordance with the current working hypothesis that the cold-shock genes evolved by duplication of the cspA family genes whereupon the duplicated genes each acquired a more specific role[82]. These results indicate that CspA is expressed under a large range of temperature conditions, and its presence is required in addition to the more specifically expressed CspG protein to induce the expression of ddg, which can then incorporate palmitoleate into lipid A in place of laurate.

Example 7

Determination of Novel Connectivity in the LRP Regulon

Figure 4A:
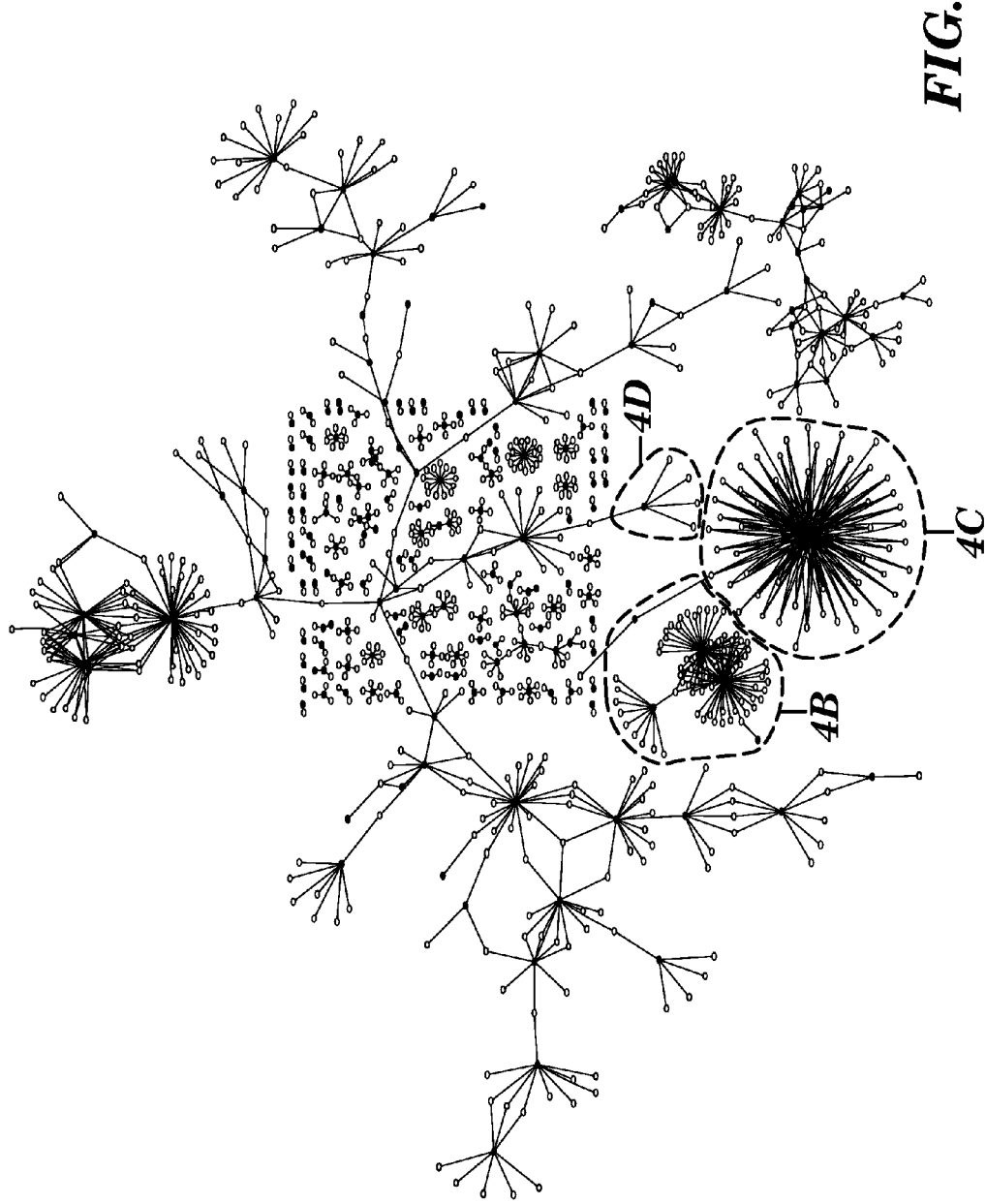
FIG. 4 shows the transcriptional regulatory map inferred by CLR with an estimated 60% accuracy. The accuracy of the network is obtained by measuring the percentage of correctly inferred edges (thin solid lines) out of all the predicted edges for genes with known connectivity (thin solid lines and bold solid lines). The bold solid line edges represent a mixture of false and novel predictions, making 60% an underestimate. The intermediate solid line edges connect genes/regulators with no previously identified interactions (i.e., genes not in RegulonDB). A portion of the regulatory map containing many of the Lrp interactions is shown in the expanded box. Uniformly dotted lines were tested by ChIP. Thin dashed lines comprised of short dashes and thin dashed lines comprised of long dashes are previously unknown targets of Lrp, experimentally verified by ChIP. Genes attached to thin, short-dashed lines previously had no known regulator.
Figure 4C:
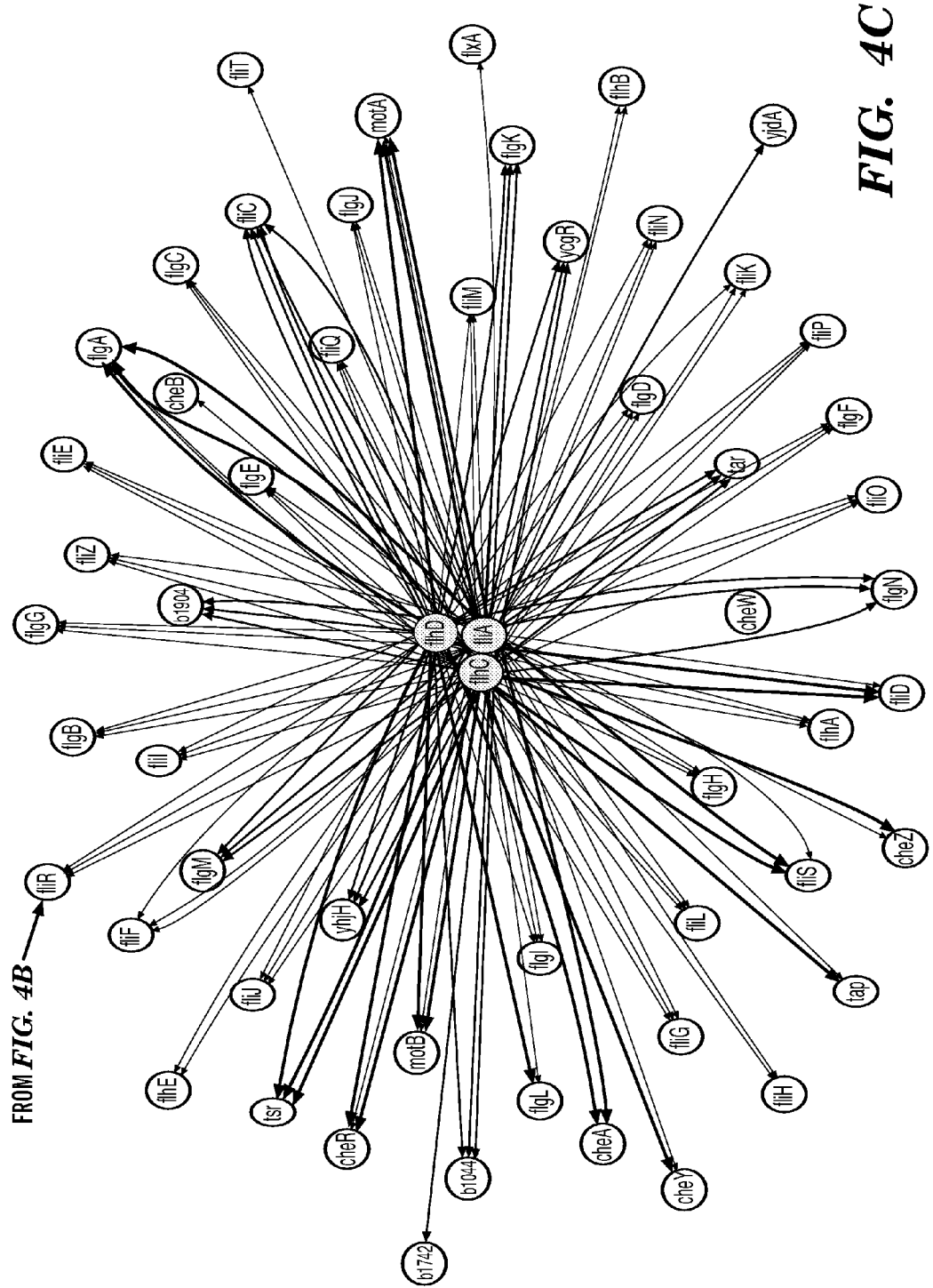
Figure 4D:
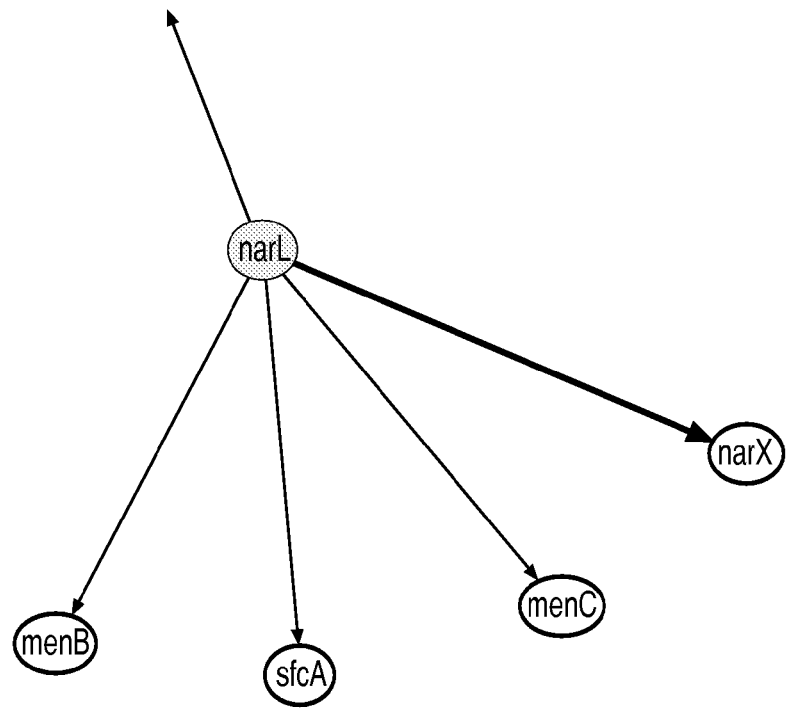
Figure 5A:
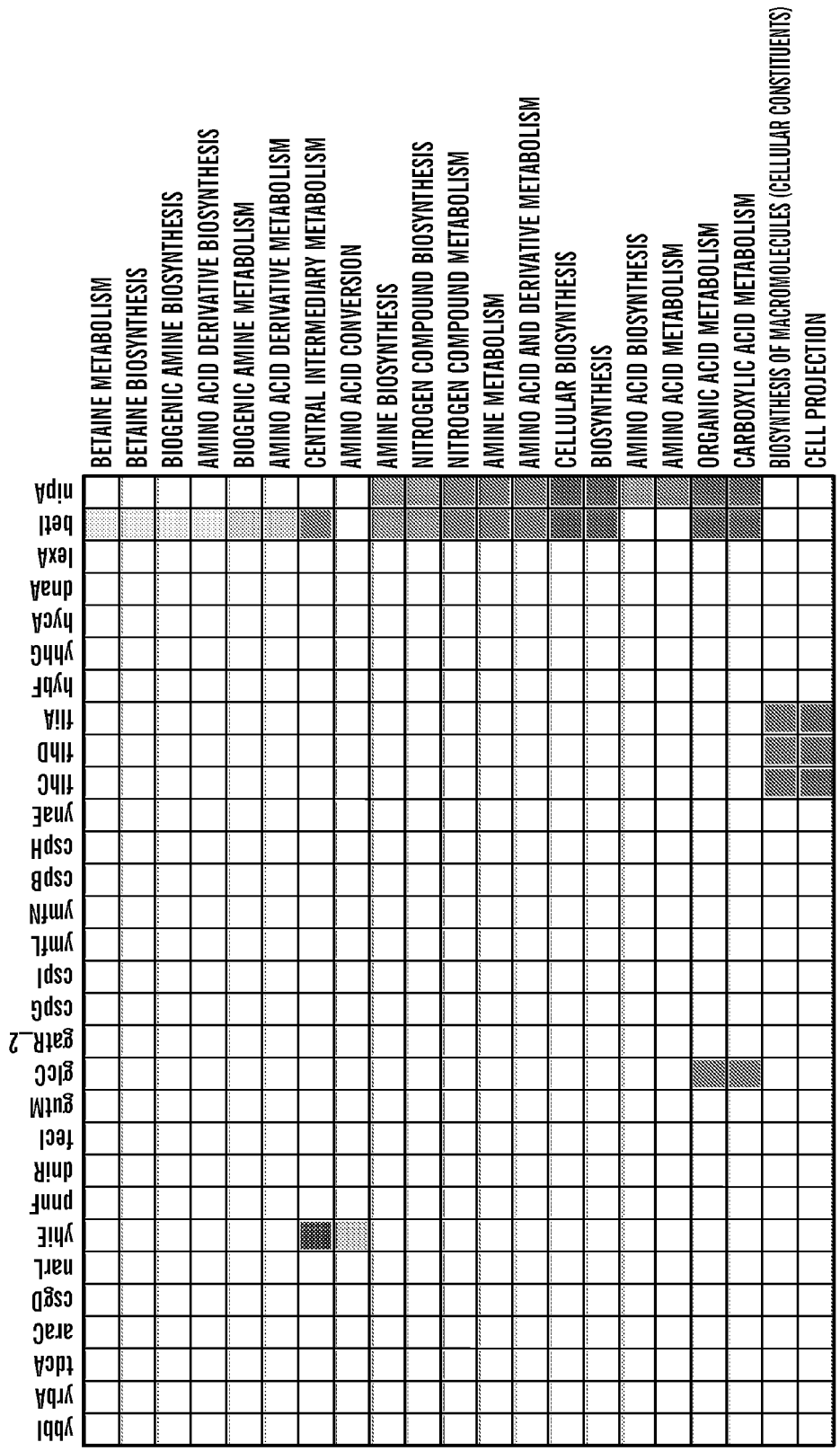
FIG. 5 shows annotation of transcription factor function by functional enrichment using predicted targets from the 80% accurate network.
Figure 5B:
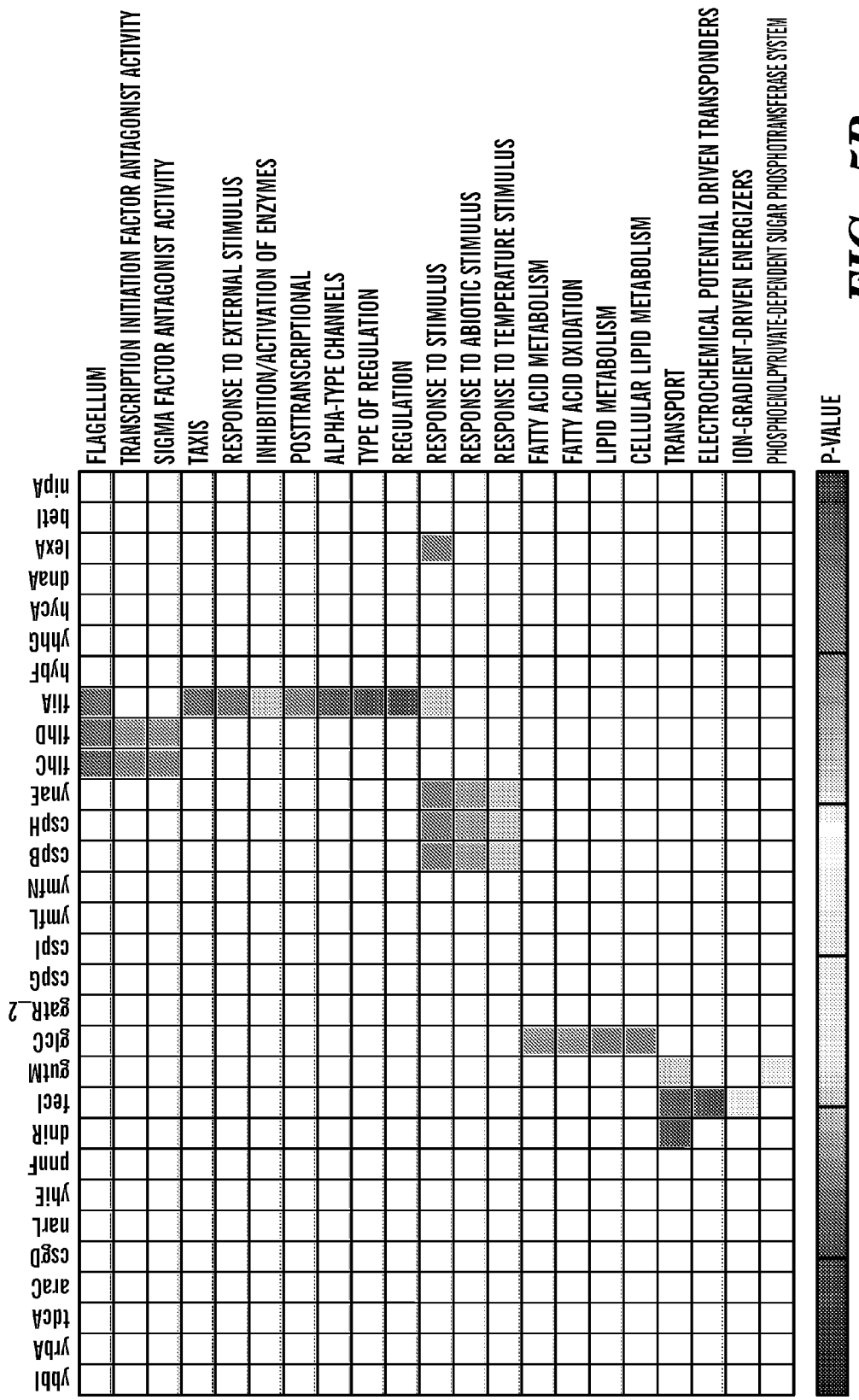
Figure 5C:
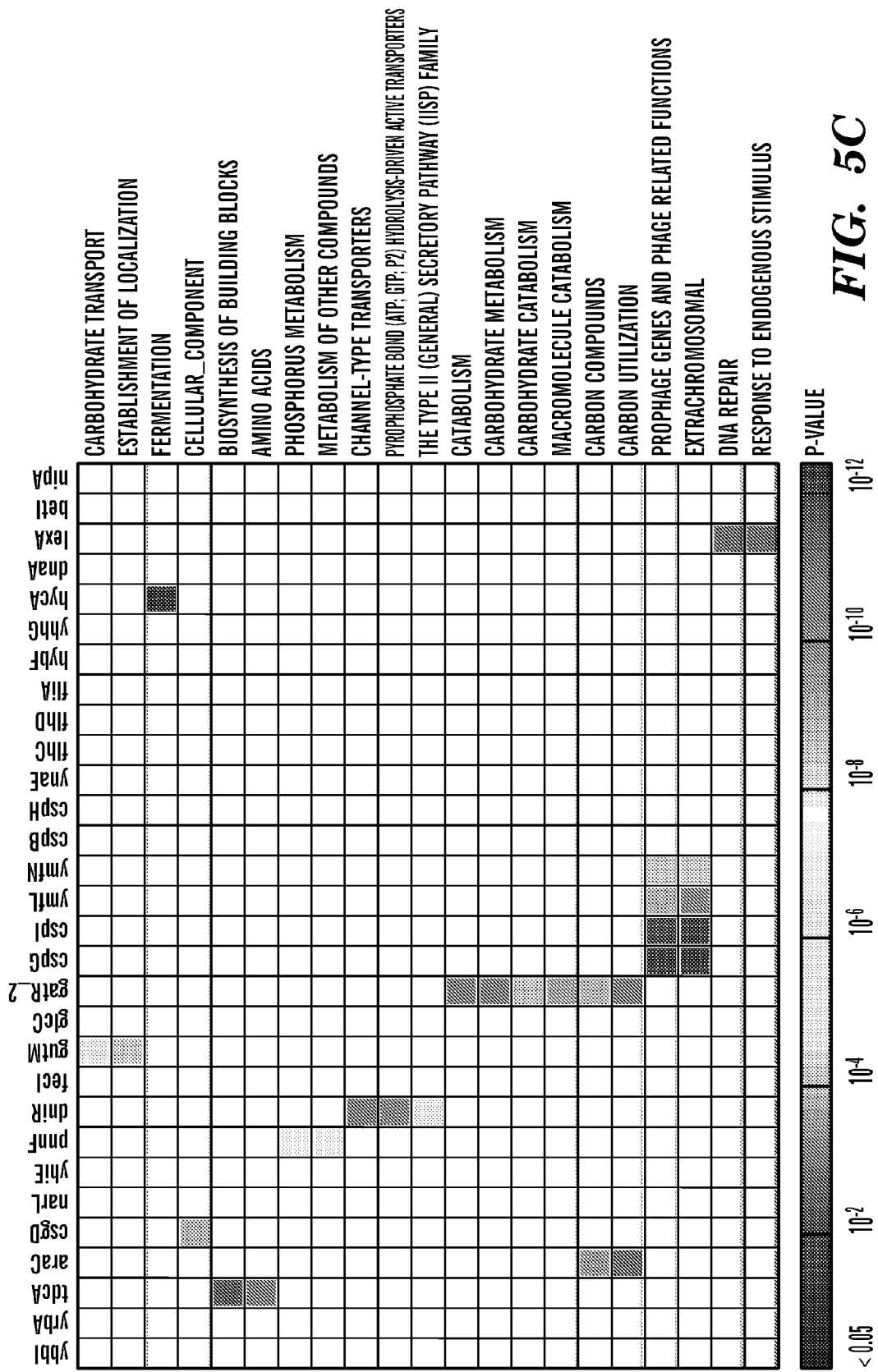
Figure 5D:
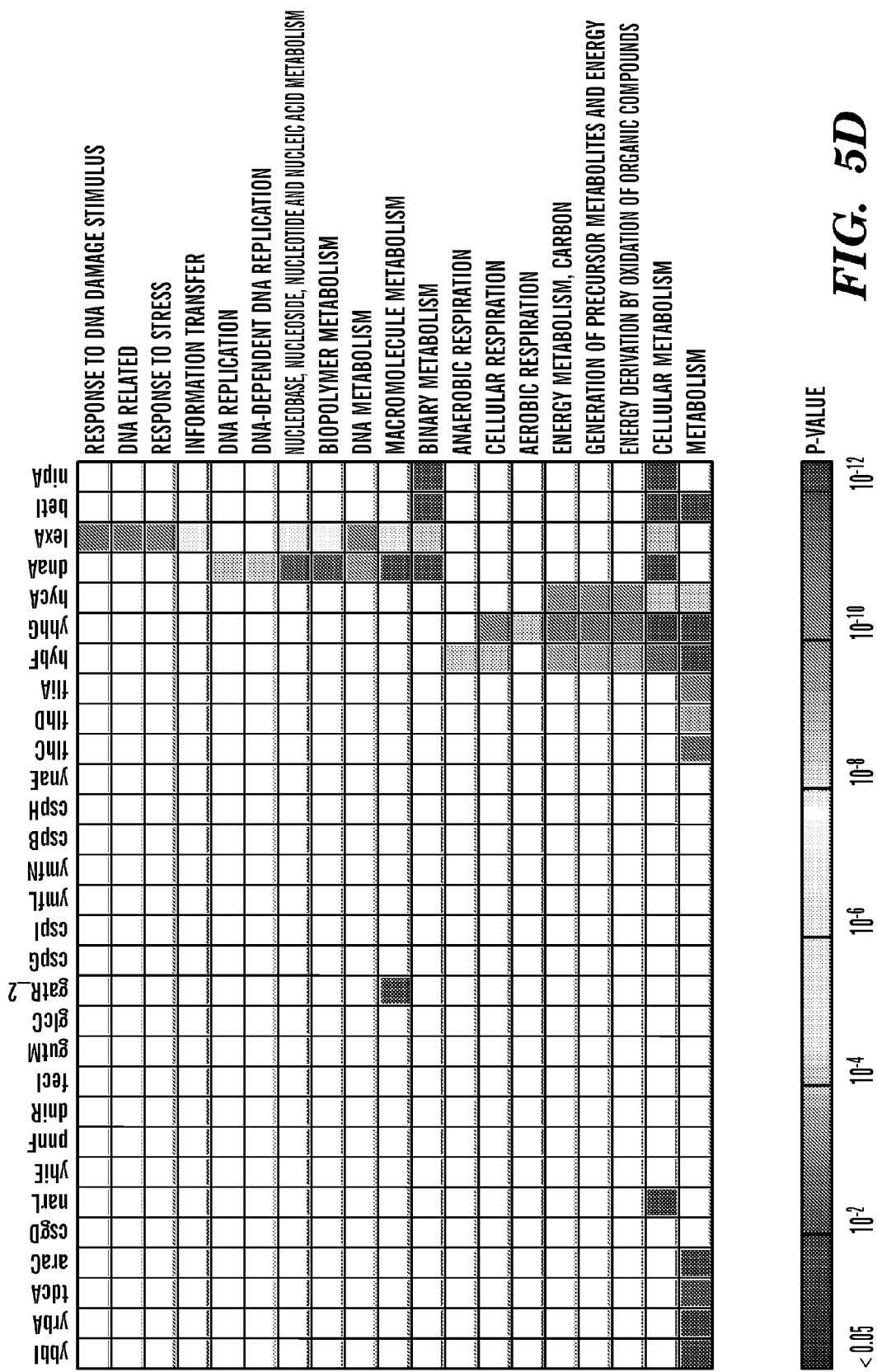

Many of our confirmed novel interactions are for the transcription factor Lrp (Leucine Response Protein; FIG. 4 edges shown by thin dashed lines comprised of short dashes and thin dashed lines comprised of longer dashes), a global regulator found in numerous prokaryotes[32,33]. Lrp has been shown to be predominately a regulator of the biosynthesis and transport of metabolites. It is highly activated in minimal media when the cell must coordinate the synthesis of its own nutrients rather than rely on using those from the environment (FIG. 2d). CLR infers 37% of the known and newly verified Lrp targets, nearly four times the sensitivity measured for the full regulatory network. This high sensitivity is likely due to the extensive sampling of minimal and rich media conditions relevant to Lrp activation. All of the confirmed novel interactions inferred by the CLR algorithm target genes relate to biosynthesis and transport (FIG. 4), consistent with the known regulatory function of Lrp. Most of the novel Lrp targets are membrane-bound and transporter proteins, giving Lrp an increasingly prominent role in the regulation of E. coli's metabolism. One interesting case is the prediction of Lrp as a regulator of two genes, pntA and pntB. These interactions were not reported in RegulonDB. These interactions were verified with ChIP, and in a subsequent literature search it was found they were originally discovered 28 years ago[34].

Example 8

Identification of a Combinatorial Link Between Central Metabolism and Iron Transport The inferred regulatory network revealed new combinatorial regulation at many promoters. These combinatorial regulation schemes were explored, first across the entire network, and second by detailed quantitative RT-PCR analysis of the novel pdhR-fecA interaction, an interaction that links central metabolism to the control of iron import—a link of potential significance in bacterial virulence and stress protection.

The presence of iron is essential for the survival of most organisms as it plays a critical role in the TCA cycle, electron transport, reducing oxygen radicals, DNA synthesis, and amino acid synthesis[35]. Iron, however, is scarce in many environments owing to the low solubility of its ferric form. Consequently, many organisms have developed elaborate mechanisms for scavenging soluble forms of the element. In E. coli K12, there are six different siderophore receptors, each representing a different chelator capable of capturing extracellular iron and converting it to a soluble form that may be transported into the cell[36]. Excess iron can be toxic to cells; iron uptake must therefore be carefully dictated by the need for cellular iron.

Figure 6D:
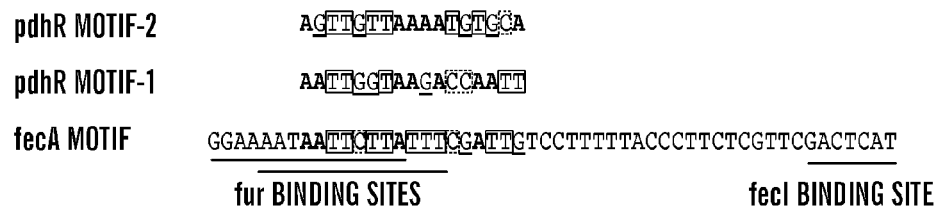
FIG. 6 shows an analysis of the regulation of the fecAB-CDE iron transport operon. (A) Fur shows no correlation to the fecA operon, one of its known target operons. (B) FecI shows correlation to its known operon target fecA with a bifurcation that suggests combinatorial regulation by another transcription factor. (C) PdhR, a regulator of pyruvate metabolism, is not known to regulate the fecA operon. However, their expression values are correlated in the compendium. (D) The proposed binding site of PdhR overlaps with the known Fur binding site. The known FecI binding motif is further downstream. The nucleotide sequences of a pdhR motif-2, a pdhR motif-1, and a fecA motif are shown in SEQ ID NOs. 5-7, respectively. (E) A schema of the new proposed regulatory structure of the fecABCDE operon. (F) Viewing the expression of fecA (the z-axis is represented as color changes corresponding to the values on the grayscale bar on the right) as a function of both transcription factors suggests its regulation by FecI and PdhR might be AND-like. (G) pdhR expression is highly dependent on the concentration of pyruvate in the media. Expression values exhibit high uncertainty at the threshold pyruvate concentration of 0.2% (represented by vertical error bars) suggesting a bifurcation of cells into high and low expression states. (H) fecA expression was measured at 16 concentrations of two chemicals, citrate and pyruvate, known to alter the expression of fecI and pdhR, respectively. The results further support the hypothesis that fecA expression is controlled with AND-like behavior by FecI and PdhR. fecA expression exhibits high uncertainty at 0.25 mM citrate and 0.2% pyruvate. As with pdhR expression in panel (G), this high uncertainty may reflect the probabilistic nature of induction near the switching threshold.
Figure 6E:
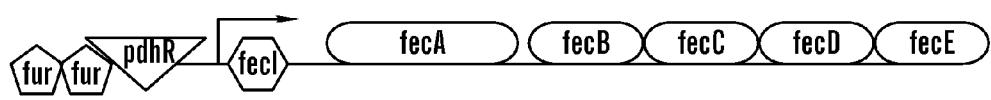

A bacterium's ability to assimilate iron can also affect its pathogenic potential, or virulence. One of the human body's natural responses to infection is hypoferraemia, or low blood iron[37]. A host's normal ability to contain and eliminate an infectious agent is severely limited when iron is administered along with the infecting microorganism[38]. This effect has been described in at least 18 bacterial species, including such important human pathogens as E. coli O111[39] and Pseudomonas aeruginosa[40]. In addition, iron can affect the bacterial state—motile or sessile—which in turn impacts the ability of microorganisms to attack organs and cause disease. Pseudomonas aeruginosa and Burkholderia cenopacia, two respiratory pathogens common in cystic fibrosis patients, have been shown to aggregate and form biofilms in response to increased iron[41,42]. Similar findings have been reported for Staphylococcus aureus[41], Staphylococcus epidermidis[43], and Vibrio cholerae[44]. The elucidation of iron signaling pathways may provide key insights into the genesis of biofilms and the mechanisms by which pathogens aggregate, adhere to, and invade host tissue.

fecABCDE is an operon that encodes a ferric citrate transporter and plays a central role in the import of cellular iron. Existing literature described only two regulators of fecAB-CDE—FecI and Fur. The Fur regulation is not apparent in the compendium (FIG. 6a), while the FecI regulation is clear (FIG. 6b). However, the bifurcation of the plot suggests a more complex combinatorial regulation for fecABCDE. The CLR algorithm identified PdhR, a pyruvate-sensing repressor and necessary component of the energy transduction cascade, as a possible additional regulator of the fecA operon (FIG. 6c). Follow-up motif detection analysis identified a potential PdhR binding motif in the promoter region of the operon (FIGS. 6d and 6e). Moreover, in undefined, rich media (LB with 0.2% glucose), the ChIP results showed a significant enrichment for PdhR-fecA binding when judged by a t-test (p-val 0.004) and a modest enrichment using a non-parametric rank-sum test (p-val 0.1). Of the six ChIP replicates, two were extremely enriched while the others are not, suggesting that the transcription factor binding may be condition-specific.

Figure 6F:
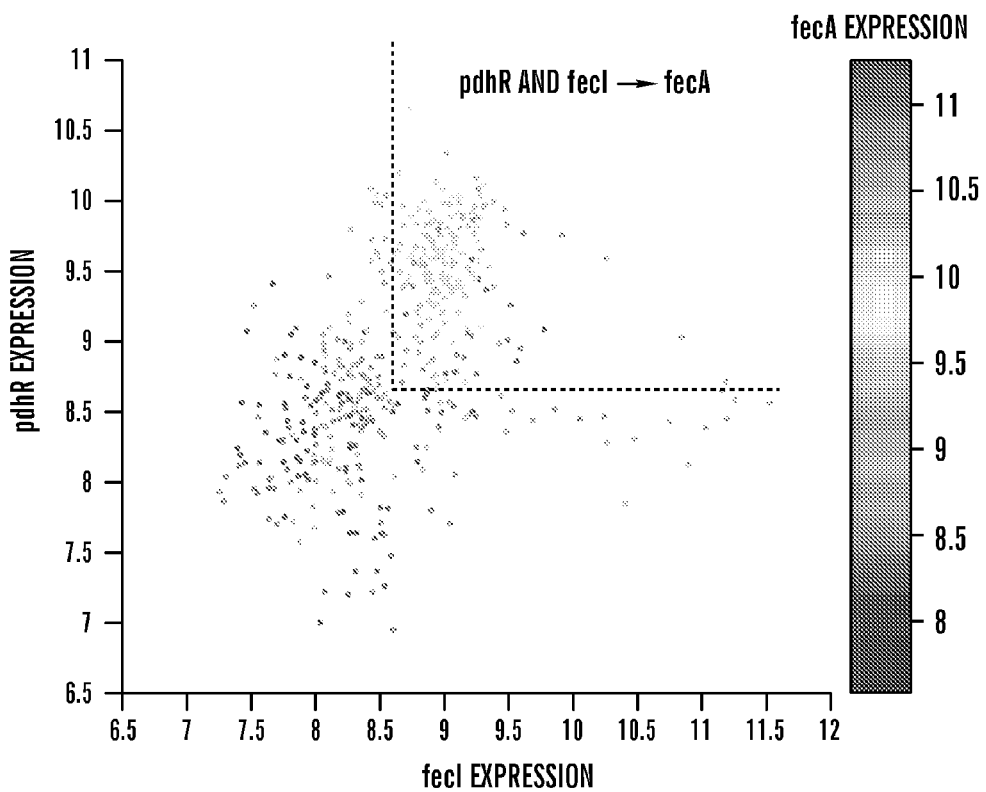
Figure 6H:
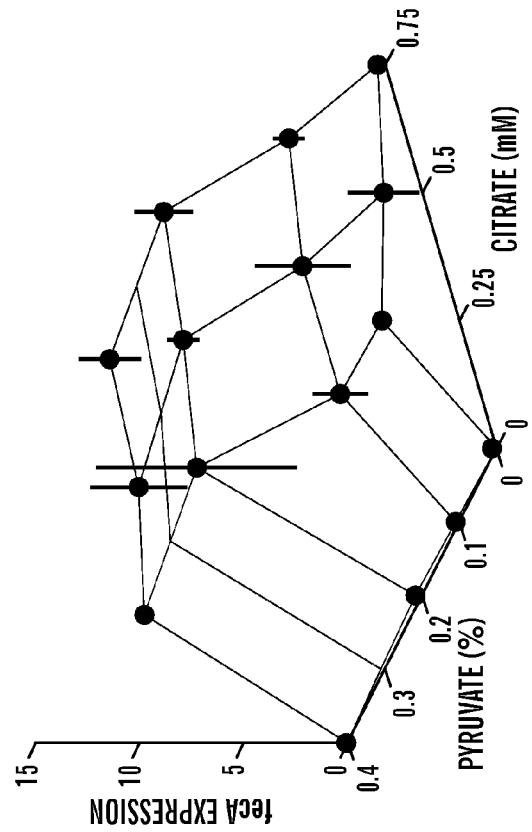
Figure 6G:
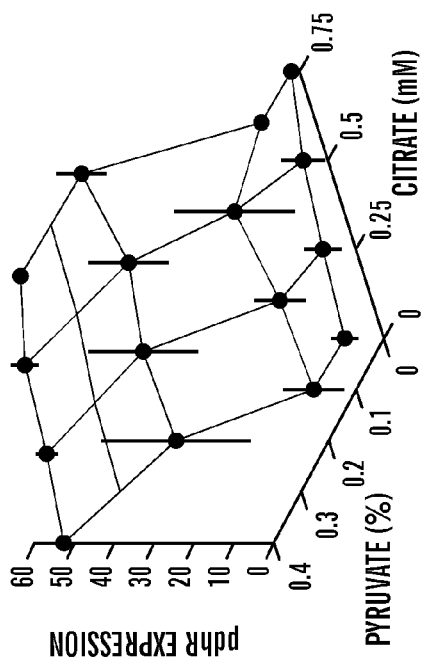
Figure 7A:
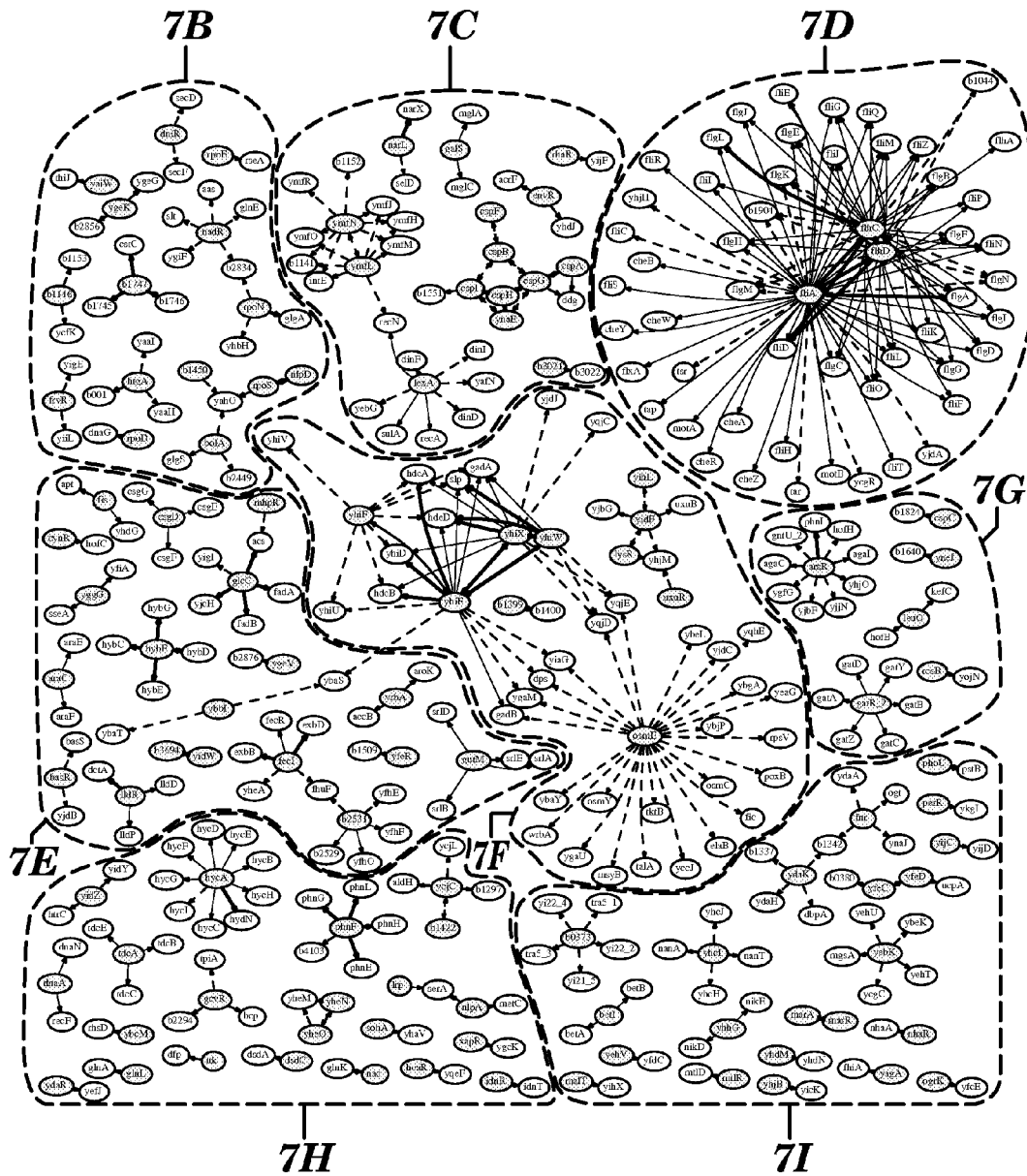
FIG. 7 shows the transcriptional regulatory map inferred by CLR with an estimated 80% accuracy. The accuracy of the network is obtained by measuring the percentage of correctly inferred edges (thin solid lines) out of all the predicted edges for genes with known connectivity (thin solid lines and bold solid lines). The solid bold line edges represent a mixture of false and novel predictions, making 80% an underestimate. The dashed line edges are to genes without a previously identified regulator or from regulators without a previously known target. Transcription factor nodes are colored light gray.
Figure 7B:
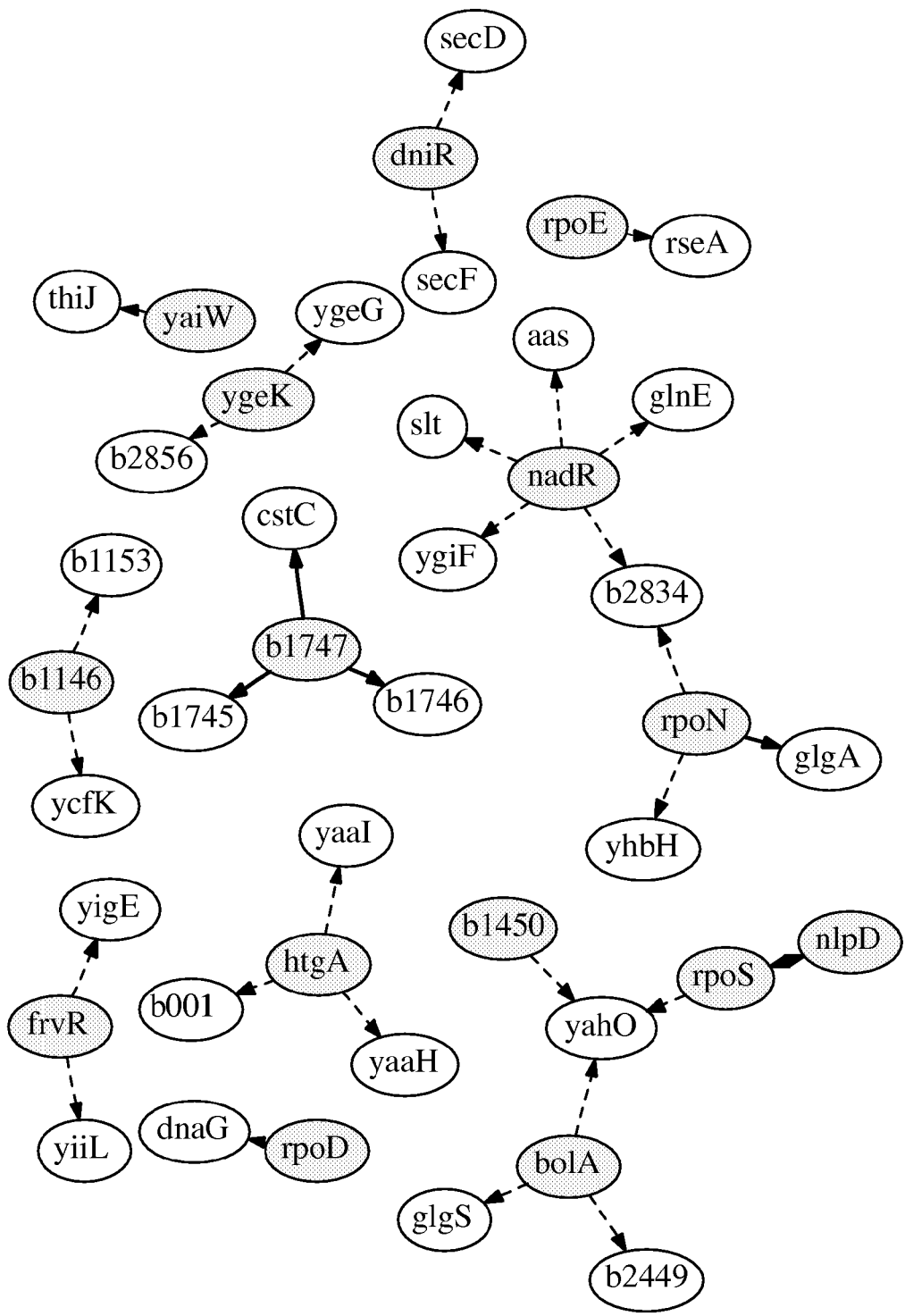
Figure 7C:
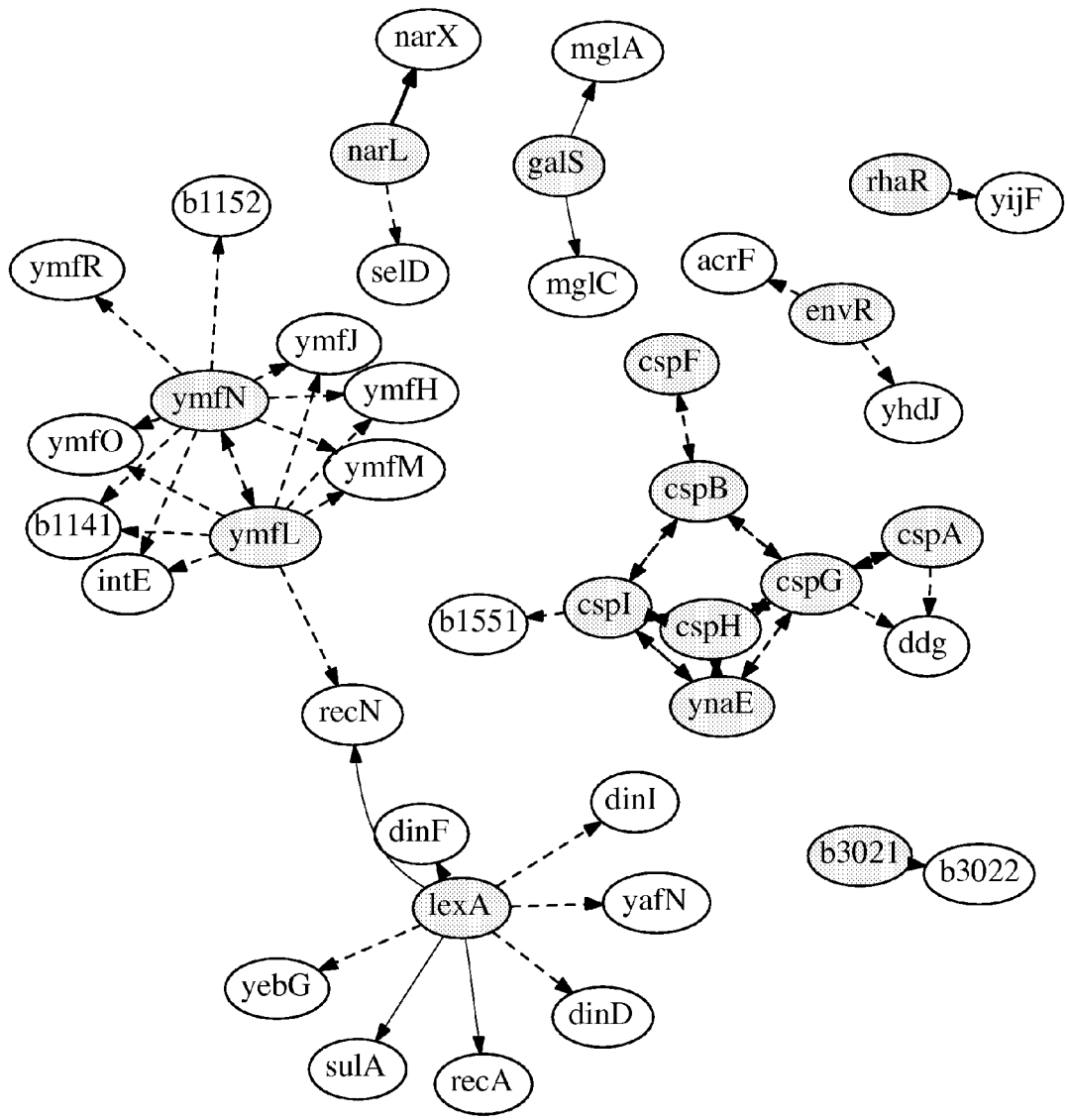
Figure 7D:
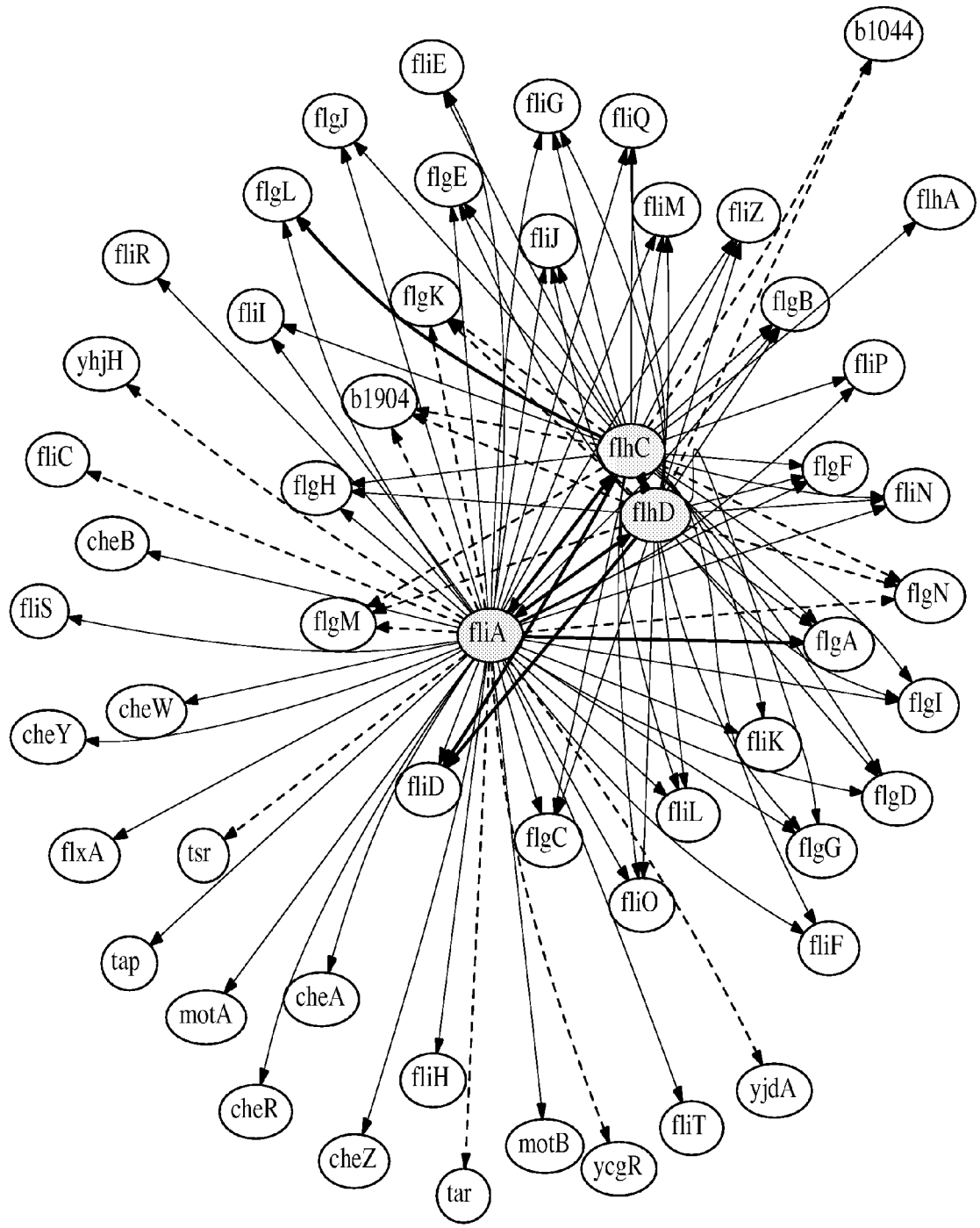
Figure 7E:
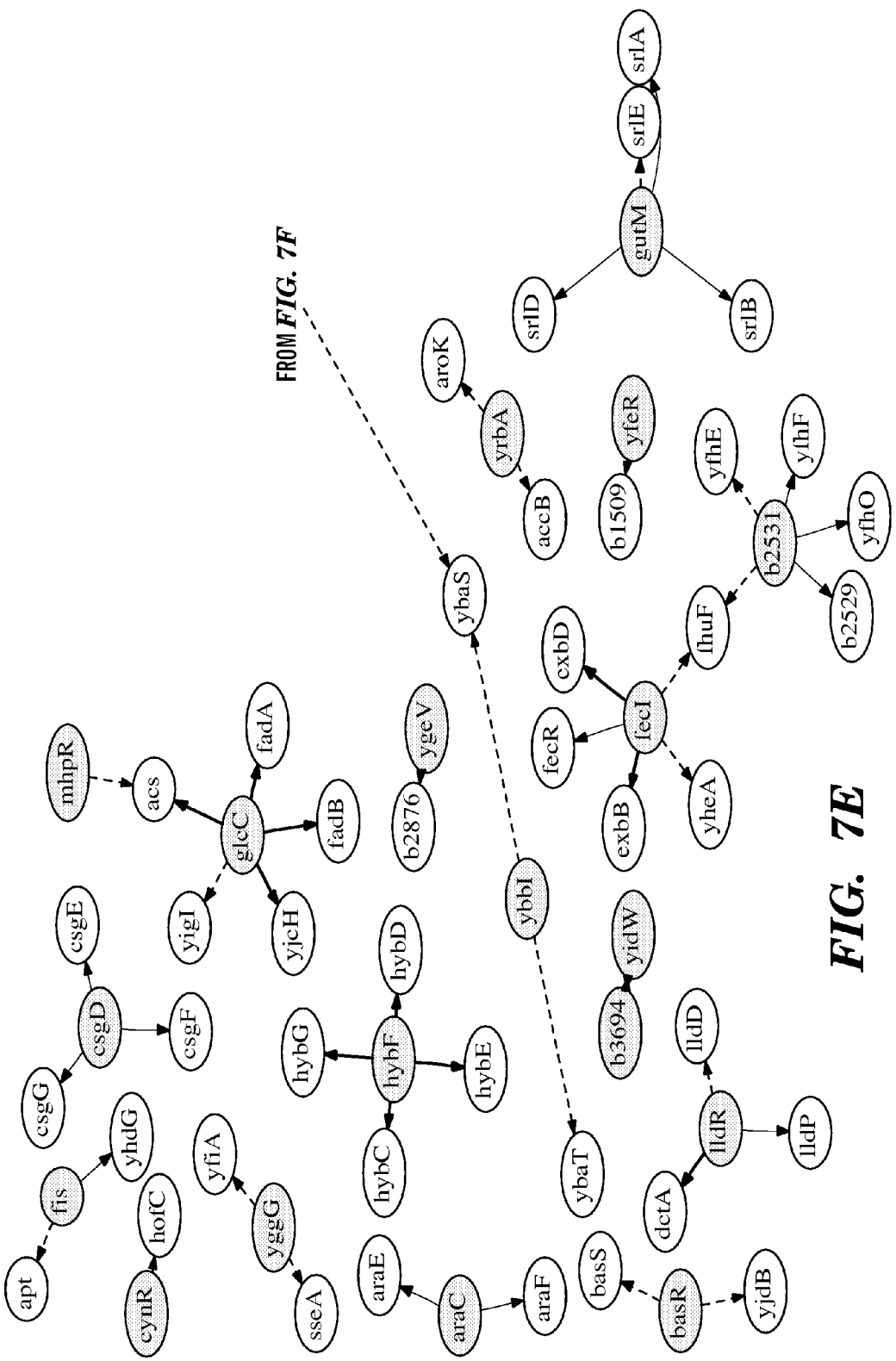
Figure 7F:
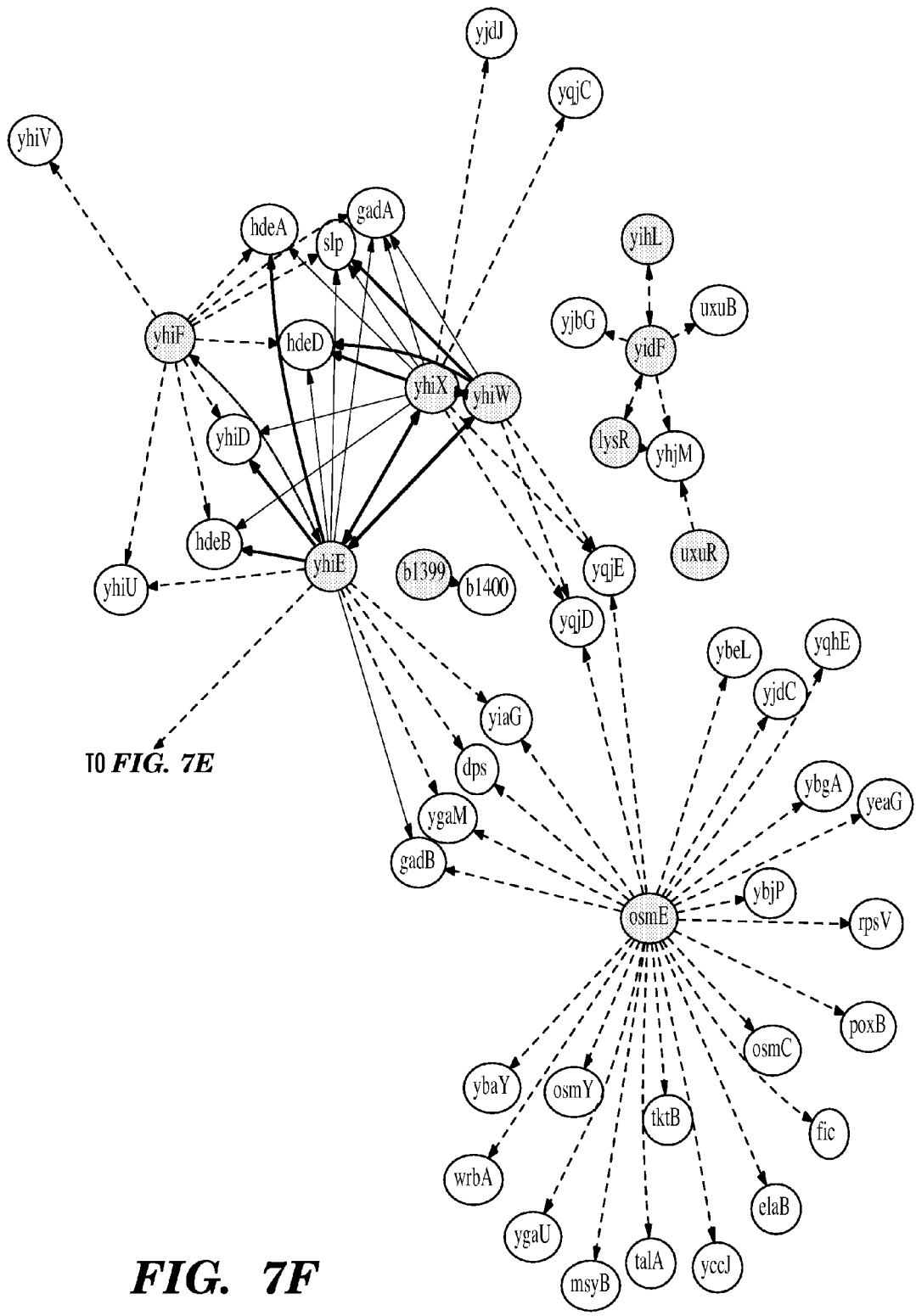
Figure 7G:
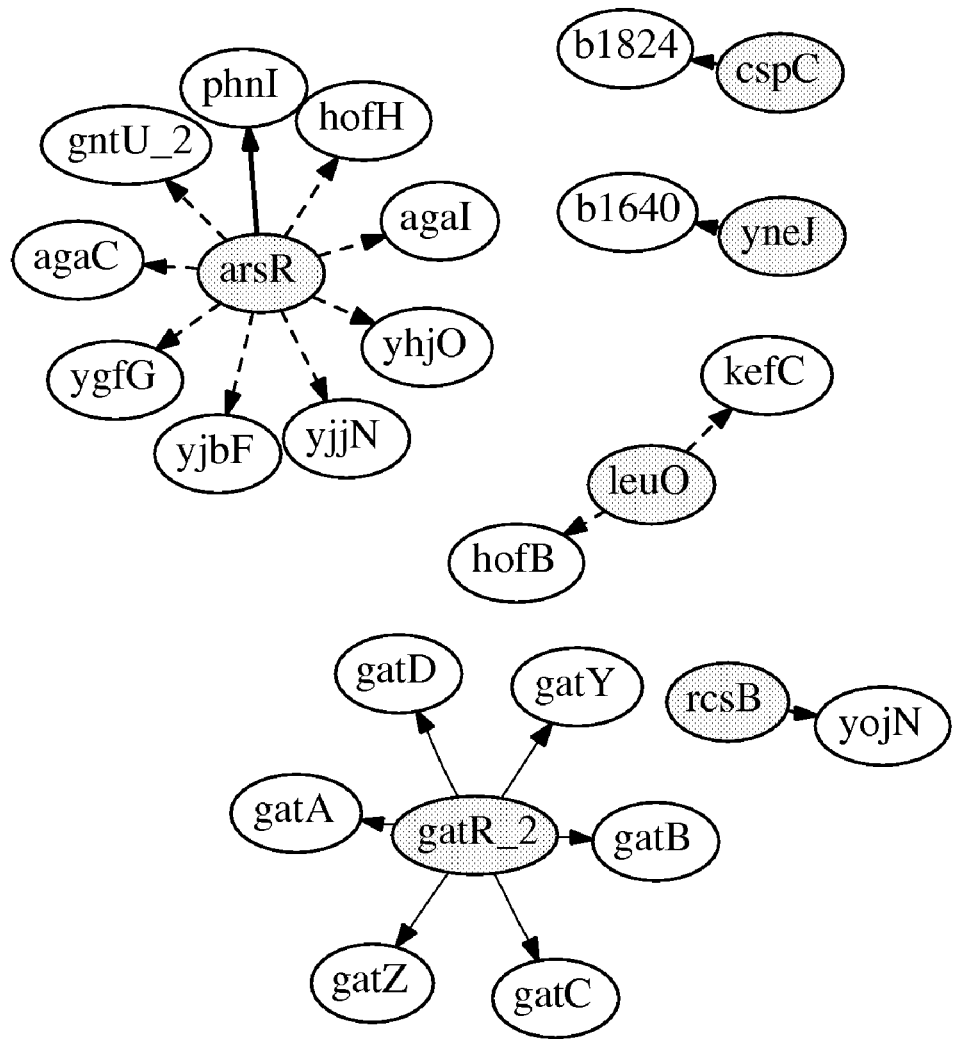
Figure 7H:
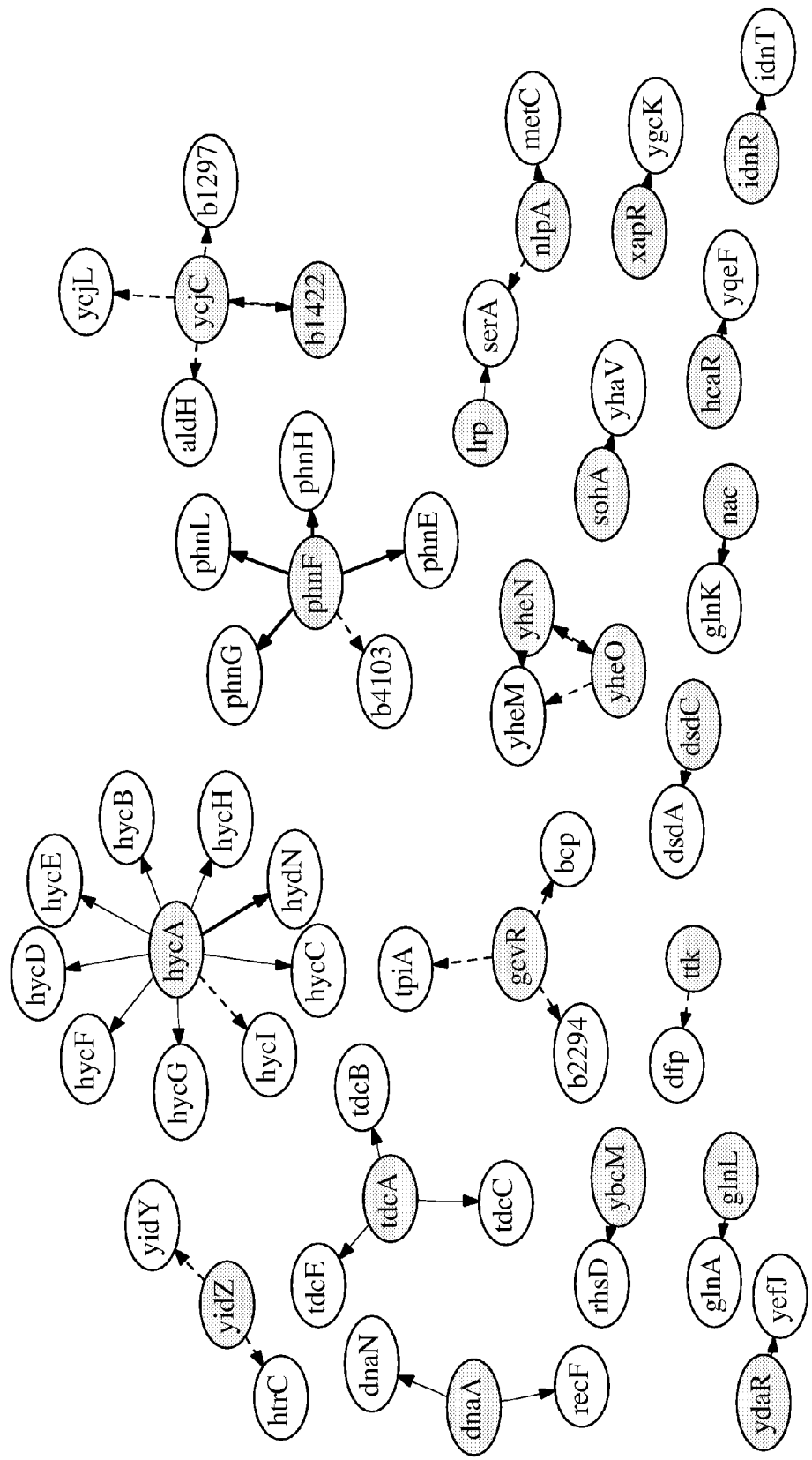
Figure 7I:
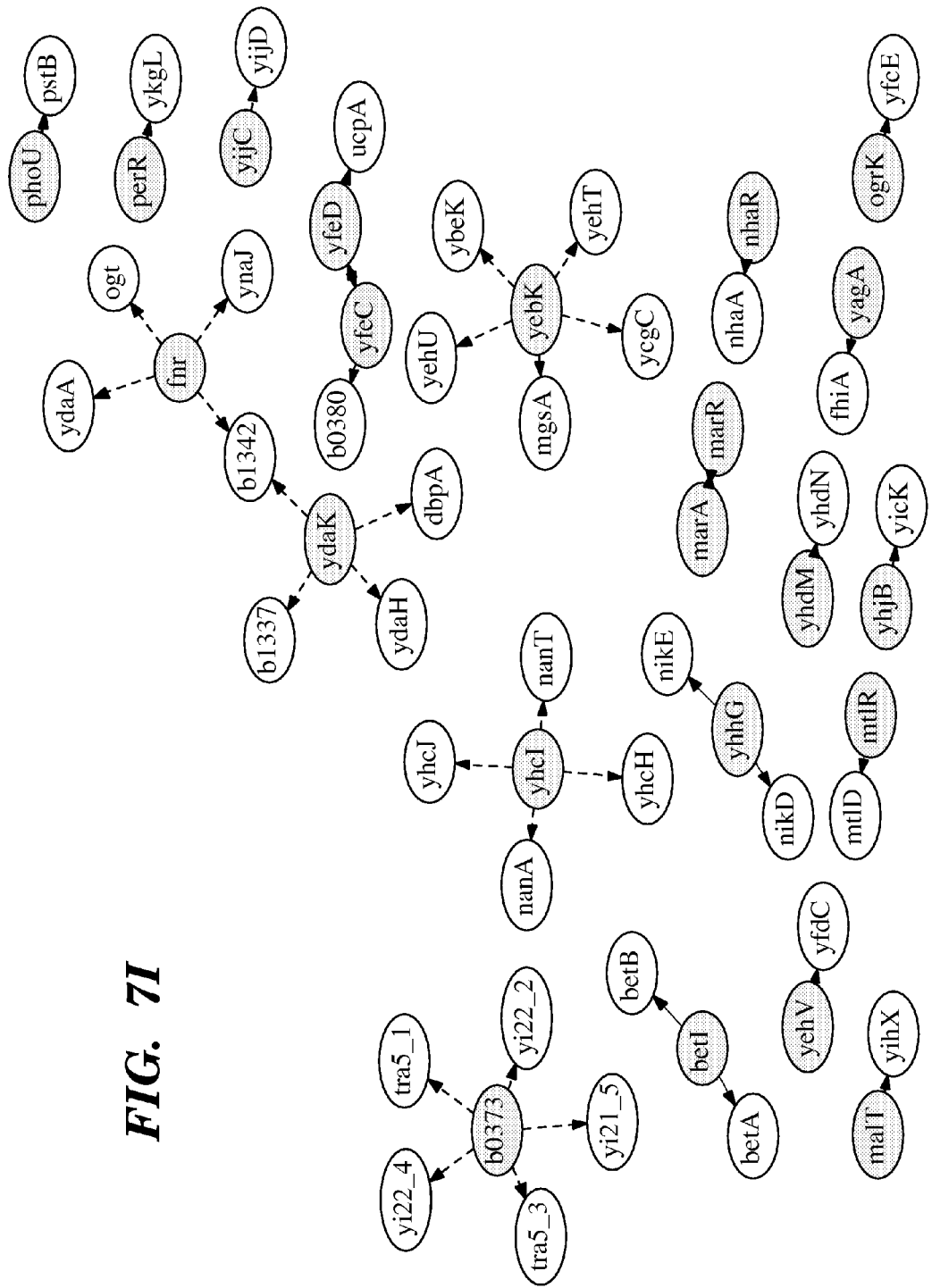

Inspection of the compendium data suggested that FecI and PdhR might regulate the fecA operon using AND-like logic, where both proteins must be activated for expression of the fecA operon (FIG. 6f). Since PdhR is a repressor that is derepressed upon binding with pyruvate, the gate is NOT (bound PdhR) AND (bound FecI) at the promoter level; self-feedback at the pdhR promoter makes the gate appear as (pdhR) AND (fed) at the level of mRNA (FIG. 6f). To test this hypothesis, we used quantitative RT-PCR to measure the expression level of fecA over 16 combinations of pyruvate (to derepress PdhR protein and induce pdhR transcription; FIG. 6g) and citrate (to activate FecI and induce fed). The fecA operon reached its highest levels of induction only when citrate and pyruvate were both present in high concentrations, supporting the hypothesis that full activation of fecA is only possible in the presence of derepressed PdhR and activated FecI (FIG. 6h).

Such an explicit regulatory link between central metabolism and iron transport has not, to the inventors' knowledge, been previously identified in microbes. This link makes sense, given that iron is a critical component of several proteins involved in both the TCA cycle (aconitase, succinate dehydrogenase) and electron transport (cytochromes, ferredoxin); the magnitude of carbon/electron flux through the citric acid cycle and electron transport chain thus plays a major role in determining the cellular need for iron. It is possible that an increase in intracellular pyruvate, which is the inducer for PdhR, may signal the need for increased flow through respiratory pathways. This novel role for pyruvate is plausible given that pyruvate serves as a common catabolite for a diverse collection of carbon sources and stands just one enzymatic step away from entering the TCA cycle itself.

The experiments described herein demonstrate the power of the CLR approach for rapid mapping of transcriptional regulation. The CLR platform, as described herein, used a novel machine-learning algorithm, combined with a compendium of 445 microarrays, to predict transcription factor-promoter interactions on a genome-wide scale in *E. coli* with over 80% accuracy. This work represents the first time such an approach has been rigorously validated in an organism at the genome scale. Moreover, it is demonstrated that one can infer an equally accurate network map using as few as 60 expression profiles.

These results also help to address persistent questions concerning the optimal design of experiments for network mapping based on machine learning: it is shown that physiological perturbations are most informative and a lower bound of 700-1000 expression profiles for the comprehensive mapping of transcriptional regulation in a prokaryote is estimated. Taken together, these results demonstrate that an informed "shotgun" approach can be applied to systematically map transcriptional regulatory networks in microbes. The approach is analogous to shotgun genome sequencing in that it uses a statistical algorithm to piece together a high quality, genome-wide map of transcriptional regulatory interactions from "random snapshots" of diverse microbial gene expression responses.

In recent years, chromatin immunoprecipitation (ChIP) techniques, particularly ChIP-chip, have offered hope for systematic characterization of transcription factor binding in vivo. But this technology, by itself, has shown high levels of false positives[26,45]. ChIP is particularly prone to errors in prokaryotes, necessitating a large number of expensive replicates[45]. Moreover, the results are condition-dependent; inactive transcription factors may not be identified because they may not bind to DNA. Finding the appropriate conditions for ChIP-chip can be costly and time-consuming, making the comprehensive mapping of microbial transcriptional networks difficult with that approach alone.

By generating a compendium of microarrays, it is demonstrated herein that it is possible to infer a high-accuracy regulatory map using fewer microarrays and simultaneously obtain rich data on condition-specific regulation. With this conditional regulatory information, one can also make a more informed decision about when a transcription factor might be active in any follow-up ChIP, mass-spectrometry, or realtime PCR experiments. Moreover, a complete genome-wide transcriptional regulatory map of a prokaryote, reconstructed using the methods described here, could be completed in months on a time scale and at a cost similar to shotgun genome sequencing.

All references cited herein are incorporated by reference herein in their entirety.

The embodiments and concrete examples of implementation discussed in the foregoing detailed explanation serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

TABLE 1

Data sources for the *Escherichia coli* microarray compendium

| Publication Title | Arrays | Conditions | Reference |
| --- | --- | --- | --- |
| this paper: Shotgun mapping of *Escherichia coli* transcriptional regulation from a compendium of expression profiles. | 266 | 121 | (Faith et al., 2006) |
| Integrating high-throughput and computational data elucidates bacterial networks | 43 | 14 | (Covert et al., 2004)[52] |
| Genome-scale analysis of the uses of the *Escherichia coli* genome: model-driven analysis of heterogeneous data sets | 41 | 20 | (Allen et al., 2003)[53] |
| Transcriptome profiles for high-cell-density recombinant and wild-type *Escherichia coli* | 32 | 10 | (Haddadin and Harcum, 2005)[54] |
| Amino acid content of recombinant proteins influences the metabolic burden response | 16 | 8 | (Bonomo and Gill, 2005)[55] |
| pH regulates genes for flagellar motility, catabolism, and oxidative stress in *Escherichia coli* K-12 | 15 | 3 | (Maurer et al., 2005)[56] |

TABLE 1-continued

Data sources for the *Escherichia coli* microarray compendium

| Publication Title | Arrays | Conditions | Reference |
|---|---|---|---|
| Genome-wide analysis of lipoprotein expression in *Escherichia coli* MG1655 | 14 | 7 | (Brokx et al., 2004)[57] |
| Genome-wide expression analysis indicates that FNR of *Escherichia coli* K-12 regulates a large number of genes of unknown function | 10 | 3 | (Kang et al., 2005)[58] |
| Global transcriptional effects of a suppressor tRNA and the inactivation of the regulator frmR. | 6 | 2 | (Herring and Blattner, 2004)[59] |
| Global transcriptional programs reveal a carbon source foraging strategy by *Escherichia coli* | 2 | 1 | (Liu et al., 2005)[60] |

TABLE 2 z-scores of motifs for transcription factors in the 60% accuracy network with >=5 predicted operon targets. Shaded rows indicate z >= 1.64 (>0.95 one-sided significance)

| Regulator | # of operons | z-score |
|---|---|---|
| alpA_b2624_at | 5 | 3.387263246 |
| araC_b0064_at | 6 | 1.644417965 |
| arsR_b3501_at | 16 | 2.777465545 |
| b0373_s_at | 6 | 5.006051233 |
| b1422_at | 5 | 0.85150075 |
| b2531_at | 5 | 4.122670786 |
| bolA_b0435_at | 5 | 1.14314888 |
| celD_b1735_at | 8 | 1.450956146 |
| cspB_61557_at | 5 | 0.448477031 |
| cspG_b0990_at | 8 | 2.057566595 |
| cspI_b1552_at | 6 | 0.273304393 |
| dnaA_b3702_at | 11 | 0.319674913 |
| feoL_b4293_at | 7 | 6.210361851 |
| fis_b3261_at | 5 | 2.437387051 |
| flhC_b1891_at | 19 | 4.048729999 |
| flhD_b1892_at | 18 | 4.804755303 |
| fliA_b1922_at | 20 | 4.894228242 |
| fnr_b1334_at | 9 | 2.277964385 |
| frvR_b3897_at | 5 | 0.406867288 |
| fucR_b2805_at | 7 | -0.363256975 |
| gcvR_b2479_at | 5 | 1.282434845 |
| glcC_b2980_at | 9 | 0.622772562 |
| htgA_b0012_at | 8 | 0.46000687 |
| hycA_b2725_at | 7 | 2.503393766 |
| leuO_b0076_at | 8 | 3.473928803 |
| lexA_b4043_at | 13 | 9.385830236 |
| lldR_b3604_at | 5 | -0.381266072 |
| lrp_b0889_at | 27 | 4.628415222 |
| mhpR_b0346_at | 13 | 5.516920577 |
| nadR_b4390_at | 6 | 2.165181711 |
| nlpA_b3661_at | 31 | 5.235463442 |
| nlpC_b1708_at | 9 | 2.209789921 |
| nlpD_b2742_at | 8 | 2.012021036 |
| osmE_b1739_at | 33 | 4.157331336 |
| phnF_b4102_at | 7 | 3.095434572 |
| rhaR_b3906_at | 9 | 0.090324961 |
| rhaS_b3905_at | 12 | 3.847389193 |
| rpoN_b3202_at | 6 | 0.127842228 |
| rstA_b1608_at | 5 | 0.479398617 |
| tdcR_b3119_at | 8 | 0.595867972 |
| ybaQ_b0483_at | 6 | 1.663430829 |
| ycjC_b1299_at | 5 | 1.257791301 |
| ydaK_b1339_at | 7 | 0.182145055 |
| ydaR_b1356_at | 5 | -0.585406198 |
| yebK_b1853_at | 11 | -0.812269943 |
| yfeC_b2398_at | 5 | 0.593218992 |
| yfeD_b2399_at | 6 | 0.233144337 |
| ygeK_b2855_at | 8 | 0.346604758 |
| yheN_b3345_at | 6 | 0.827015623 |
| yhiE_b3512_at | 20 | 3.300040018 |
| yhiF_b3507_at | 9 | 3.701055215 |
| yhiW_b3515_at | 9 | -0.094987938 |
| yhiX_b3516_at | 16 | 4.210623568 |
| yhjB_b3520_at | 10 | 2.854880879 |
| yidF_b3674_at | 9 | 0.485395684 |
| ygeK_b2855_at | 8 | 0.346604758 |
| yheN_b3345_at | 6 | 0.827015623 |
| yhiE_b3512_at | 20 | 3.300040018 |
| yhiF_b3507_at | 9 | 3.701055215 |
| yhiW_b3515_at | 9 | -0.094987938 |
| yhiX_b3516_at | 16 | 4.210623568 |
| yhjB_b3520_at | 10 | 2.854880879 |
| yidF_b3674_at | 9 | 0.485395684 |
| yidW_b3695_at | 5 | -0.472244205 |
| yihL_b3872_at | 5 | 0.876673323 |
| yjaE_b3995_at | 6 | 1.43865055 |
| yjbK_b4046_at | 10 | 1.335976907 |
| ymfL_b1147_at | 7 | 0.835709424 |
| ymfN_b1149_at | 6 | 1.785485336 |
| ynaE_b1375_s_at | 8 | 5.339348405 |
| yneJ_b1526_at | 6 | -0.414799027 |
| yrbA_b3190_at | 10 | 0.189719746 |

% significant (z >= 1.64) 48.4375

TABLE 3

Functional enrichment of YmfN targets.

| Functional category | Target Genes | p-value |
|---|---|---|
| prophage genes and phage related functions | ymfR, ymfO, ymfM, ymfL, intE | 0.0001 |
| Extrachromosomal | ymfR, ymfO, ymfM, ymfL, intE | 0.0004 |
| DNA repair | recN, dinD | 0.0029 |
| response to DNA damage stimulus | recN, dinD | 0.0029 |
| response to endogenous stimulus | recN, dinD | 0.0029 |
| response to stress | recN, dinD | 0.0081 |
| DNA related | recN, dinD | 0.01 |
| response to stimulus | recN, dinD | 0.0236 |
| DNA metabolism | recN, dinD | 0.0251 |

TABLE 4

Functional enrichment of YnaE targets.

| Functional category | Target Genes | p-value |
|---|---|---|
| response to temperature stimulus | cspI, cspG | 0.0004 |
| response to abiotic stimulus | cspI, cspG | 0.002 |
| response to stimulus | cspI, cspG | 0.0106 |

TABLE 5

The clustered microarrays of the E. coli compendium.

| Cluster | Chip name | Experiment description |
|---|---|---|
| 1 | dinI__U_N0025_r1 | dinI upregulation, amp 50 ug/ml, 0.0125% arabinose, 0.025 ug/ml norfloxacin OD ~0.3 |
| 1 | luc__U_N0000_r1 | luc upregulation, 0.000 ug/ml norfloxacin |
| 1 | luc__U_N0000_r2 | luc upregulation, 0.000 ug/ml norfloxacin |
| 1 | luc__U_N0000_r3 | luc upregulation, 0.000 ug/ml norfloxacin |
| 2 | dinI__U_N0025_r2 | dinI upregulation, amp 50 ug/ml, 0.0125% arabinose, 0.025 ug/ml norfloxacin OD ~0.3 |
| 2 | dinI__U_N0025_r3 | dinI upregulation, amp 50 ug/ml, 0.0125% arabinose, 0.025 ug/ml norfloxacin OD ~0.3 |
| 2 | dinP__U_N0025_r1 | dinP upregulation, amp 50 ug/ml, 0.0125% arabinose, 0.025 ug/ml norfloxacin OD ~0.3 |
| 2 | dinP__U_N0025_r2 | dinP upregulation, amp 50 ug/ml, 0.0125% arabinose, 0.025 ug/ml norfloxacin OD ~0.3 |
| 2 | dinP__U_N0025_r3 | dinP upregulation, amp 50 ug/ml, 0.0125% arabinose, 0.025 ug/ml norfloxacin OD ~0.3 |
| 2 | lexA__U_N0025_r1 | lexA upregulation, amp 50 ug/ml, 0.0125% arabinose, 0.025 ug/ml norfloxacin OD ~0.3 |
| 2 | lexA__U_N0025_r2 | lexA upregulation, amp 50 ug/ml, 0.0125% arabinose, 0.025 ug/ml norfloxacin OD ~0.3 |
| 2 | lexA__U_N0025_r3 | lexA upregulation, amp 50 ug/ml, 0.0125% arabinose, 0.025 ug/ml norfloxacin OD ~0.3 |
| 2 | lon__U_N0025_r1 | lon upregulation, amp 50 ug/ml, 0.0125% arabinose, 0.025 ug/ml norfloxacin OD ~0.3 |
| 2 | lon__U_N0025_r2 | Lon upregulation, amp 50 ug/ml, 0.0125% arabinose, 0.025 ug/ml norfloxacin OD ~0.3 |
| 2 | lon__U_N0025_r3 | lon upregulation, amp 50 ug/ml, 0.0125% arabinose, 0.025 ug/ml norfloxacin OD ~0.3 |
| 2 | luc__U_N0025_r1 | luc upregulation, amp 50 ug/ml, 0.0125% arabinose, 0.025 ug/ml norfloxacin OD ~0.3 |
| 2 | luc__U_N0025_r2 | luc upregulation, amp 50 ug/ml, 0.0125% arabinose, 0.025 ug/ml norfloxacin OD ~0.3 |
| 2 | luc__U_N0025_r3 | luc upregulation, amp 50 ug/ml, 0.0125% arabinose, 0.025 ug/ml norfloxacin OD ~0.3 |
| 2 | recA__U_N0025_r1 | recA upregulation, amp 50 ug/ml, 0.0125% arabinose, 0.025 ug/ml norfloxacin OD ~0.3 |
| 2 | recA__U_N0025_r2 | recA upregulation, amp 50 ug/ml, 0.0125% arabinose, 0.025 ug/ml norfloxacin OD ~0.3 |
| 2 | recA__U_N0025_r3 | recA upregulation, amp 50 ug/ml, 0.0125% arabinose, 0.025 ug/ml norfloxacin OD ~0.3 |
| 2 | ruvA__U_N0025_r1 | ruvA upregulation, amp 50 ug/ml, 0.0125% arabinose, 0.025 ug/ml norfloxacin OD ~0.3 |
| 2 | ruvA__U_N0025_r2 | ruvA upregulation, amp 50 ug/ml, 0.0125% arabinose, 0.025 ug/ml norfloxacin OD ~0.3 |
| 2 | ruvA__U_N0025_r3 | ruvA upregulation, amp 50 ug/ml, 0.0125% arabinose, 0.025 ug/ml norfloxacin OD ~0.3 |
| 2 | sulA__U_N0025_r1 | sulA upregulation, amp 50 ug/ml, 0.0125% arabinose, 0.025 ug/ml norfloxacin OD ~0.3 |
| 2 | sulA__U_N0025_r2 | sulA upregulation, amp 50 ug/ml, 0.0125% arabinose, 0.025 ug/ml norfloxacin OD ~0.3 |
| 2 | sulA__U_N0025_r3 | sulA upregulation, amp 50 ug/ml, 0.0125% arabinose, 0.025 ug/ml norfloxacin OD ~0.3 |
| 2 | umuD__U_N0025_r1 | umuD upregulation, amp 50 ug/ml, 0.0125% arabinose, 0.025 ug/ml norfloxacin OD ~0.3 |
| 2 | umuD__U_N0025_r2 | umuD upregulation, amp 50 ug/ml, 0.0125% arabinose, 0.025 ug/ml norfloxacin OD ~0.3 |
| 2 | umuD__U_N0025_r3 | umuD upregulation, amp 50 ug/ml, 0.0125% arabinose, 0.025 ug/ml norfloxacin OD ~0.3 |
| 2 | uvrA__U_N0025_r1 | uvrA upregulation, amp 50 ug/ml, 0.0125% arabinose, 0.025 ug/ml norfloxacin OD ~0.3 |
| 2 | uvrA__U_N0025_r2 | uvrA upregulation, amp 50 ug/ml, 0.0125% arabinose, 0.025 ug/ml norfloxacin OD ~0.3 |

TABLE 5-continued

The clustered microarrays of the *E. coli* compendium.

| Cluster | Chip name | Experiment description |
|---|---|---|
| 2 | uvrA__U_N0025_r3 | uvrA upregulation, amp 50 ug/ml, 0.0125% arabinose, 0.025 ug/ml norfloxacin OD ~0.3 |
| 3 | dnaA__U_N0075_r1 | dnaA upregulation, 0.075 ug/ml norfloxacin |
| 3 | gyrA__U_N0075_r1 | gyrA upregulation, 0.075 ug/mL norfloxacin |
| 3 | gyrI__U_N0075_r2 | gyrI upregulation, 0.075 ug/mL norfloxacin |
| 3 | minD__U_N0075_r1 | minD upregulation, 0.075 ug/mL norfloxacin |
| 3 | murI__U_N0075_r1 | murI upregulation, 0.075 ug/mL norfloxacin |
| 3 | rstB__U_N0075_r1 | rstB upregulation, 0.075 ug/mL norfloxacin |
| 3 | uspA__U_N0075_r1 | uspA upregulation, 0.075 ug/mL norfloxacin |
| 4 | dnaA__U_N0075_r2 | dnaA upregulation, 0.075 ug/ml norfloxacin |
| 4 | gyrI__U_N0075_r1 | gyrI upregulation, 0.075 ug/mL norfloxacin |
| 4 | menB__U_N0075_r1 | menB upregulation, 0.075 ug/mL norfloxacin |
| 5 | dnaN__U_N0075_r1 | dnaN upregulation, 0.075 ug/ml norfloxacin |
| 5 | dnaT__U_N0075_r1 | dnaT upregulation, 0.075 ug/ml norfloxacin |
| 5 | sbcB__U_N0075_r1 | sbcB upregulation, 0.075 ug/mL norfloxacin |
| 6 | dnaN__U_N0075_r2 | dnaN upregulation, 0.075 ug/ml norfloxacin |
| 6 | dnaT__U_N0075_r2 | dnaT upregulation, 0.075 ug/ml norfloxacin |
| 6 | hscA__U_N0075_r2 | hscA upregulation, 0.075 ug/mL norfloxacin |
| 6 | minE__U_N0075_r2 | minE upregulation, 0.075 ug/mL norfloxacin |
| 6 | murI__U_N0075_r2 | murI upregulation, 0.075 ug/mL norfloxacin |
| 6 | sbcB__U_N0075_r2 | sbcB upregulation, 0.075 ug/mL norfloxacin |
| 7 | emrR__U_N0075_r1 | emrR upregulation, 0.075 ug/ml norfloxacin |
| 7 | holD__U_N0075_r1 | holD upregulation, 0.075 ug/mL norfloxacin |
| 7 | hscA__U_N0075_r1 | hscA upregulation, 0.075 ug/mL norfloxacin |
| 7 | IHF__U_N0075_r1 | IHF upregulation, 0.075 ug/mL norfloxacin |
| 7 | minE__U_N0075_r1 | minE upregulation, 0.075 ug/mL norfloxacin |
| 7 | nrdA__U_N0075_r1 | nrdA upregulation, 0.075 ug/mL norfloxacin |
| 7 | nrdB__U_N0075_r1 | nrdB upregulation, 0.075 ug/mL norfloxacin |
| 8 | emrR__U_N0075_r3 | emrR upregulation, 0.075 ug/mL norfloxacin |
| 8 | hlpA__U_N0075_r2 | hlpA upregulation, 0.075 ug/mL norfloxacin |
| 8 | holD__U_N0075_r2 | holD upregulation, 0.075 ug/mL norfloxacin |
| 8 | hscA__U_N0075_r3 | hscA upregulation, 0.075 ug/mL norfloxacin |
| 8 | IHF__U_N0075_r3 | IHF upregulation, 0.075 ug/mL norfloxacin |
| 8 | nrdA__U_N0075_r3 | nrdA upregulation, 0.075 ug/mL norfloxacin |
| 8 | nrdB__U_N0075_r3 | nrdB upregulation, 0.075 ug/mL norfloxacin |
| 8 | ruvC__U_N0075_r1 | ruvC upregulation, 0.075 ug/mL norfloxacin |
| 9 | folA__U_N0075_r2 | folA upregulation, 0.075 ug/ml norfloxacin |
| 9 | menC__U_N0075_r2 | menC upregulation, 0.075 ug/mL norfloxacin |
| 10 | galF__U_N0075_r1 | galF upregulation, 0.075 ug/ml norfloxacin |
| 10 | hlpA__U_N0075_r1 | hlpA upregulation, 0.075 ug/mL norfloxacin |
| 10 | menC__U_N0075_r3 | menC upregulation, 0.075 ug/mL norfloxacin |
| 11 | galF__U_N0075_r2 | galF upregulation, 0.075 ug/ml norfloxacin |
| 11 | nupC__U_N0075_r2 | nupC upregulation, 0.075 ug/mL norfloxacin |
| 12 | gcvR__U_N0075_r1 | gcvR upregulation, 0.075 ug/mL norfloxacin |
| 12 | gyrI__U_N0075_r3 | gyrI upregulation, 0.075 ug/mL norfloxacin |
| 12 | holD__U_N0075_r3 | holD upregulation, 0.075 ug/mL norfloxacin |
| 12 | minD__U_N0075_r3 | minD upregulation, 0.075 ug/mL norfloxacin |
| 12 | murI__U_N0075_r3 | murI upregulation, 0.075 ug/mL norfloxacin |
| 12 | rimI__U_N0075_r1 | rimI upregulation, 0.075 ug/mL norfloxacin |
| 12 | rimI__U_N0075_r3 | rimI upregulation, 0.075 ug/mL norfloxacin |
| 12 | rstB__U_N0075_r3 | rstB upregulation, 0.075 ug/mL norfloxacin |
| 12 | ruvC__U_N0075_r3 | ruvC upregulation, 0.075 ug/mL norfloxacin |
| 12 | sbcB__U_N0075_r3 | sbcB upregulation, 0.075 ug/mL norfloxacin |
| 13 | menC__U_N0075_r1 | menC upregulation, 0.075 ug/mL norfloxacin |
| 13 | minD__U_N0075_r2 | minD upregulation, 0.075 ug/mL norfloxacin |
| 14 | yoeB__U_N0075_r1 | yoeB upregulation, 0.075 ug/mL norfloxacin |
| 14 | yoeB__U_N0075_r2 | yoeB upregulation, 0.075 ug/mL norfloxacin |
| 14 | yoeB__U_N0075_r3 | yoeB upregulation, 0.075 ug/mL norfloxacin |
| 15 | nupC__U_N0075_r3 | nupC upregulation, 0.075 ug/mL norfloxacin |
| 16 | mazF__U_N0025_r1 | mazF_chpA upregulation, amp 50 ug/ml, 0.0125% arabinose, 0.025 ug/ml norfloxacin OD ~0.3 |
| 16 | mazF__U_N0025_r2 | mazF_chpA upregulation, amp 50 ug/ml, 0.0125% arabinose, 0.025 ug/ml norfloxacin OD ~0.3 |
| 16 | mazF__U_N0025_r3 | mazF_chpA upregulation, amp 50 ug/ml, 0.0125% arabinose, 0.025 ug/ml norfloxacin OD ~0.3 |
| 16 | relE__U_N0025_r1 | relE upregulation, amp 50 ug/ml, 0.0125% arabinose, 0.025 ug/ml norfloxacin OD ~0.3 |
| 16 | relE__U_N0025_r2 | relE upregulation, amp 50 ug/ml, 0.0125% arabinose, 0.025 ug/ml norfloxacin OD ~0.3 |
| 16 | relE__U_N0025_r3 | relE upregulation, amp 50 ug/ml, 0.0125% arabinose, 0.025 ug/ml norfloxacin OD ~0.3 |
| 17 | WT_N0000_r1 | wild-type cells without norfloxacin |
| 17 | WT_N0000_r2 | wild-type cells without norfloxacin |
| 17 | WT_N0025_r1 | wild-type cells with 0.025 ug/ml norfloxacin |
| 17 | WT_N0025_r2 | wild-type cells with 0.025 ug/ml norfloxacin |
| 17 | WT_N0050_r1 | wild-type cells with 0.050 ug/ml norfloxacin |

TABLE 5-continued

The clustered microarrays of the *E. coli* compendium.

| Cluster | Chip name | Experiment description |
|---|---|---|
| 17 | WT_N0050_r2 | wild-type cells with 0.050 ug/ml norfloxacin |
| 18 | WT_N0075_r1 | wild-type cells with 0.075 ug/ml norfloxacin |
| 18 | WT_N0075_r2 | wild-type cells with 0.075 ug/ml norfloxacin |
| 19 | recA_D_N0000_r1 | recA deletion 0 ug/ml norfloxacin |
| 19 | recA_D_N0000_r2 | recA deletion 0 ug/ml norfloxacin |
| 19 | recA_D_N0050_r1 | recA deletion 0.05 ug/ml norfloxacin |
| 19 | recA_D_N0050_r2 | recA deletion 0.05 ug/ml norfloxacin |
| 19 | recA_D_N1000_r1 | recA deletion 1.0 ug/ml norfloxacin |
| 19 | recA_D_N1000_r2 | recA deletion 1.0 ug/ml norfloxacin |
| 19 | WT_D_N1000_r1 | wild-type 1.0 ug/ml norfloxacin |
| 19 | WT_D_N1000_r2 | wild-type 1.0 ug/ml norfloxacin |
| 20 | luc2_U_N0025_r1 | luciferase 0.025 ug/ml norfloxacin |
| 20 | luc2_U_N0000_r1 | luciferase no drug |
| 21 | luc2_U_N0025_r2 | luciferase 0.025 ug/ml norfloxacin |
| 21 | luc2_U_N0000_r2 | luciferase no drug |
| 22 | T0_N0025_r1 | cells prior to treatment by norfloxacin |
| 22 | T0_N0025_r2 | cells prior to treatment by norfloxacin |
| 22 | T0_N0025_r3 | cells prior to treatment by norfloxacin |
| 23 | T12_N0025_r1 | cells 12 min after treatment by norfloxacin |
| 23 | T12_N0025_r2 | cells 12 min after treatment by norfloxacin |
| 23 | T12_N0025_r3 | cells 12 min after treatment by norfloxacin |
| 23 | T24_N0025_r1 | cells 24 min after treatment by norfloxacin |
| 23 | T24_N0025_r2 | cells 24 min after treatment by norfloxacin |
| 23 | T24_N0025_r3 | cells 24 min after treatment by norfloxacin |
| 23 | T36_N0025_r1 | cells 36 min after treatment by norfloxacin |
| 23 | T36_N0025_r2 | cells 36 min after treatment by norfloxacin |
| 23 | T36_N0025_r3 | cells 36 min after treatment by norfloxacin |
| 23 | T48_N0025_r1 | cells 48 min after treatment by norfloxacin |
| 23 | T48_N0025_r2 | cells 48 min after treatment by norfloxacin |
| 23 | T48_N0025_r3 | cells 48 min after treatment by norfloxacin |
| 23 | T60_N0025_r1 | cells 60 min after treatment by norfloxacin |
| 23 | T60_N0025_r2 | cells 60 min after treatment by norfloxacin |
| 23 | T60_N0025_r3 | cells 60 min after treatment by norfloxacin |
| 24 | T24_N0000_r1 | untreated cells after 24 min |
| 24 | T24_N0000_r2 | untreated cells after 24 min |
| 24 | T24_N0000_r3 | untreated cells after 24 min |
| 24 | T60_N0000_r1 | untreated cells after 60 min |
| 24 | T60_N0000_r2 | untreated cells after 60 min |
| 24 | T60_N0000_r3 | untreated cells after 60 min |
| 25 | ccdB_K12_0_r1 | *E. coli* K12 with ccdB upregulation 0 minutes after induction |
| 25 | lacZ_K12_0_r1 | *E. coli* K12 with lacZ upregulation 0 minutes after induction |
| 26 | ccdB_K12_30_r1 | *E. coli* K12 with ccdB upregulation 30 minutes after induction |
| 26 | ccdB_K12_60_r1 | *E. coli* K12 with ccdB upregulation 60 minutes after induction |
| 26 | lacZ_K12_30_r1 | *E. coli* K12 with lacZ upregulation 30 minutes after induction |
| 26 | lacZ_K12_60_r1 | *E. coli* K12 with lacZ upregulation 60 minutes after induction |
| 27 | ccdB_K12_90_r1 | *E. coli* K12 with ccdB upregulation 90 minutes after induction |
| 27 | ccdB_K12_120_r1 | *E. coli* K12 with ccdB upregulation 120 minutes after induction |
| 28 | lacZ_K12_90_r1 | *E. coli* K12 with lacZ upregulation 90 minutes after induction |
| 28 | lacZ_K12_120_r1 | *E. coli* K12 with lacZ upregulation 120 minutes after induction |
| 29 | lacZ_MG1063_0_r1 | *E. coli* MG1063 (recA56 = recA-) with lacZ upregulation 0 minutes after induction |
| 29 | lacZ_MG1063_30_r1 | *E. coli* MG1063 (recA56 = recA-) with lacZ upregulation 30 minutes after induction |
| 29 | lacZ_MG1063_60_r1 | *E. coli* MG1063 (recA56 = recA-) with lacZ upregulation 60 minutes after induction |
| 29 | lacZ_MG1063_90_r1 | *E. coli* MG1063 (recA56 = recA-) with lacZ upregulation 90 minutes after induction |
| 29 | ccdB_MG1063_0_r1 | *E. coli* MG1063 (recA56 = recA-) with ccdB upregulation 0 minutes after induction |
| 29 | ccdB_MG1063_30_r1 | *E. coli* MG1063 (recA56 = recA-) with ccdB upregulation 30 minutes after induction |
| 29 | ccdB_MG1063_60_r1 | *E. coli* MG1063 (recA56 = recA-) with ccdB upregulation 60 minutes after induction |
| 29 | lacZ_MG1063_0_r2 | *E. coli* MG1063 (recA56 = recA-) with lacZ upregulation 0 minutes after induction |
| 29 | lacZ_MG1063_30_r2 | *E. coli* MG1063 (recA56 = recA-) with lacZ upregulation 30 minutes after induction |
| 29 | lacZ_MG1063_60_r2 | *E. coli* MG1063 (recA56 = recA-) with lacZ upregulation 60 minutes after induction |
| 29 | lacZ_MG1063_90_r2 | *E. coli* MG1063 (recA56 = recA-) with lacZ upregulation 90 minutes after induction |
| 29 | lacZ_MG1063_120_r1 | *E. coli* MG1063 (recA56 = recA-) with lacZ upregulation 120 minutes after induction |

TABLE 5-continued

The clustered microarrays of the *E. coli* compendium.

| Cluster | Chip name | Experiment description |
|---|---|---|
| 29 | ccdB_MG1063_0_r2 | *E. coli* MG1063 (recA56 = recA-) with ccdB upregulation 0 minutes after induction |
| 29 | ccdB_MG1063_30_r2 | *E. coli* MG1063 (recA56 = recA-) with ccdB upregulation 30 minutes after induction |
| 29 | ccdB_MG1063_60_r2 | *E. coli* MG1063 (recA56 = recA-) with ccdB upregulation 60 minutes after induction |
| 30 | ccdB_MG1063_90_r1 | *E. coli* MG1063 (recA56 = recA-) with ccdB upregulation 90 minutes after induction |
| 30 | ccdB_MG1063_90_r2 | *E. coli* MG1063 (recA56 = recA-) with ccdB upregulation 90 minutes after induction |
| 30 | ccdB_MG1063_120_r1 | *E. coli* MG1063 (recA56 = recA-) with ccdB upregulation 120 minutes after induction |
| 31 | lacZ_W1863_0_r1 | *E. coli* W1863 wt lambda- with lacZ upregulation 0 minutes after induction |
| 31 | ph5_r1 | strain K12 in LB pH adjusted to 5 with KOH and buffered with HOMOPIPES |
| 31 | ph5_r2 | strain K12 in LB pH adjusted to 5 with KOH and buffered with HOMOPIPES |
| 31 | ph5_r3 | strain K12 in LB pH adjusted to 5 with KOH and buffered with HOMOPIPES |
| 31 | ph5_r4 | strain K12 in LB pH adjusted to 5 with KOH and buffered with HOMOPIPES |
| 31 | ph5_r5 | strain K12 in LB pH adjusted to 5 with KOH and buffered with HOMOPIPES |
| 31 | ph7_r1 | strain K12 in LB pH adjusted to 7 with KOH and buffered with HOMOPIPES |
| 31 | ph7_r2 | strain K12 in LB pH adjusted to 7 with KOH and buffered with HOMOPIPES |
| 31 | ph7_r3 | strain K12 in LB pH adjusted to 7 with KOH and buffered with HOMOPIPES |
| 31 | ph7_r4 | strain K12 in LB pH adjusted to 7 with KOH and buffered with HOMOPIPES |
| 31 | ph7_r5 | strain K12 in LB pH adjusted to 7 with KOH and buffered with HOMOPIPES |
| 31 | ph8.7_r1 | strain K12 in LB pH adjusted to 8.7 with KOH and buffered with HOMOPIPES |
| 31 | ph8.7_r2 | strain K12 in LB pH adjusted to 8.7 with KOH and buffered with HOMOPIPES |
| 31 | ph8.7_r3 | strain K12 in LB pH adjusted to 8.7 with KOH and buffered with HOMOPIPES |
| 31 | ph8.7_r4 | strain K12 in LB pH adjusted to 8.7 with KOH and buffered with HOMOPIPES |
| 31 | ph8.7_r5 | strain K12 in LB pH adjusted to 8.7 with KOH and buffered with HOMOPIPES |
| 32 | lacZ_W1863_30_r1 | *E. coli* W1863 wt lambda- with lacZ upregulation 30 minutes after induction |
| 32 | lacZ_W1863_60_r1 | *E. coli* W1863 wt lambda- with lacZ upregulation 60 minutes after induction |
| 32 | ccdB_W1863_0_r1 | *E. coli* W1863 wt lambda- with ccdB upregulation 0 minutes after induction |
| 32 | ccdB_W1863_30_r1 | *E. coli* W1863 wt lambda- with ccdB upregulation 30 minutes after induction |
| 33 | lacZ_W1863_90_r1 | *E. coli* W1863 wt lambda- with lacZ upregulation 90 minutes after induction |
| 33 | ccdB_W1863_60_r1 | *E. coli* W1863 wt lambda- with ccdB upregulation 60 minutes after induction |
| 33 | ccdB_W1863_90_r1 | *E. coli* W1863 wt lambda- with ccdB upregulation 90 minutes after induction |
| 34 | appY_KO9_r1 | aerobic growth of appY knock-out strain on M9 media with glucose |
| 34 | appY_KO9_r2 | aerobic growth of appY knock-out strain on M9 media with glucose |
| 34 | arcA_KO9_r1 | aerobic growth of arcA knock-out strain on M9 media with glucose |
| 34 | arcA_KO9_r2 | aerobic growth of arcA knock-out strain on M9 media with glucose |
| 34 | arcA_KO9_r3 | aerobic growth of arcA knock-out strain on M9 media with glucose |
| 34 | arcAfnr_KO9_r1 | aerobic growth of arcA/fnr double knock-out strain on M9 media with glucose |
| 34 | arcAfnr_KO9_r2 | aerobic growth of arcA/fnr double knock-out strain on M9 media with glucose |
| 34 | arcAfnr_KO9_r3 | aerobic growth of arcA/fnr double knock-out strain on M9 media with glucose |
| 34 | fnr_KO9_r1 | aerobic growth of fnr knock-out strain on M9 media with glucose |

TABLE 5-continued

The clustered microarrays of the *E. coli* compendium.

| Cluster | Chip name | Experiment description |
|---|---|---|
| 34 | fnr_KO9_r2 | aerobic growth of fnr knock-out strain on M9 media with glucose |
| 34 | fnr_KO9_r3 | aerobic growth of fnr knock-out strain on M9 media with glucose |
| 34 | oxyR_KO9_r1 | aerobic growth of oxyR knock-out strain on M9 media with glucose |
| 34 | oxyR_KO9_r2 | aerobic growth of oxyR knock-out strain on M9 media with glucose |
| 34 | oxyR_KO9_r3 | aerobic growth of oxyR knock-out strain on M9 media with glucose |
| 34 | soxS_KO9_r1 | aerobic growth of soxS knock-out strain on M9 media with glucose |
| 34 | soxS_KO9_r2 | aerobic growth of soxS knock-out strain on M9 media with glucose |
| 34 | soxS_KO9_r3 | aerobic growth of soxS knock-out strain on M9 media with glucose |
| 34 | WT_O9_r1 | aerobic aerobic growth of wild-type strain on M9 media with glucose |
| 34 | WT_O9_r2 | aerobic aerobic growth of wild-type strain on M9 media with glucose |
| 34 | WT_O9_r3 | aerobic aerobic growth of wild-type strain on M9 media with glucose |
| 34 | arcA_KN9_r1 | anaerobic growth of arcA knock-out strain on M9 media with glucose |
| 34 | arcA_KN9_r2 | anaerobic growth of arcA knock-out strain on M9 media with glucose |
| 34 | arcA_KN9_r3 | anaerobic growth of arcA knock-out strain on M9 media with glucose |
| 34 | arcAfnr_KN9_r1 | anaerobic growth of arcA/fnr double knock-out strain on M9 media with glucose |
| 34 | arcAfnr_KN9_r2 | anaerobic growth of arcA/fnr double knock-out strain on M9 media with glucose |
| 34 | arcAfnr_KN9_r3 | anaerobic growth of arcA/fnr double knock-out strain on M9 media with glucose |
| 35 | appY_KO9_r3 | aerobic growth of appY knock-out strain on M9 media with glucose |
| 35 | fnr_KN9_r1 | anaerobic growth of fnr knock-out strain on M9 media with glucose |
| 35 | cybr_N_stat_r1 | BW30270 stationary phase, anaerobic on MOPS minimal media with glucose |
| 35 | cybr_N_stat_r2 | BW30270 stationary phase, anaerobic on MOPS minimal media with glucose |
| 36 | appY_KN9_r1 | anaerobic growth of appY knock-out strain on M9 media with glucose |
| 36 | appY_KN9_r2 | anaerobic growth of appY knock-out strain on M9 media with glucose |
| 36 | appY_KN9_r3 | anaerobic growth of appY knock-out strain on M9 media with glucose |
| 36 | fnr_KN9_r2 | anaerobic growth of fnr knock-out strain on M9 media with glucose |
| 36 | fnr_KN9_r3 | anaerobic growth of fnr knock-out strain on M9 media with glucose |
| 36 | oxyR_KN9_r1 | anaerobic growth of oxyR knock-out strain on M9 media with glucose |
| 36 | oxyR_KN9_r2 | anaerobic growth of oxyR knock-out strain on M9 media with glucose |
| 36 | oxyR_KN9_r3 | anaerobic growth of oxyR knock-out strain on M9 media with glucose |
| 36 | soxS_KN9_r1 | anaerobic growth of soxS knock-out strain on M9 media with glucose |
| 36 | soxS_KN9_r2 | anaerobic growth of soxS knock-out strain on M9 media with glucose |
| 36 | soxS_KN9_r3 | anaerobic growth of soxS knock-out strain on M9 media with glucose |
| 36 | WT_N9_r1 | anaerobic growth of wild-type strain on M9 media with glucose |
| 36 | WT_N9_r2 | anaerobic growth of wild-type strain on M9 media with glucose |
| 36 | WT_N9_r3 | anaerobic growth of wild-type strain on M9 media with glucose |
| 36 | WT_N9_r4 | anaerobic growth of wild-type strain on M9 media with glucose |
| 37 | yebF__U_N0075_r1 | yebF upregulation, 0.075 ug/ml norfloxacin |
| 37 | yebF__U_N0075_r3 | yebF upregulation, 0.075 ug/ml norfloxacin |
| 38 | yebF__U_N0075_r2 | yebF upregulation, 0.075 ug/ml norfloxacin |
| 38 | dam__U_N0075_r2 | dam upregulation, 0.075 ug/ml norfloxacin |

TABLE 5-continued

The clustered microarrays of the *E. coli* compendium.

| Cluster | Chip name | Experiment description |
|---|---|---|
| 39 | WT_OPG_r1 | aerobic growth wild-type cells OD 0.2 on MOPS media with glucose |
| 39 | ast_pBADsup2_r1 | MG1655 OD 0.2 on MOPS media with arabinose controlled induction of an amber suppressor tRNA |
| 39 | ast_pBADsup2_r2 | MG1655 OD 0.2 on MOPS media with arabinose controlled induction of an amber suppressor tRNA |
| 39 | ast_pBADsup2_r3 | MG1655 OD 0.2 on MOPS media with arabinose controlled induction of an amber suppressor tRNA |
| 39 | ast_pBAD18_r1 | MG1655 OD 0.2 on MOPS media with empty pBAD18 vector |
| 39 | ast_pBAD18_r2 | MG1655 OD 0.2 on MOPS media with empty pBAD18 vector |
| 39 | ast_pBAD18_r3 | MG1655 OD 0.2 on MOPS media with empty pBAD18 vector |
| 39 | cybr_O_r1 | MG1655 log phase, aerobic on MOPS minimal media with glucose |
| 39 | cybr_O_r2 | MG1655 log phase, aerobic on MOPS minimal media with glucose |
| 39 | cybr_O_log_r1 | BW30270 log phase, aerobic on MOPS minimal media with glucose |
| 39 | cybr_O_log_r2 | BW30270 log phase, aerobic on MOPS minimal media with glucose |
| 40 | luc__U_N0075_r1 | luc upregulation, 0.075 ug/ml norfloxacin |
| 40 | luc__U_N0075_r3 | luc upregulation, 0.075 ug/ml norfloxacin |
| 41 | luc__U_N0075_r2 | luc upregulation, 0.075 ug/ml norfloxacin |
| 41 | zipA__U_N0075_r2 | zipA upregulation, 0.075 ug/ml norfloxacin |
| 41 | zipA__U_N0075_r3 | zipA upregulation, 0.075 ug/ml norfloxacin |
| 41 | cspF__U_N0075_r1 | cspF upregulation, 0.075 ug/ml norfloxacin |
| 41 | cspF__U_N0075_r2 | cspF upregulation, 0.075 ug/ml norfloxacin |
| 41 | dam__U_N0075_r1 | dam upregulation, 0.075 ug/ml norfloxacin |
| 41 | dam__U_N0075_r3 | dam upregulation, 0.075 ug/ml norfloxacin |
| 41 | fis__U_N0075_r2 | fis upregulation, 0.075 ug/ml norfloxacin |
| 41 | gcvR__U_N0075_r2 | gcvR upregulation, 0.075 ug/ml norfloxacin |
| 41 | nrdA__U_N0075_r2 | nrdA upregulation, 0.075 ug/ml norfloxacin |
| 41 | ruvC__U_N0075_r2 | ruvC upregulation, 0.075 ug/ml norfloxacin |
| 42 | WT_OPG_r2 | aerobic growth wild-type cells OD 0.2 on MOPS media with glucose |
| 42 | WT_OPG_r3 | aerobic growth wild-type cells OD 0.2 on MOPS media with glucose |
| 42 | WT_OPG_r4 | aerobic growth wild-type cells OD 0.2 on MOPS media with glucose |
| 42 | WT_OPG_r5 | aerobic growth wild-type cells OD 0.2 on MOPS media with glucose |
| 42 | WT_OPG1_r1 | aerobic growth wild-type late log phase 90min MOPS media with glucose |
| 42 | WT_OPG1_r2 | aerobic growth wild-type late log phase 90 min MOPS media with glucose |
| 42 | WT_OPG1_r3 | aerobic growth wild-type late log phase 90 min MOPS media with glucose |
| 42 | WT_OPGA_r1 | aerobic growth wild-type log phase MOPS media with glucose 10 min acid shock pH 2 |
| 42 | WT_OPGA_r2 | aerobic growth wild-type log phase MOPS media with glucose 10 min acid shock pH 2 |
| 42 | WT_OPGC1_r1 | aerobic growth wild-type log phase MOPS media with glucose 10 min ciprofloxacin 20 ng/ml |
| 42 | WT_OPGC2_r1 | aerobic growth wild-type log phase MOPS media with glucose 30 min ciprofloxacin 20 ng/ml |
| 42 | cspA_KOPG_r1 | cspA::Tn5 mutant aerobic growth wild-type log phase MOPS media |
| 42 | dps_KOPG_r1 | dps::Tn5 mutant aerobic growth wild-type log phase MOPS media |
| 42 | dps_KOPG_r2 | dps::Tn5 mutant aerobic growth wild-type log phase MOPS media |
| 42 | dps_KOPG_r3 | dps::Tn5 mutant aerobic growth wild-type log phase MOPS media |
| 42 | hupB_KOPG_r1 | hupB::Tn5 mutant aerobic growth wild-type log phase MOPS media |
| 42 | fnr_DfnrAerobic_r1 | MG1655 with fnr deletion OD 0.2 grown aerobically |
| 42 | fnr_DfnrAerobic_r2 | MG1655 with fnr deletion OD 0.2 grown aerobically |
| 42 | fnr_DfnrAerobic_r3 | MG1655 with fnr deletion OD 0.2 grown aerobically |
| 43 | zipA__U_N0075_r1 | zipA upregulation, 0.075 ug/ml norfloxacin |
| 44 | WT_OPA_r1 | aerobic growth wild-type cells OD 0.2 on MOPS media with acetate |
| 44 | WT_OPA_r2 | aerobic growth wild-type cells OD 0.2 on MOPS media with acetate |
| 44 | WT_OPY_r1 | aerobic growth wild-type cells OD 0.2 on MOPS media with glycerol |
| 44 | WT_OPY_r2 | aerobic growth wild-type cells OD 0.2 on MOPS media with glycerol |

TABLE 5-continued

The clustered microarrays of the *E. coli* compendium.

| Cluster | Chip name | Experiment description |
|---|---|---|
| 44 | WT_OPL_r1 | aerobic growth wild-type cells OD 0.2 on MOPS media with proline |
| 44 | WT_OPL_r2 | aerobic growth wild-type cells OD 0.2 on MOPS media with proline |
| 44 | WT_OPG2_r1 | aerobic growth wild-type stationary phase 135 min MOPS media with glucose |
| 44 | WT_OPG2_r2 | aerobic growth wild-type stationary phase 135 min MOPS media with glucose |
| 44 | csf_succinate_r1 | aerobic growth wild-type cells OD 0.2 on MOPS media with acetate |
| 44 | csf_succinate_r2 | aerobic growth wild-type cells OD 0.2 on MOPS media with acetate |
| 45 | WT_OPG3_r1 | aerobic growth wild-type stationary phase 330 min MOPS media with glucose |
| 45 | WT_OPG3_r2 | aerobic growth wild-type stationary phase 330 min MOPS media with glucose |
| 45 | WT_OPG4_r1 | aerobic growth wild-type stationary phase 480 min MOPS media with glucose |
| 45 | WT_OPG4_r2 | aerobic growth wild-type stationary phase 480 min MOPS media with glucose |
| 45 | WT_OPG5_r1 | aerobic growth wild-type stationary phase 720 min MOPS media with glucose |
| 45 | WT_OPG5_r2 | aerobic growth wild-type stationary phase 720 min MOPS media with glucose |
| 45 | dps_KOPG2_r1 | dps::Tn5 mutant aerobic growth wild-type stationary phase 240 min MOPS media |
| 45 | dps_KOPG2_r2 | dps::Tn5 mutant aerobic growth wild-type stationary phase 240 min MOPS media |
| 45 | dps_KOPG3_r1 | dps::Tn5 mutant aerobic growth wild-type stationary phase 480 min MOPS media |
| 45 | cybr_O_stat_r1 | BW30270 stationary phase, aerobic on MOPS minimal media with glucose |
| 45 | cybr_O_stat_r2 | BW30270 stationary phase, aerobic on MOPS minimal media with glucose |
| 46 | WT_OPGH_r1 | aerobic growth wild-type log phase MOPS media with glucose 10 min heat shock 50° C. |
| 46 | crp_KOPG_r1 | crp::Tn5 mutant aerobic growth wild-type log phase MOPS media |
| 46 | crp_KOPG_r2 | crp::Tn5 mutant aerobic growth wild-type log phase MOPS media |
| 46 | crp_KOPG_r3 | crp::Tn5 mutant aerobic growth wild-type log phase MOPS media |
| 46 | hns_KOPG_r1 | hns::Tn5 mutant aerobic growth wild-type log phase MOPS media |
| 46 | hns_KOPG_r2 | hns::Tn5 mutant aerobic growth wild-type log phase MOPS media |
| 46 | hns_KOPG_r3 | hns::Tn5 mutant aerobic growth wild-type log phase MOPS media |
| 47 | MGD1_t0_r1 | strain BL21 (DE3) with mussel defensin protein MGD1 on T7 controllable plasmid preinduction |
| 47 | MGD1_t30_r2 | strain BL21 (DE3) with mussel defensin protein MGD1 on T7 controllable plasmid 30 min postinduction with 1 mM IPTG |
| 47 | pET3d_t0_r2 | strain BL21 (DE3) with pET3d plasmid and no insert dna (makes 26 amino acid polypeptide) preinduction |
| 48 | MGD1_t0_r2 | strain BL21 (DE3) with mussel defensin protein MGD1 on T7 controllable plasmid preinduction |
| 48 | pET3d_t0_r1 | strain BL21 (DE3) with pET3d plasmid and no insert dna (makes 26 amino acid polypeptide) preinduction |
| 48 | pepAA_t0_r1 | strain BL21 (DE3) with T7 controllable synthetic peptide containing least abundant *E. coli* amino acids preinduction |
| 48 | pepAA_t0_r2 | strain BL21 (DE3) with T7 controllable synthetic peptide containing least abundant *E. coli* amino acids preinduction |
| 48 | pepCO_t0_r1 | strain BL21 (DE3) with T7 controllable synthetic peptide containing most abundant *E. coli* amino acids preinduction |
| 48 | pepCO_t0_r2 | strain BL21 (DE3) with T7 controllable synthetic peptide containing most abundant *E. coli* amino acids preinduction |
| 48 | pepCO_t30_r1 | strain BL21 (DE3) with T7 controllable synthetic peptide 1 mM IPTG |
| 49 | b2618_U_N0075_r1 | b2618 upregulation, 0.075 ug/ml norfloxacin |
| 49 | b2618_U_N0075_r3 | b2618 upregulation, 0.075 ug/ml norfloxacin |
| 49 | bcp__U_N0075_r1 | bcp upregulation, 0.075 ug/ml norfloxacin |
| 49 | bcp__U_N0075_r3 | bcp upregulation, 0.075 ug/ml norfloxacin |
| 49 | cpxR__U_N0075_r1 | cpxR upregulation, 0.075 ug/ml norfloxacin |
| 49 | cpxR__U_N0075_r3 | cpxR upregulation, 0.075 ug/ml norfloxacin |
| 49 | crcB__U_N0075_r1 | crcB upregulation, 0.075 ug/ml norfloxacin |
| 49 | crcB__U_N0075_r3 | crcB upregulation, 0.075 ug/ml norfloxacin |

TABLE 5-continued

The clustered microarrays of the *E. coli* compendium.

| Cluster | Chip name | Experiment description |
|---|---|---|
| 49 | crp__U_N0075_r3 | crp upregulation, 0.075 ug/ml norfloxacin |
| 49 | cspF__U_N0075_r3 | cspF upregulation, 0.075 ug/ml norfloxacin |
| 49 | dnaA__U_N0075_r3 | dnaA upregulation, 0.075 ug/ml norfloxacin |
| 49 | dnaN__U_N0075_r3 | dnaN upregulation, 0.075 ug/ml norfloxacin |
| 49 | dnaT__U_N0075_r3 | dnaT upregulation, 0.075 ug/ml norfloxacin |
| 49 | era__U_N0075_r2 | era upregulation, 0.075 ug/ml norfloxacin |
| 49 | era__U_N0075_r3 | era upregulation, 0.075 ug/ml norfloxacin |
| 49 | fis__U_N0075_r1 | fis upregulation, 0.075 ug/ml norfloxacin |
| 49 | fis__U_N0075_r3 | fis upregulation, 0.075 ug/ml norfloxacin |
| 49 | fklB__U_N0075_r1 | fklB upregulation, 0.075 ug/ml norfloxacin |
| 49 | fklB__U_N0075_r2 | fklB upregulation, 0.075 ug/ml norfloxacin |
| 49 | fklB__U_N0075_r3 | fklB upregulation, 0.075 ug/ml norfloxacin |
| 49 | folA__U_N0075_r1 | folA upregulation, 0.075 ug/ml norfloxacin |
| 49 | folA__U_N0075_r3 | folA upregulation, 0.075 ug/ml norfloxacin |
| 49 | galF__U_N0075_r3 | galF upregulation, 0.075 ug/ml norfloxacin |
| 49 | gcvR__U_N0075_r3 | gcvR upregulation, 0.075 ug/mL norfloxacin |
| 49 | gyrA__U_N0075_r3 | gyrA upregulation, 0.075 ug/mL norfloxacin |
| 49 | hlpA__U_N0075_r3 | hlpA upregulation, 0.075 ug/mL norfloxacin |
| 49 | ldrA__U_N0075_r3 | ldrA upregulation, 0.075 ug/mL norfloxacin |
| 49 | mcrB__U_N0075_r1 | mcrB upregulation, 0.075 ug/mL norfloxacin |
| 49 | mcrB__U_N0075_r2 | mcrB upregulation, 0.075 ug/mL norfloxacin |
| 49 | mcrB__U_N0075_r3 | mcrB upregulation, 0.075 ug/mL norfloxacin |
| 49 | mcrC__U_N0075_r1 | mcrC upregulation, 0.075 ug/mL norfloxacin |
| 49 | mcrC__U_N0075_r2 | mcrC upregulation, 0.075 ug/mL norfloxacin |
| 49 | mcrC__U_N0075_r3 | mcrC upregulation, 0.075 ug/mL norfloxacin |
| 49 | menB__U_N0075_r3 | menB upregulation, 0.075 ug/mL norfloxacin |
| 49 | minE__U_N0075_r3 | minE upregulation, 0.075 ug/mL norfloxacin |
| 49 | pyrC__U_N0075_r1 | pyrC upregulation, 0.075 ug/mL norfloxacin |
| 49 | pyrC__U_N0075_r2 | pyrC upregulation, 0.075 ug/mL norfloxacin |
| 49 | pyrC__U_N0075_r3 | pyrC upregulation, 0.075 ug/mL norfloxacin |
| 49 | rimI__U_N0075_r2 | rimI upregulation, 0.075 ug/mL norfloxacin |
| 49 | uspA__U_N0075_r3 | uspA upregulation, 0.075 ug/mL norfloxacin |
| 50 | b2618_U_N0075_r2 | b2618 upregulation, 0.075 ug/ml norfloxacin |
| 50 | crcB__U_N0075_r2 | crcB upregulation, 0.075 ug/ml norfloxacin |
| 50 | crp__U_N0075_r1 | crp upregulation, 0.075 ug/ml norfloxacin |
| 50 | era__U_N0075_r1 | era upregulation, 0.075 ug/ml norfloxacin |
| 50 | gyrA__U_N0075_r2 | gyrA upregulation, 0.075 ug/mL norfloxacin |
| 50 | ldrA__U_N0075_r1 | ldrA upregulation, 0.075 ug/mL norfloxacin |
| 50 | ldrA__U_N0075_r2 | ldrA upregulation, 0.075 ug/mL norfloxacin |
| 50 | nupC__U_N0075_r1 | nupC upregulation, 0.075 ug/mL norfloxacin |
| 50 | rstB__U_N0075_r2 | rstB upregulation, 0.075 ug/mL norfloxacin |
| 51 | MGD1_t30_r1 | strain BL21 (DE3) with mussel defensin protein MGD1 on T7 controllable plasmid 30 min postinduction with 1 mM IPTG |
| 52 | pET3d_t30_r1 | strain BL21 (DE3) with pET3d plasmid and no insert dna (makes 26 amino acid polypeptide) 30 min postinduction with 1 mM IPTG |
| 52 | pET3d_t30_r2 | strain BL21 (DE3) with pET3d plasmid and no insert dna (makes 26 amino acid polypeptide) 30 min postinduction with 1 mM IPTG |
| 52 | pepAA_t30_r1 | strain BL21 (DE3) with T7 controllable synthetic peptide containing least abundant *E. coli* amino acids 30 min postinduction with 1 mM IPTG |
| 52 | pepAA_t30_r2 | strain BL21 (DE3) with T7 controllable synthetic peptide containing least abundant *E. coli* amino acids 30 min postinduction with 1 mM IPTG |
| 52 | pepCO_t30_r2 | strain BL21 (DE3) with T7 controllable synthetic peptide containing most abundant *E. coli* amino acids 30 min postinduction with 1 mM IPTG |
| 53 | bcp__U_N0075_r2 | bcp upregulation, 0.075 ug/ml norfloxacin |
| 53 | cpxR__U_N0075_r2 | cpxR upregulation, 0.075 ug/ml norfloxacin |
| 53 | crp__U_N0075_r2 | crp upregulation, 0.075 ug/ml norfloxacin |
| 53 | menB__U_N0075_r2 | menB upregulation, 0.075 ug/mL norfloxacin |
| 53 | uspA__U_N0075_r2 | uspA upregulation, 0.075 ug/mL norfloxacin |
| 54 | fnr_wtAnaerobic_r1 | MG1655 OD 0.1 grown anaerobically |
| 54 | fnr_wtAnaerobic_r2 | MG1655 OD 0.1 grown anaerobically |
| 54 | fnr_wtAnaerobic_r3 | MG1655 OD 0.1 grown anaerobically |
| 54 | fnr_DfnrAnaerobic_r1 | MG1655 with fnr deletion OD 0.1 grown anaerobically |
| 54 | fnr_DfnrAnaerobic_r2 | MG1655 with fnr deletion OD 0.1 grown anaerobically |
| 54 | fnr_DfnrAnaerobic_r3 | MG1655 with fnr deletion OD 0.1 grown anaerobically |
| 54 | fnr_DfnrAnaerobic_r4 | MG1655 with fnr deletion OD 0.1 grown anaerobically |
| 54 | cybr_N_log_r1 | BW30270 log phase, anaerobic on MOPS minimal media with glucose |
| 54 | cybr_N_log_r2 | BW30270 log phase, anaerobic on MOPS minimal media with glucose |
| 55 | har_S0_R_noIPTG_r1 | MG1655 with pPROEx-CAT plasmid late log phase in LB with glucose and $MgSO_4$ |

TABLE 5-continued

The clustered microarrays of the *E. coli* compendium.

| Cluster | Chip name | Experiment description |
|---|---|---|
| 55 | har_S0_R_noIPTG_r4 | MG1655 with pPROEx-CAT plasmid late log phase in LB with glucose and MgSO$_4$ |
| 55 | har_S0_R_noIPTG_r2 | MG1655 with pPROEx-CAT plasmid late log phase in LB with glucose and MgSO$_4$ |
| 55 | har_S0_R_noIPTG_r5 | MG1655 with pPROEx-CAT plasmid late log phase in LB with glucose and MgSO$_4$ |
| 55 | har_S0_R_noIPTG_r3 | MG1655 with pPROEx-CAT plasmid late log phase in LB with glucose and MgSO$_4$ |
| 55 | har_S1_R_noIPTG_r1 | MG1655 with pPROEx-CAT plasmid late log phase +1 hr in LB with glucose and MgSO4 |
| 55 | har_S1_R_noIPTG_r2 | MG1655 with pPROEx-CAT plasmid late log phase +1 hr in LB with glucose and MgSO4 |
| 55 | har_S1_R_noIPTG_r3 | MG1655 with pPROEx-CAT plasmid late log phase +1 hr in LB with glucose and MgSO4 |
| 55 | har_S0_noIPTG_r1 | MG1655 late log phase in LB with glucose and MgSO$_4$ |
| 55 | har_S0_noIPTG_r2 | MG1655 late log phase in LB with glucose and MgSO$_4$ |
| 55 | har_S0_noIPTG_r3 | MG1655 late log phase in LB with glucose and MgSO$_4$ |
| 55 | har_S1_noIPTG_r1 | MG1655 late log phase +1 hr in LB with glucose and MgSO$_4$ |
| 55 | har_S1_noIPTG_r2 | MG1655 late log phase +1 hr in LB with glucose and MgSO$_4$ |
| 55 | har_S1_noIPTG_r3 | MG1655 late log phase +1 hr in LB with glucose and MgSO$_4$ |
| 55 | har_S4_noIPTG_r1 | MG1655 late log phase +4 hr in LB with glucose and MgSO$_4$ |
| 55 | har_S4_noIPTG_r2 | MG1655 late log phase +4 hr in LB with glucose and MgSO$_4$ |
| 55 | har_S4_noIPTG_r3 | MG1655 late log phase +4 hr in LB with glucose and MgSO$_4$ |
| 55 | har_S1_IPTG_r1 | MG1655 late log phase +1 hr in LB with glucose and MgSO$_4$ and IPTG |
| 55 | har_S1_IPTG_r2 | MG1655 late log phase +1 hr in LB with glucose and MgSO$_4$ and IPTG |
| 55 | har_S1_IPTG_r3 | MG1655 late log phase +1 hr in LB with glucose and MgSO$_4$ and IPTG |
| 55 | har_S4_IPTG_r1 | MG1655 late log phase +4 hr in LB with glucose and MgSO$_4$ and IPTG |
| 55 | har_S4_IPTG_r2 | MG1655 late log phase +4 hr in LB with glucose and MgSO$_4$ and IPTG |
| 55 | har_S4_IPTG_r3 | MG1655 late log phase +4 hr in LB with glucose and MgSO$_4$ and IPTG |
| 56 | har_S4_R_noIPTG_r1 | MG1655 with pPROEx-CAT plasmid late log phase +4 hr in LB with glucose and MgSO4 |
| 56 | har_S4_R_noIPTG_r2 | MG1655 with pPROEx-CAT plasmid late log phase +4 hr in LB with glucose and MgSO4 |
| 56 | har_S4_R_noIPTG_r3 | MG1655 with pPROEx-CAT plasmid late log phase +4 hr in LB with glucose and MgSO4 |
| 56 | har_S1_R_IPTG_r1 | MG1655 with pPROEx-CAT plasmid late log phase +1 hr in LB with glucose and MgSO4 and IPTG |
| 56 | har_S1_R_IPTG_r2 | MG1655 with pPROEx-CAT plasmid late log phase +1 hr in LB with glucose and MgSO4 and IPTG |
| 56 | har_S1_R_IPTG_r3 | MG1655 with pPROEx-CAT plasmid late log phase +1 hr in LB with glucose and MgSO4 and IPTG |
| 56 | har_S4_R_IPTG_r1 | MG1655 with pPROEx-CAT plasmid late log phase +4 hr in LB with glucose and MgSO4 and IPTG |
| 56 | har_S4_R_IPTG_r2 | MG1655 with pPROEx-CAT plasmid late log phase +4 hr in LB with glucose and MgSO4 and IPTG |
| 56 | har_S4_R_IPTG_r3 | MG1655 with pPROEx-CAT plasmid late log phase +4 hr in LB with glucose and MgSO4 and IPTG |
| 57 | cybr_KNO_N_r1 | MG1655 log phase, anaerobic with nitrate on MOPS minimal media with glucose |
| 57 | cybr_KNO_N_r2 | MG1655 log phase, anaerobic with nitrate on MOPS minimal media with glucose |
| 57 | cybr_N_r1 | MG1655 log phase, anaerobic on MOPS minimal media with glucose |
| 57 | cybr_N_r2 | MG1655 log phase, anaerobic on MOPS minimal media with glucose |
| 58 | ik_L2_T2.5_r1 | K12 EMG2 on LB with 0.2 percent glucose, 2.5 hours post-incubation |
| 58 | ik_L2_T3_r1 | K12 EMG2 on LB with 0.2 percent glucose, 3 hours post-incubation |
| 58 | ik_L2_T3.5_r1 | K12 EMG2 on LB with 0.2 percent glucose, 3.5 hours post-incubation |
| 58 | ik_L2_T4_r1 | K12 EMG2 on LB with 0.2 percent glucose, 4 hours post-incubation |
| 58 | ik_L2_T4.5_r1 | K12 EMG2 on LB with 0.2 percent glucose, 4.5 hours post-incubation |
| 58 | ik_H2_T2.5_r1 | K12 EMG2 on LB with 0.4 percent glucose, 2.5 hours post-incubation |

TABLE 5-continued

The clustered microarrays of the *E. coli* compendium.

| Cluster | Chip name | Experiment description |
|---|---|---|
| 58 | ik_H2_T3_r1 | K12 EMG2 on LB with 0.4 percent glucose, 3 hours post-incubation |
| 58 | ik_H2_T3.5_r1 | K12 EMG2 on LB with 0.4 percent glucose, 3.5 hours post-incubation |
| 59 | ik_L2_T5_r1 | K12 EMG2 on LB with 0.2 percent glucose, 5 hours post-incubation |
| 59 | ik_L2_T5.5_r1 | K12 EMG2 on LB with 0.2 percent glucose, 5.5 hours post-incubation |
| 59 | ik_L2_T6_r1 | K12 EMG2 on LB with 0.2 percent glucose, 6 hours post-incubation |
| 59 | ik_H2_T4_r1 | K12 EMG2 on LB with 0.4 percent glucose, 4 hours post-incubation |
| 59 | ik_H2_T4.5_r1 | K12 EMG2 on LB with 0.4 percent glucose, 4.5 hours post-incubation |
| 59 | ik_H2_T5_r1 | K12 EMG2 on LB with 0.4 percent glucose, 5 hours post-incubation |
| 59 | ik_H2_T5.5_r1 | K12 EMG2 on LB with 0.4 percent glucose, 5.5 hours post-incubation |
| 59 | ik_H2_T6_r1 | K12 EMG2 on LB with 0.4 percent glucose, 6 hours post-incubation |
| 59 | ik_H2_T8_r1 | K12 EMG2 on LB with 0.4 percent glucose, 8 hours post-incubation |
| 60 | ik_L2_T8_r1 | K12 EMG2 on LB with 0.2 percent glucose, 8 hours post-incubation |

Experiments were clustered with the complete-linkage algorithm using inverse CLR scores computed for the microarrays (not the genes) as the pairwise distance metric. The tree was pruned at 60 clusters.

TABLE 6

Functional categories with >=3 unconnected transcription factors at 60% precision

| Functional category* | Transcription factors | Count |
|---|---|---|
| primary metabolism | ada, asnC, cysB, metJ, metR, mlc, prpR, uidA | 8 |
| prophage genes and phage related functions | appY, dicA, dicC, pspF, yagI, ydaS, yfjR | 7 |
| regulation of cellular metabolism | nagC, ycfQ, ydhB, yeaM, yjhU, ynfL, yphH | 7 |
| energy metabolism, carbon | fhlA, glpR, gntR, hyfR, narP, torR | 6 |
| regulation of transcription, DNA-dependent | ycfQ, ydhB, yeaM, yjhU, ynfL, yphH | 6 |
| regulation of nucleobase, nucleoside, nucleotide and nucleic acid metabolism | ycfQ, ydhB, yeaM, yjhU, ynfL, yphH | 6 |
| cellular biosynthesis | asnC, cysB, metJ, metR, mlc, modE | 6 |
| biosynthesis | asnC, cysB, metJ, metR, mlc, modE | 6 |
| energy derivation by oxidation of organic compounds | fhlA, glpR, hyfR, narP, torR | 5 |
| carboxylic acid metabolism | asnC, cysB, metJ, metR, prpR | 5 |
| generation of precursor metabolites and energy | fhlA, glpR, hyfR, narP, torR | 5 |
| organic acid metabolism | asnC, cysB, metJ, metR, prpR | 5 |
| Transcription related | arcA, creB, kdpE, ompR | 4 |
| RNA related | arcA, creB, kdpE, ompR | 4 |
| anaerobic respiration | glpR, hyfR, narP, torR | 4 |
| carbon utilization | atoC, caiF, putA, uhpA | 4 |
| cellular respiration | glpR, hyfR, narP, torR | 4 |
| sulfur metabolism | aslB, cysB, metJ, metR | 4 |
| amino acid and derivative metabolism | asnC, cysB, metJ, metR | 4 |
| amino acid biosynthesis | asnC, cysB, metJ, metR | 4 |
| amine biosynthesis | asnC, cysB, metJ, metR | 4 |
| amino acid metabolism | asnC, cysB, metJ, metR | 4 |
| nitrogen compound biosynthesis | asnC, cysB, metJ, metR | 4 |
| amine metabolism | asnC, cysB, metJ, metR | 4 |
| nitrogen compound metabolism | asnC, cysB, metJ, metR | 4 |
| response to stimulus | ada, cspE, rpoH, ycaL | 4 |
| type of regulation | ybhN, yddM, yjjQ | 3 |
| nucleoproteins, basic proteins | hns, hupA, hupB | 3 |
| protein related | hns, hupA, hupB | 3 |
| biosynthesis of building blocks | birA, putA, trpR | 3 |
| response to temperature stimulus | cspE, rpoH, ycaL | 3 |
| response to abiotic stimulus | cspE, rpoH, ycaL | 3 |
| sulfur compound biosynthesis | cysB, metJ, metR | 3 |
| aspartate family amino acid biosynthesis | asnC, metJ, metR | 3 |

TABLE 6-continued

Functional categories with >=3 unconnected transcription factors at 60% precision

| Functional category* | Transcription factors | Count |
|---|---|---|
| sulfur amino acid biosynthesis | cysB, metJ, metR | 3 |
| aspartate family amino acid metabolism | asnC, metJ, metR | 3 |
| sulfur amino acid metabolism | cysB, metJ, metR | 3 |
| macromolecule metabolism | ada, mlc, uidA | 3 |

*generic/nonspecific GO terms have been removed

TABLE 7

Functional categories with >=15 unconnected genes at 60% precision.

| Functional Category* | Count |
|---|---|
| nucleobase, nucleoside, nucleotide and nucleic acid metabolism | 191 |
| transport | 186 |
| biopolymer metabolism | 171 |
| biosynthesis | 169 |
| cellular biosynthesis | 168 |
| energy metabolism, carbon | 135 |
| energy derivation by oxidation of organic compounds | 135 |
| generation of precursor metabolites and energy | 135 |
| organic acid metabolism | 135 |
| carboxylic acid metabolism | 133 |
| biosynthesis of building blocks | 113 |
| extrachromosomal | 109 |
| carbon utilization | 107 |
| cellular respiration | 100 |
| prophage genes and phage related functions | 99 |
| nitrogen compound metabolism | 96 |
| amine metabolism | 94 |
| amino acid and derivative metabolism | 90 |
| biosynthesis of macromolecules (cellular constituents) | 86 |
| central intermediary metabolism | 85 |
| Channel-type Transporters | 79 |
| carbohydrate metabolism | 76 |
| amino acid metabolism | 76 |
| Pyrophosphate Bond (ATP; GTP; P2) Hydrolysis-driven Active Transporters | 75 |
| catabolism | 74 |
| cellular macromolecule metabolism | 69 |
| The ATP-binding Cassette (ABC) Superfamily + ABC-type Uptake Permeases | 68 |
| anaerobic respiration | 66 |
| carbon compounds | 65 |
| Porters (Uni-, Sym- and Antiporters) | 64 |
| Electrochemical potential driven transporters | 64 |
| RNA metabolism | 64 |
| translation | 59 |
| biopolymer modification | 55 |
| DNA metabolism | 55 |
| macromolecule catabolism | 55 |
| cofactor metabolism | 52 |
| amine biosynthesis | 52 |
| nitrogen compound biosynthesis | 52 |
| cellular protein metabolism | 49 |
| protein metabolism | 49 |
| response to stimulus | 47 |
| cofactor biosynthesis | 46 |
| location of gene products | 45 |
| coenzyme metabolism | 45 |
| RNA modification | 44 |
| cellular carbohydrate metabolism | 44 |
| amino acid biosynthesis | 44 |
| transcriptional activator activity | 44 |
| water-soluble vitamin metabolism | 42 |
| nucleobase, nucleoside and nucleotide interconversion | 42 |
| vitamin metabolism | 42 |
| cellular catabolism | 42 |
| establishment of localization | 41 |
| coenzyme biosynthesis | 39 |
| cell structure | 36 |
| membrane | 34 |
| aerobic respiration | 34 |
| lipid metabolism | 34 |
| cellular lipid metabolism | 34 |
| carbohydrate catabolism | 32 |
| water-soluble vitamin biosynthesis | 31 |
| vitamin biosynthesis | 31 |
| macromolecule biosynthesis | 31 |
| response to stress | 30 |
| carbohydrate biosynthesis | 29 |
| transcriptional repressor activity | 29 |
| DNA replication | 28 |
| aromatic compound metabolism | 27 |
| ABC superfamily, membrane component | 26 |
| lipopolysaccharide | 26 |
| polysaccharide metabolism | 26 |
| ABC superfamily ATP binding cytoplasmic component | 25 |
| outer membrane (sensu Gram-negative Bacteria) | 25 |
| murein (peptidoglycan) | 24 |
| amines | 24 |
| tRNA modification | 24 |
| tRNA metabolism | 24 |
| tRNA aminoacylation for protein translation | 24 |
| amino acid activation | 24 |
| inner membrane | 23 |
| response to abiotic stimulus | 23 |
| cytokinesis | 23 |
| cell division | 23 |
| cellular macromolecule catabolism | 23 |
| regulation of transcription, DNA-dependent | 22 |
| regulation of nucleobase, nucleoside, nucleotide and nucleic acid metabolism | 22 |
| biopolymer catabolism | 22 |
| DNA-dependent DNA replication | 21 |
| aromatic compound biosynthesis | 21 |
| nucleotide metabolism | 20 |
| main pathways of carbohydrate metabolism | 20 |
| cellular polysaccharide metabolism | 20 |
| nucleotide biosynthesis | 20 |
| polysaccharide biosynthesis | 20 |
| biopolymer biosynthesis | 20 |
| cytoplasm | 19 |
| fatty acid oxidation | 19 |
| fatty acid metabolism | 19 |
| protein folding | 19 |
| cellular_component | 19 |
| phosphorous metabolism | 18 |
| heterocycle metabolism | 18 |
| sulfur metabolism | 18 |
| alcohol metabolism | 18 |
| intracellular non-membrane-bound organelle | 18 |
| intracellular organelle | 18 |
| non-membrane-bound organelle | 18 |
| organelle | 18 |
| DNA repair | 17 |
| response to DNA damage stimulus | 17 |
| response to endogenous stimulus | 17 |
| oxidoreduction coenzyme metabolism | 17 |
| glycoprotein metabolism | 17 |
| amino acid derivative metabolism | 16 |
| rRNA metabolism | 16 |
| proteolysis | 16 |
| glycopeptide catabolism | 16 |
| glycoprotein catabolism | 16 |
| proteolysis during cellular protein catabolism | 16 |
| cellular protein catabolism | 16 |
| protein catabolism | 16 |
| protection | 15 |
| fermentation | 15 |
| phospholipid metabolism | 15 |
| membrane lipid metabolism | 15 |
| pteridine and derivative metabolism | 15 |
| pteridine and derivative biosynthesis | 15 |
| carboxylic acid biosynthesis | 15 |

TABLE 7-continued

Functional categories with >=15 unconnected genes at 60% precision.

| Functional Category* | Count |
| --- | --- |
| organic acid biosynthesis | 15 |
| phospholipid biosynthesis | 15 |
| membrane lipid biosynthesis | 15 |
| lipid biosynthesis | 15 |
| transporter activity | 15 |

*generic/nonspecific GO terms have been removed

REFERENCES

1. Read, T. D. et al. The genome sequence of Bacillus anthracis Ames and comparison to closely related bacteria. Nature 423, 81-6 (2003).
2. Aderem, A. Systems biology: its practice and challenges. Cell 121, 511-3 (2005).
3. Basso, K. et al. Reverse engineering of regulatory networks in human B cells. Nat Genet. 37, 382-90 (2005).
4. Beer, M. A. & Tavazoie, S. Predicting gene expression from sequence. Cell 117, 185-98 (2004).
5. Conlon, E. M., Liu, X. S., Lieb, J. D. & Liu, J. S. Integrating regulatory motif discovery and genome-wide expression analysis. Proc Natl Acad Sci USA 100, 3339-44 (2003).
6. de la Fuente, A., Brazhnik, P. & Mendes, P. Linking the genes: inferring quantitative gene networks from microarray data. Trends Genet. 18, 395-8 (2002).
7. di Bernardo, D. et al. Chemogenomic profiling on a genome-wide scale using reverse-engineered gene networks. Nat Biotechnol 23, 377-83 (2005).
8. Friedman, N., Linial, M., Nachman, I. & Pe'er, D. Using Bayesian networks to analyze expression data. J Comput Biol 7, 601-20 (2000).
9. Hashimoto, R. F. et al. Growing genetic regulatory networks from seed genes. Bioinformatics 20, 1241-7 (2004).
10. Kholodenko, B. N. et al. Untangling the wires: a strategy to trace functional interactions in signaling and gene networks. Proc Natl Acad Sci USA 99, 12841-6 (2002).
11. Liao, J. C. et al. Network component analysis: reconstruction of regulatory signals in biological systems. Proc Natl Acad Sci USA 100, 15522-7 (2003).
12. Qian, J., Lin, J., Luscombe, N. M., Yu, H. & Gerstein, M. Prediction of regulatory networks: genome-wide identification of transcription factor targets from gene expression data. Bioinformatics 19, 1917-26 (2003).
13. Ronen, M., Rosenberg, R., Shraiman, B. I. & Alon, U. Assigning numbers to the arrows: parameterizing a gene regulation network by using accurate expression kinetics. Proc Natl Acad Sci USA 99, 10555-60 (2002).
14. Schmitt, W. A., Jr., Raab, R. M. & Stephanopoulos, G. Elucidation of gene interaction networks through time-lagged correlation analysis of transcriptional data. Genome Res 14, 1654-63 (2004).
15. Segal, E. et al. Module networks: identifying regulatory modules and their condition-specific regulators from gene expression data. Nat Genet. 34, 166-76 (2003).
16. Tavazoie, S., Hughes, J. D., Campbell, M. J., Cho, R. J. & Church, G. M. Systematic determination of genetic network architecture. Nat Genet. 22, 281-5 (1999).
17. Tegner, J., Yeung, M. K., Hasty, J. & Collins, J. J. Reverse engineering gene networks: integrating genetic perturbations with dynamical modeling. Proc Natl Acad Sci USA 100, 5944-9 (2003).
18. van Someren, E. P. et al. Least absolute regression network analysis of the murine osteoblast differentiation network. Bioinformatics 22, 477-84 (2006).
19. Harbison, C. T. et al. Transcriptional regulatory code of a eukaryotic genome. Nature 431, 99-104 (2004).
20. Lee, T. I. et al. Transcriptional regulatory networks in Saccharomyces cerevisiae. Science 298, 799-804 (2002).
21. Rice, J. J. & Stolovitzky, G. Making the most of it: pathway reconstruction and integrative simulation using the data at hand. Drug Discovery Today: BioSilico 2, 70-77 (2004).
22. Luscombe, N. M. et al. Genomic analysis of regulatory network dynamics reveals large topological changes. Nature 431, 308-12 (2004).
23. Ideker, T. et al. Integrated genomic and proteomic analyses of a systematically perturbed metabolic network. Science 292, 929-34 (2001).
24. Herrgard, M. J., Covert, M. W. & Palsson, B. O. Reconstruction of microbial transcriptional regulatory networks. Curr Opin Biotechnol 15, 70-7 (2004).
25. Hartemink, A. J., Gifford, D. K., Jaakkola, T. S. & Young, R. A. Combining location and expression data for principled discovery of genetic regulatory network models. Pac Symp Biocomput, 437-49 (2002).
26. Bar-Joseph, Z. et al. Computational discovery of gene modules and regulatory networks. Nat Biotechnol 21, 1337-42 (2003).
27. Salgado, H. et al. RegulonDB (version 5.0): Escherichia coli K-12 transcriptional regulatory network, operon organization, and growth conditions. Nucleic Acids Res 34, D394-7 (2006).
28. Fraser, A. M. & Swinney, H. L. Independent coordinates for strange attractors from mutual information. Physical Review. A 33, 1134-1140 (1986).
29. Roulston, M. Significance testing of information theoretic functionals. Physica D Volume 110, Number 1, 62-66 (5) (1997).
30. Butte, A. J., Tamayo, P., Slonim, D., Golub, T. R. & Kohane, I. S. Discovering functional relationships between RNA expression and chemotherapeutic susceptibility using relevance networks. Proc Natl Acad Sci USA 97, 12182-6 (2000).
31. Thieffry, D., Huerta, A. M., Perez-Rueda, E. & Collado-Vides, J. From specific gene regulation to genomic networks: a global analysis of transcriptional regulation in Escherichia coli. Bioessays 20, 433-40 (1998).
32. Brinkman, A. B., Ettema, T. J., de Vos, W. M. & van der Oost, J. The Lrp family of transcriptional regulators. Mol Microbiol 48, 287-94 (2003).
33. Newman, E. B., Lin, R. T. & D'Ari, R. The Leucine/Lrp Regulon. in Escherichia coli and Salmonella: cellular and molecular biology (eds. Neidhardt, F. C. & Curtiss, R.) (ASM Press, Washington, D.C., 1996).
34. Gerolimatos, B. & Hanson, R. L. Repression of Escherichia coli pyridine nucleotide transhydrogenase by leucine. J Bacteriol 134, 394-400 (1978).
35. Earheart, C. F. Uptake and metabolism of iron and molybdenum. In Escherichia coli and Salmonella: cellular and molecular biology (eds. Neidhardt, F. C. & Curtiss, R.) (ASM Press, Washington, D.C., 1996).
36. Braun, V. & Braun, M. Iron transport and signaling in Escherichia coli. FEBS Lett 529, 78-85 (2002).
37. Kluger, M. J. & Rothenburg, B. A. Fever and reduced iron: their interaction as a host defense response to bacterial infection. Science 203, 374-6 (1979).

38. Bullen, J. J., Rogers, H. J., Spalding, P. B. & Ward, C. G. Iron and infection: the heart of the matter. *FEMS Immunol Med Microbiol* 43, 325-30 (2005).
39. Bullen, J. J., Leigh, L. C. & Rogers, H. J. The effect of iron compounds on the virulence of *Escherichia coli* for guinea-pigs. *Immunology* 15, 581-8 (1968).
40. Forsberg, C. M. & Bullen, J. J. The effect of passage and iron on the virulence of *Pseudomonas aeruginosa*. *J Clin Pathol* 25, 65-8 (1972).
41. Berlutti, F. et al. Iron availability influences aggregation, biofilm, adhesion and invasion of *Pseudomonas aeruginosa* and *Burkholderia cenocepacia*. *Int J Immunopathol Pharmacol* 18, 661-70 (2005).
42. Ardehali, R., Shi, L., Janatova, J., Mohammad, S. F. & Burns, G. L. The effect of apo-transferrin on bacterial adhesion to biomaterials. *Artif Organs* 26, 512-20 (2002).
43. Ardehali, R., Shi, L., Janatova, J., Mohammad, S. F. & Burns, G. L. The inhibitory activity of serum to prevent bacterial adhesion is mainly due to apo-transferrin. *J Biomed Mater Res A* 66, 21-8 (2003).
44. Mey, A. R., Craig, S. A. & Payne, S. M. Characterization of *Vibrio cholerae* RyhB: the RyhB regulon and role of ryhB in biofilm formation. *Infect Immun* 73, 5706-19 (2005).
45. Laub, M. T., Chen, S. L., Shapiro, L. & McAdams, H. H. Genes directly controlled by CtrA, a master regulator of the Caulobacter cell cycle. *Proc Natl Acad Sci USA* 99, 4632-7 (2002).
46. Gardner, T. S., di Bernardo, D., Lorenz, D. & Collins, J. J. Inferring genetic networks and identifying compound mode of action via expression profiling. *Science* 301, 102-5 (2003).
47. Datsenko, K. A. & Wanner, B. L. One-step inactivation of chromosomal genes in *Escherichia coli* K-12 using PCR products. *Proc Natl Acad Sci USA* 97, 6640-5 (2000).
48. Isaacs, F. J. et al. Engineered riboregulators enable post-transcriptional control of gene expression. *Nat Biotechnol* 22, 841-7 (2004).
49. Wu, Z., Irizarry, R. A., Gentleman, R., Martinez-Murillo, F. & Spencer, F. A Model-Based Background Adjustment for Oligonucleotide Expression Arrays. *Journal of the American Statistical Association* 99, 909-917 (2004).
50. Daub, C. O., Steuer, R., Selbig, J. & Kloska, S. Estimating mutual information using B-spline functions—an improved similarity measure for analysing gene expression data. *BMC Bioinformatics* 5, 118 (2004).
51. Lin, D. C. & Grossman, A. D. Identification and characterization of a bacterial chromosome partitioning site. *Cell* 92, 675-85 (1998).
52. Covert, M. W., Knight, E. M., Reed, J. L., Herrgard, M. J. & Palsson, B. O. Integrating high-throughput and computational data elucidates bacterial networks. *Nature* 429, 92-6 (2004).
53. Allen, T. E. et al. Genome-scale analysis of the uses of the *Escherichia coli* genome: model-driven analysis of heterogeneous data sets. *J Bacteriol* 185, 6392-9 (2003).
54. Haddadin, F. T. & Harcum, S. W. Transcriptome profiles for high-cell-density recombinant and wild-type *Escherichia coli*. *Biotechnol Bioeng* 90, 127-53 (2005).
55. Bonomo, J. & Gill, R. T. Amino acid content of recombinant proteins influences the metabolic burden response. *Biotechnol Bioeng* 90, 116-26 (2005).
56. Maurer, L. M., Yohannes, E., Bondurant, S. S., Radmacher, M. & Slonczewski, J. L. pH regulates genes for flagellar motility, catabolism, and oxidative stress in *Escherichia coli* K-12. *J Bacteriol* 187, 304-19 (2005).
57. Brokx, S. J. et al. Genome-wide analysis of lipoprotein expression in *Escherichia coli* MG1655. *J Bacteriol* 186, 3254-8 (2004).
58. Kang, Y., Weber, K. D., Qiu, Y., Kiley, P. J. & Blattner, F. R. Genome-wide expression analysis indicates that FNR of *Escherichia coli* K-12 regulates a large number of genes of unknown function. *J Bacteriol* 187, 1135-60 (2005).
59. Herring, C. D. & Blattner, F. R. Global transcriptional effects of a suppressor tRNA and the inactivation of the regulator formR. *J Bacteriol* 186, 6714-20 (2004).
60. Liu, M. et al. Global transcriptional programs reveal a carbon source foraging strategy by *Escherichia coli*. *J Biol Chem* 280, 15921-7 (2005).
61. Walker, G. C. The SOS Response of *Escherichia coli*. in *Escherichia coli and Salmonella: cellular and molecular biology* (eds. Neidhardt, F. C. & Curtiss, R.) (ASM Press, Washington, D.C., 1996).
62. Gardner, T. S. & Faith, J. J. Reverse-engineering transcription control networks. *Physics of Life Reviews* 2, 65-88 (2005).
63. Butte, A. J., Tamayo, P., Slonim, D., Golub, T. R. & Kohane, I. S. Discovering functional relationships between RNA expression and chemotherapeutic susceptibility using relevance networks. *Proc Natl Acad Sci USA* 97, 12182-6 (2000).
64. Basso, K. et al. Reverse engineering of regulatory networks in human B cells. *Nat Genet.* 37, 382-90 (2005).
65. Friedman, N., Linial, M., Nachman, I. & Pe'er, D. Using Bayesian networks to analyze expression data. *J Comput Biol* 7, 601-20 (2000).
66. Friedman, N. Inferring cellular networks using probabilistic graphical models. *Science* 303, 799-805 (2004).
67. Bailey, T. L. & Elkan, C. Fitting a mixture model by expectation maximization to discover motifs in biopolymers. *Proc Int Conf Intell Syst Mol Biol* 2, 28-36 (1994).
68. Fernandez De Henestrosa, A. R. et al. Identification of additional genes belonging to the LexA regulon in *Escherichia coli*. *Mol Microbiol* 35, 1560-72 (2000).
69. Keseler, I. M. et al. EcoCyc: a comprehensive database resource for *Escherichia coli*. *Nucleic Acids Res* 33, D334-7 (2005).
70. Draghici, S., Khatri, P., Eklund, A. C. & Szallasi, Z. Reliability and reproducibility issues in DNA microarray measurements. *Trends Genet.* 22, 101-9 (2006).
71. Kaeberlein, T., Lewis, K. & Epstein, S. S. Isolating "uncultivable" microorganisms in pure culture in a simulated natural environment. *Science* 296, 1127-9 (2002).
72. Mashburn, L. M. & Whiteley, M. Membrane vesicles traffic signals and facilitate group activities in a prokaryote. *Nature* 437, 422-5 (2005).
73. Vlamakis, H. C. & Kolter, R. Thieves, assassins and spies of the microbial world. *Nat Cell Biol* 7, 933-4 (2005).
74. Xavier, K. B. & Bassler, B. L. Interference with AI-2-mediated bacterial cell-cell communication. *Nature* 437, 750-3 (2005).
75. Box, G. E. P., Hunter, W. G. & Hunter, J. S. *Statistics for experimenters: an introduction to design, data analysis, and model building*, xviii, 653 (Wiley, New York, 1978).
76. Fisher, R. A. *The design of experiments*, xv, 248 (Hafner Pub. Co., New York, 1966).
77. Kerr, M. K. & Churchill, G. A. Experimental design for gene expression microarrays. *Biostatistics* 2, 183-201 (2001).
78. Scholtens, D. et al. Analyzing factorial designed microarray experiments. *Journal of Multivariate Analysis* 90, 19-43 (2004).

79. Shen-Orr, S. S., Milo, R., Mangan, S. & Alon, U. Network motifs in the transcriptional regulation network of *Escherichia coli*. *Nat Genet.* 31, 64-8 (2002).
80. Salgado, H. et al. RegulonDB (version 5.0): *Escherichia coli* K-12 transcriptional regulatory network, operon organization, and growth conditions. *Nucleic Acids Res* 34, D394-7 (2006).
81. Carty, S. M., Sreekumar, K. R. & Raetz, C. R. Effect of cold shock on lipid A biosynthesis in *Escherichia coli*. Induction At 12 degrees C. of an acyltransferase specific for palmitoleoyl-acyl carrier protein. *J Biol Chem* 274, 9677-85 (1999).
82. Xia, B., Ke, H. & Inouye, M. Acquirement of cold sensitivity by quadruple deletion of the cspA family and its suppression by PNPase S1 domain in *Escherichia coli*. *Mol Microbiol* 40, 179-88 (2001).
83. Thieffry, D., Huerta, A. M., Perez-Rueda, E. & Collado-Vides, J. From specific gene regulation to genomic networks: a global analysis of transcriptional regulation in *Escherichia coli*. *Bioessays* 20, 433-40 (1998).
84. Daub, C. O., Steuer, R., Selbig, J. & Kloska, S. Estimating mutual information using B-spline functions—an improved similarity measure for analysing gene expression data. *BMC Bioinformatics* 5, 118 (2004).
85. Roulston, M. Significance testing of information theoretic functionals. *Physica D* Volume 110, Number 1, 62-66 (5) (1997).
86. Segal, E. et al. Module networks: identifying regulatory modules and their condition-specific regulators from gene expression data. *Nat Genet.* 34, 166-76 (2003).

The invention claimed is:

1. A computer-implemented method for identifying a regulatory interaction between a transcription factor and a gene target of said transcription factor, the method comprising:
   a) providing a compendium of biochemical expression measurements reflecting gene expression for a set of biochemical species in an organism wherein at least a subset of said species are transcription factors and a second subset of said species are gene targets of transcription factors;
   b) in a specifically programmed computer, computing mutual information between members of said set of biochemical species;
   c) in a specifically programmed computer, applying a background correction to each said mutual information value so as to identify a set of those mutual information values that are significantly higher than background mutual information values, wherein the step of applying a background correction comprises the step of estimating a likelihood of the mutual information score, MI, for each possible pair of genes, by comparing the mutual information score for that pair to a background distribution of mutual information values, and wherein said set of mutual information values identified in step (c) identifies a regulatory interaction between a transcription factor and a gene target of said transcription factor; and
   d) outputting the identified regulatory interaction to a user interface.

2. A computer-implemented, genome-scale method for predicting a plurality of regulatory interactions between a set of transcription factors and a corresponding set of transcriptional target substrates thereof, comprising:
   a) providing a compendium of biochemical expression measurements reflecting gene expression for a set of biochemical species in an organism wherein at least a subset of said species comprises transcription factors and a second subset of said species comprises transcriptional target substrates of transcription factors;
   b) in a specifically programmed computer, computing mutual information between members of said set of biochemical species;
   c) in a specifically programmed computer, applying a background correction to each said mutual information value, wherein the step of applying a background correction comprises the step of estimating a likelihood of the mutual information score, MI, for each possible pair of genes, by comparing the mutual information score for that pair to a background distribution of mutual information values, thereby identifying a set of those mutual information values that are significantly higher than background mutual information values,
   wherein said set of mutual information values identified in step (c) identifies a plurality of regulatory interactions between a set of transcription factors and a corresponding set of transcriptional target substrates thereof; and
   d) outputting the plurality of regulatory interactions to a user interface.

3. The method of claim 1 wherein said mutual information is pairwise mutual information.

4. The method of claim 1 wherein said mutual information is higher order mutual information.

5. The method of claim 1 wherein said mutual information is computed using one or more of a B-spline approximation, a kernel density estimator, and a discrete approximation.

6. The method of claim 1 wherein said compendium of biochemical expression measurements comprises microarray data.

7. The method of claim 1 wherein said compendium of biochemical expression measurements comprises one or more of mRNA concentration data, protein concentration data, protein activity data, and metabolite concentration or activity data.

8. The method of claim 1 wherein said organism is a microorganism.

9. The method of claim 8 wherein said microorganism is a eukaryotic microorganism.

10. The method of claim 8 wherein said microorganism is a prokaryotic microorganism.

11. The method of claim 1 wherein said compendium of biochemical expression measurements comprises measurements taken when said organism is subject to at least two different environmental conditions or stimuli.

12. The method of claim 1 wherein said background correction is determined by a process comprising the step of computing a background distribution for each mutual information score computed in step (b).

13. The method of claim 1 wherein said step of computing mutual information generates an adjacency matrix or a computationally equivalent representation of mutual information values describing pairwise expression relationships between species represented in said compendium, said matrix having rows and columns of mutual information values, wherein the value in each cell in said matrix is the mutual information between two genes' expression profiles.

14. The method of claim 13 wherein said step of applying a background correction comprises the steps of estimating a likelihood of the mutual information score, MI, for a given pair of genes, genes i and j, representing row or column i and row or column j of said adjacency matrix, by comparing the mutual information score, $MI_{ij}$, for that pair to a background distribution of mutual information values.

15. The method of claim 14 wherein said background distribution is determined through a process comprising:
   i) providing two sets of MI values: $\{MI_i\}$, the set of all mutual information values for gene i, in row or column i of said matrix; and $\{MI_j\}$, the set of mutual information values for gene j, in row or column j of said matrix; and
   ii) calculating marginal empirical distribution $P_i$ and $P_j$ for each set of MI values using an empirical distribution estimation method, then combining into a joint empirical distribution.

16. The method of claim 15 wherein said combining step comprises the product of marginal empirical distributions as $P_i * P_j$.

17. The method of claim 15 wherein the empirical distribution estimation method comprises use of a kernel density estimator or a histogram.

18. The method of claim 17 wherein said kernel density estimator is a Gaussian kernel density estimator.

19. The method of claim 14 wherein said background distribution is determined through a process comprising:
   i) providing two sets of MI values: $\{MI_i\}$, the set of all mutual information values for gene i, in row or column i of said matrix; and $\{MI_j\}$, the set of all mutual information values for gene j, in row or column j of said matrix; and
   ii) approximating a marginal probability density function $g_i(MI_i)$ and $g_j(MI_j)$ for $MI_i$ and $MI_j$ using an analytical function, and combining the probability density functions using a composite analytical function.

20. The method of claim 19 wherein the analytical function is a Gaussian analytical distribution fitted to the set of values of mutual information, $\{MI_i\}$.

21. The method of claim 19 wherein the analytical function is a Rayleigh analytical distribution fitted to the set of values of mutual information, $\{MI_i\}$.

22. The method of claim 19 wherein said composite analytical function is a function of $g_i(MI_i)$ and $g_j(MI_j)$, $f(g(\{MI_i\}), g(MI_j)))$, that represents the probability of the joint function given the two marginal probability density function fits $g_i(MI_i)$ and $g(MI_j)$.

23. The method of claim 22 wherein said composite analytical function comprises a Stouffer method averaging composite function or a $(Z_i+Z_j)/\sqrt{2}$ averaging composite function where $Z_i$ and $Z_j$ are z-scores computed from the two marginal probability density functions.

24. The method of claim 19 wherein said composite analytical function comprises the product of marginal probability density functions $g_i(MI_i)$ and $g(MI_j)$.

25. The method of claim 14, wherein said step of comparing the mutual information score comprises calculating a score by determining the MI pair score in its relative position within probability density functions gi(MIi) and gj(MIj) calculated for $MI_i$ and $MI_j$ using an analytical function.

26. The method of claim 25 wherein said relative position is computed as a z-score for normal distributions or wherein said relative position is computed as a p-value.

27. The method of claim 1 further comprising the step, after step (c), of confirming a physical interaction of a said transcription factor with a said gene target.

28. The method of claim 1 wherein said specifically-programmed computer in steps (b) and (c) is the same computer device.

29. The method of claim 1 wherein said specifically-programmed computer in step (b) is not the same computer device as that used for step (c).

30. A computer-readable physical, non-transitory medium comprising instructions for executing a method, for identifying a regulatory interaction between a transcription factor and a gene target of said transcription factor, the method comprising:
   a) providing a compendium of biochemical expression measurements reflecting gene expression for a set of biochemical species in an organism wherein at least a subset of said species are transcription factors and a second subset of said species are gene targets of transcription factors;
   b) computing mutual information between members of said set of biochemical species;
   c) applying a background correction to each said mutual information value so as to identify a set of those mutual information values that are significantly higher than background mutual information values, wherein the step of applying a background correction comprises the step of estimating a likelihood of the mutual information score, MI, for each possible pair of genes, by comparing the mutual information score for that pair to a background distribution of mutual information values, and wherein said set of mutual information values identified in step (c) identifies a regulatory interaction between a transcription factor and a gene target of said transcription factor; and
   d) outputting the identified regulatory interaction to a user interface.

31. The computer-readable medium of claim 30 which further comprises a compendium of biochemical expression measurements reflecting gene expression for a set of biochemical species in an organism wherein at least a subset of said species are transcription factors and a second subset of said species are gene targets of transcription factors.

32. A computer-readable physical, non-transitory medium comprising instructions for permitting a method, when executed by a processor, for predicting a plurality of regulatory interactions between a set of transcription factors and a corresponding set of transcriptional target substrates thereof, the method comprising:
   a) providing a compendium of biochemical expression measurements reflecting gene expression for a set of biochemical species in an organism wherein at least a subset of said species comprises transcription factors and a second subset of said species comprises transcriptional target substrates of transcription factors;
   b) computing mutual information between members of said set of biochemical species;
   c) applying a background correction to each said mutual information value so as to identify a set of those mutual information values that are significantly higher than background mutual information values, wherein the step of applying a background correction comprises the step of estimating a likelihood of the mutual information score, MI, for each possible pair of genes, by comparing the mutual information score for that pair to a background distribution of mutual information values, and wherein said set of mutual information values identified in step (c) identifies a plurality of regulatory interactions between a set of transcription factors and a corresponding set of transcriptional target substrates thereof; and
   d) outputting the identity of the plurality of regulatory interactions to a user interface.

33. The computer-readable medium of claim 32, further comprising a compendium of biochemical expression measurements reflecting gene expression for a set of biochemical species in an organism wherein at least a subset of said species comprises transcription factors and a second subset of said species comprises transcriptional target substrates of transcription factors.

34. A system for genome-scale method prediction of a plurality of regulatory interactions between a set of transcription factors and a corresponding set of transcriptional target substrates thereof, the system comprising:
   a) a database comprising a compendium of biochemical expression measurements reflecting gene expression for a set of biochemical species in an organism wherein at least a subset of said species comprises transcription factors and a second subset of said species comprises transcriptional target substrates of transcription factors;
   b) a computer system comprising a processor and a computer-readable medium comprising instructions for permitting a method, when executed by said processor, for prediction of a plurality of regulatory interactions between a set of transcription factors and a corresponding set of transcriptional target substrates thereof, the method, using said processor to execute said instructions, comprising:
  i) computing mutual information between members of said set of biochemical species; and
  ii) applying a background correction to each said mutual information value so as to identify a set of those mutual information values that are significantly higher than background mutual information values, herein the step of applying a background correction comprises the step of estimating a likelihood of the mutual information score, MI, for each possible pair of genes, by comparing the mutual information score for that pair to a background distribution of mutual information values, and wherein said set of mutual information values identified in step (c) predicts a plurality of regulatory interactions between a set of transcription factors and a corresponding set of transcriptional target substrates thereof; and
  c) outputting the identities of said regulatory interactions to a user interface.

35. A computer-implemented method for identifying a regulatory interaction between a transcription factor and a gene target of said transcription factor, the method comprising:
  a) providing a compendium of biochemical expression measurements reflecting gene expression for a set of biochemical species in an organism wherein at least a subset of said species are transcription factors and a second subset of said species are gene targets of transcription factors;
  b) in a specifically programmed computer, computing mutual information between members of said set of biochemical species, to generate an adjacency matrix or a computationally equivalent representation of mutual information values describing pairwise expression relationships between species represented in said compendium, said matrix having rows and columns of mutual information values, wherein the value in each cell in said adjacency matrix is the mutual information between two genes' expression profiles;
  c) in a specifically programmed computer, applying a background correction to each said mutual information value so as to identify a set of those mutual information values that are significantly higher than background mutual information values, wherein the step of applying a background correction comprises the step of estimating a likelihood of the mutual information score, MI, for each possible pair of genes, genes i and j, representing row or column i and row or column j of said adjacency matrix, by comparing the mutual information score, $MI_{ij}$, for that pair to a background distribution of mutual information values, and wherein said set of mutual information values identified in step (c) identifies a regulatory interaction between a transcription factor and a gene target of said transcription factor; and
  d) outputting the identified regulatory interaction to a user interface.

36. The method of claim 35, wherein said background distribution of mutual information values is calculated for each said mutual information value to account for all possible interactions that include at least one of the members represented by said mutual information value.

* * * * *